US008153840B2

(12) United States Patent
Woodruff et al.

(10) Patent No.: US 8,153,840 B2
(45) Date of Patent: Apr. 10, 2012

(54) OXIDATION SYSTEM WITH SIDEDRAW SECONDARY REACTOR

(75) Inventors: Thomas Earl Woodruff, Kingsport, TN (US); Alan George Wonders, Kingsport, TN (US)

(73) Assignee: Grupo Petrotemex, S.A. de C.V., San Pedro Garza Garcia (MX)

( * ) Notice: Subject to any disclaimer, the term of this patent is extended or adjusted under 35 U.S.C. 154(b) by 0 days.

(21) Appl. No.: 12/709,547

(22) Filed: Feb. 22, 2010

(65) Prior Publication Data
US 2010/0200804 A1 Aug. 12, 2010

Related U.S. Application Data

(60) Continuation of application No. 11/846,846, filed on Aug. 29, 2007, now Pat. No. 7,829,037, which is a division of application No. 11/366,005, filed on Mar. 1, 2006, now abandoned.

(51) Int. Cl.
*C07C 51/265* (2006.01)
*C07C 63/26* (2006.01)
*C07C 63/16* (2006.01)
(52) U.S. Cl. ......... 562/409; 562/412; 562/418; 562/421
(58) Field of Classification Search .................. 562/409, 562/412, 418, 421
See application file for complete search history.

(56) References Cited

U.S. PATENT DOCUMENTS

| 2,694,622 A | 11/1954 | Reed et al. |
| 3,057,909 A | 10/1962 | Sebelist et al. |
| 3,064,044 A | 11/1962 | Baldwin |
| 3,452,088 A | 6/1969 | Olsen et al. |
| 3,584,039 A | 6/1971 | Meyer |
| 3,626,001 A | 12/1971 | Keith et al. |
| 3,629,321 A | 12/1971 | Longland, Jr. |
| 3,850,983 A | 11/1974 | Park |
| 3,899,485 A | 8/1975 | Immel et al. |
| 3,931,305 A | 1/1976 | Fisher |
| 3,996,271 A | 12/1976 | Yokota et al. |
| 4,158,738 A | 6/1979 | Scott et al. |
| 4,356,319 A | 10/1982 | Roffia et al. |
| 4,500,732 A | 2/1985 | Petty-Weeks et al. |
| 4,594,449 A | 6/1986 | Takuma et al. |
| 4,719,247 A | 1/1988 | Lin et al. |
| 4,772,748 A | 9/1988 | Hashizume et al. |
| 4,892,970 A | 1/1990 | Nowicki et al. |
| 4,898,717 A | 2/1990 | Hsia et al. |
| 4,939,297 A | 7/1990 | Browder et al. |
| 5,095,145 A | 3/1992 | Rosen |
| 5,095,146 A | 3/1992 | Zeitlin et al. |
| 5,171,548 A | 12/1992 | Rossiter et al. |
| 5,175,355 A | 12/1992 | Streich et al. |
| 5,260,239 A | 11/1993 | Hsia |
| 5,359,133 A | 10/1994 | Nazimok et al. |
| 5,510,521 A | 4/1996 | McGehee et al. |
| 5,540,847 A | 7/1996 | Stultz et al. |
| 5,567,842 A | 10/1996 | Izumisawa et al. |
| 5,583,254 A | 12/1996 | Turner et al. |
| 5,756,833 A | 5/1998 | Rosen et al. |
| 5,770,629 A | 6/1998 | Degeorge et al. |
| 5,821,270 A | 10/1998 | Chang et al. |
| 5,958,986 A | 9/1999 | Mart et al. |
| 5,994,567 A | 11/1999 | Kingsley et al. |
| 6,080,372 A | 6/2000 | Machado |
| 6,137,001 A | 10/2000 | Broeker et al. |
| 6,201,030 B1 | 3/2001 | Beer |
| 6,297,348 B1 | 10/2001 | Rodden et al. |
| 6,355,835 B1 | 3/2002 | Kulsrestha et al. |
| 6,392,091 B2 | 5/2002 | Lin |
| 6,436,720 B1 | 8/2002 | Oberbeck et al. |
| 6,504,051 B1 | 1/2003 | Miller, Jr. et al. |
| 6,562,997 B2 | 5/2003 | Sikkenga et al. |
| 6,689,903 B2 | 2/2004 | O'Meadhra et al. |
| 6,765,113 B2 | 7/2004 | Graham et al. |
| 6,800,664 B1 | 10/2004 | Espinoza et al. |
| 6,846,848 B2 | 1/2005 | Wittenbrink et al. |
| 6,949,673 B2 | 9/2005 | Housley et al. |
| 7,132,566 B2 | 11/2006 | Sumner, Jr. et al. |
| 2002/0092584 A1 | 7/2002 | Soininen et al. |
| 2002/0127167 A1 | 9/2002 | Satchell et al. |
| 2002/0183546 A1 | 12/2002 | Sheppard et al. |
| 2002/0193630 A1 | 12/2002 | Lin et al. |
| 2003/0229247 A1 | 12/2003 | Housley et al. |
| 2003/0229248 A1 | 12/2003 | Housley et al. |
| 2004/0087814 A1 | 5/2004 | Gnagnetti et al. |

(Continued)

FOREIGN PATENT DOCUMENTS

DE 27 33 917 A1 2/1978

(Continued)

OTHER PUBLICATIONS

USPTON Notice of Allowance dated May 27, 2010 for copending U.S. Appl. No. 11/365,698. Smith, J.M., "Deviations from Ideal Reactor Performance," Chemical Engineering Kinetics, 1970, second edition, Chapter 6, McGraw-Hill.
Partenheimer, W., "Catalysis Today" 23 (1995) p. 81.
Arun Pal Aneja and Viney Pal Aneja, "The Effect of Water and Air Contamination on Poly(Ethylene Terephthalate) Formation", Polymer Engineering Reviews, 1982, pp. 123-133, vol. 2, No. 2.
V. F. Nazimok et al., "Tere-or Isophthalic Acids," Chemical Abstracts, Mar. 3, 1986, pp. 657, vol. 104, No. 9, Columbus, Ohio.
Copending U.S. Appl. No. 11/366,005, filed Mar. 1, 2006.
Copending U.S. Appl. No. 11/365,698, filed Mar. 1, 2006.
Copending U.S. Appl. No. 11/365,176, filed Mar. 1, 2006.
Copending U.S. Appl. No. 11/365,699, filed Mar. 1, 2006.
Copending U.S. Appl. No. 11/365,248, filed Mar. 1, 2006.
Copending U.S. Appl. No. 11/366,004, filed Mar. 1, 2006.
Copending U.S. Appl. No. 11/365,929, filed Mar. 1, 2006.
Copending U.S. Appl. No. 11/365,258, filed Mar. 1, 2006.

(Continued)

*Primary Examiner* — Peter O Sullivan
(74) *Attorney, Agent, or Firm* — Oblon, Spivak, McClelland, Maier & Neustadt, L.L.P.

(57) ABSTRACT

Disclosed is an optimized process and apparatus for more efficiently and economically carrying out the liquid-phase oxidation of an oxidizable compound. Such liquid-phase oxidation is carried out in a bubble column reactor that provides for a highly efficient reaction at relatively low temperatures. When the oxidized compound is para-xylene and the product from the oxidation reaction is crude terephthalic acid (CTA), such CTA product can be purified and separated by more economical techniques than could be employed if the CTA were formed by a conventional high-temperature oxidation process.

30 Claims, 16 Drawing Sheets

U.S. PATENT DOCUMENTS

| | | |
|---|---|---|
| 2004/0110980 A1 | 6/2004 | Sheppard et al. |
| 2004/0110981 A1 | 6/2004 | Sheppard et al. |
| 2004/0215036 A1 | 10/2004 | Lin et al. |
| 2004/0234435 A1 | 11/2004 | Bickham et al. |
| 2004/0244536 A1 | 12/2004 | Lin |
| 2004/0245176 A1 | 12/2004 | Parker et al. |
| 2005/0038288 A1 | 2/2005 | Lin et al. |
| 2005/0065373 A1 | 3/2005 | Sumner, Jr. et al. |
| 2005/0084432 A1 | 4/2005 | Lin et al. |
| 2005/0107630 A1 | 5/2005 | Belmonte et al. |
| 2005/0159616 A1 | 7/2005 | Parker et al. |
| 2005/0240055 A1 | 10/2005 | Lavoie |
| 2005/0283022 A1 | 12/2005 | Sheppard |
| 2006/0014979 A1 | 1/2006 | Numata et al. |
| 2006/0047142 A1 | 3/2006 | Wonders et al. |
| 2006/0047143 A1 | 3/2006 | Wonders et al. |
| 2006/0047144 A1 | 3/2006 | Wonders et al. |
| 2006/0047146 A1 | 3/2006 | Wonders et al. |
| 2006/0047147 A1 | 3/2006 | Wonders et al. |
| 2006/0047151 A1 | 3/2006 | Wonders et al. |
| 2006/0047159 A1 | 3/2006 | Wonders et al. |
| 2006/0047160 A1 | 3/2006 | Wonders et al. |
| 2006/0047161 A1 | 3/2006 | Wonders et al. |
| 2006/0047163 A1 | 3/2006 | de Vreede et al. |
| 2006/0047166 A1 | 3/2006 | Lin et al. |
| 2006/0205976 A1 | 9/2006 | Wonders et al. |
| 2006/0205977 A1 | 9/2006 | Sumner et al. |

FOREIGN PATENT DOCUMENTS

| | | |
|---|---|---|
| EP | 121 438 A1 | 10/1984 |
| EP | 0111784 B1 | 2/1986 |
| EP | 1 188 476 A2 | 3/2002 |
| GB | 983677 A | 2/1965 |
| GB | 1152575 | 5/1969 |
| GB | 1237298 | 6/1971 |
| GB | 1309451 | 3/1973 |
| GB | 1358520 A | 7/1974 |
| GB | 1373230 | 11/1974 |
| GB | 1454478 A | 11/1976 |
| GB | 2032920 A | 5/1980 |
| GB | 1589310 | 5/1981 |
| GB | 2204581 A | 11/1988 |
| GB | 2310210 A | 8/1997 |
| JP | 52-004277 | 2/1977 |
| JP | 54-025292 | 2/1979 |
| JP | 57 188543 | 11/1982 |
| JP | 5-015788 | 1/1993 |
| JP | 9-157214 | 6/1997 |
| JP | 2001/247511 | 9/2001 |
| JP | 2001/288139 | 10/2001 |
| JP | 2004/168716 | 6/2004 |
| WO | WO 98/08605 A1 | 3/1998 |
| WO | WO 99/31038 A1 | 6/1999 |
| WO | WO 2004/052820 A1 | 6/2004 |
| WO | WO 2005/049873 A1 | 6/2005 |
| WO | WO 2005/075403 A1 | 8/2005 |

OTHER PUBLICATIONS

Copending U.S. Appl. No. 11/325,295, filed Jan. 4, 2006.
U.S. Appl. No. 10/975,252, filed Oct. 28, 2004.
U.S. Appl. No. 10/975,256, filed Oct. 28, 2004.
U.S. Appl. No. 11/154,116, filed Jun. 16, 2005.
U.S. Appl. No. 11/154,140, filed Jun. 16, 2005.
U.S. Appl. No. 11/154,163, filed Jun. 16, 2005.
U.S. Appl. No. 11/154,202, filed Jun. 16, 2005.
U.S. Appl. No. 11/154,219, filed Jun. 16, 2005.
U.S. Appl. No. 11/154,220, filed Jun. 16, 2005.
U.S. Appl. No. 11/154,221, filed Jun. 16, 2005.
U.S. Appl. No. 11/154,448, filed Jun. 16, 2005.
U.S. Appl. No. 11/154,478, filed Jun. 16, 2005.
U.S. Appl. No. 11/154,479, filed Jun. 16, 2005.
U.S. Appl. No. 11/154,480, filed Jun. 16, 2005.
U.S. Appl. No. 11/154,481, filed Jun. 16, 2005.
U.S. Appl. No. 11/154,482, filed Jun. 16, 2005.
U.S. Appl. No. 11/154,484, filed Jun. 16, 2005.
U.S. Appl. No. 11/191,766, filed Jul. 28, 2005.
U.S. Appl. No. 11/201,512, filed Aug. 11, 2005.
U.S. Appl. No. 11/201,799, filed Aug. 11, 2005.
U.S. Appl. No. 11/271,308, filed Nov. 10, 2005.
U.S. Appl. No. 11/325,295, filed Jan. 4, 2006.
U.S. Appl. No. 11/365,054, filed Mar. 1, 2006.
U.S. Appl. No. 11/365,055, filed Mar. 1, 2006.
U.S. Appl. No. 11/365,074, filed Mar. 1, 2006.
U.S. Appl. No. 11/365,079, filed Mar. 1, 2006.
U.S. Appl. No. 11/365,080, filed Mar. 1, 2006.
U.S. Appl. No. 11/365,117, filed Mar. 1, 2006.
U.S. Appl. No. 11/365,255, filed Mar. 1, 2006.
U.S. Appl. No. 11/365,256, filed Mar. 1, 2006.
U.S. Appl. No. 11/365,350, filed Mar. 1, 2006.
U.S. Appl. No. 11/365,439, filed Mar. 1, 2006.
U.S. Appl. No. 11/365,440, filed Mar. 1, 2006.
U.S. Appl. No. 11/365,441, filed Mar. 1, 2006.
U.S. Appl. No. 11/365,461, filed Mar. 1, 2006.
U.S. Appl. No. 11/365,652, filed Mar. 1, 2006.
Copending U.S. Appl. No. 11/846,846, filed Aug. 29, 2007, Thomas Woodruff et al.
USPTO Office Action dated Apr. 20, 2007 for copending U.S. Appl. No. 11/366,005.
USPTO Notice of Allowance dated Sep. 28, 2007 for copending U.S. Appl. No. 11/366,005.
USPTO Office Action dated Nov. 2, 2007 for copending U.S. Appl. No. 11/366,005.
USPTO Office Action dated Jan. 11, 2008 for copending U.S. Appl. No. 11/366,005.
USPTO Office Action dated Jul. 16, 2008 for copending U.S. Appl. No. 11/366,005.
USPTO Office Action dated Jul. 16, 2008 for copending U.S. Appl. No. 11/846,846.
Nauman, E.B., "Chemical Reactor Design, Optimization, and Scaleup," p. 17, 2001, McGraw-Hill Professional.
USPTO Office Action dated Dec. 5, 2008 for copending U.S. Appl. No. 11/846,846.
USPTO Office Action dated Dec. 19, 2008 for copending U.S. Appl. No. 11/365,698.
USPTO Office Action dated May 7, 2009 for copending U.S. Appl. No. 11/846,846.
USPTO Office Action dated Jul. 14, 2009 for copending U.S. Appl. No. 11/365,248.
USPTO Office Action dated Aug. 5, 2009 for copending U.S. Appl. No. 11/365,698.
USPTON Notice of Allowance dated Sep. 3, 2010 for copending U.S. Appl. No. 11/846,846.
USPTON Notice of Allowance dated Aug. 12, 2010 for copending U.S. Appl. No. 11/365,248.
USPTO Office Action dated Feb. 25, 2010 for copending U.S. Appl. No. 11/846,846.
USPTO Office Action dated Apr. 13, 2010 for copending U.S. Appl. No. 11/365,248.
Mexican Office Action issued Mar. 16, 2011, in Patent Application No. MX/a/2008/010936.

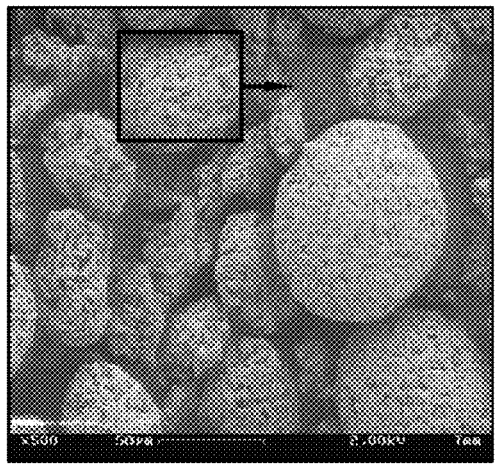 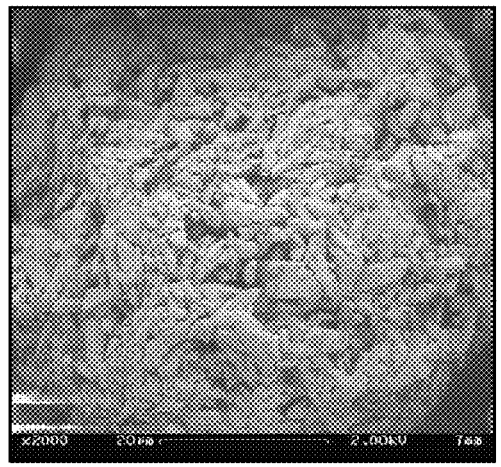
FIG. 28A  FIG. 28B
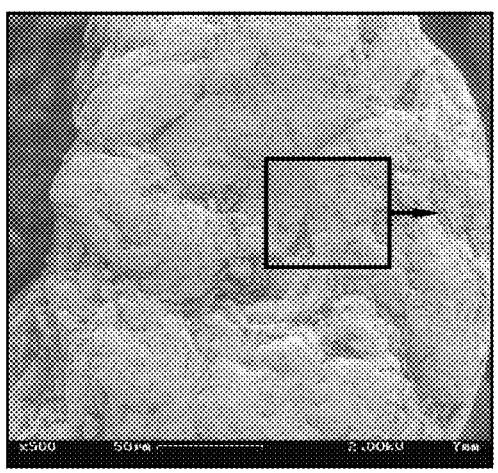 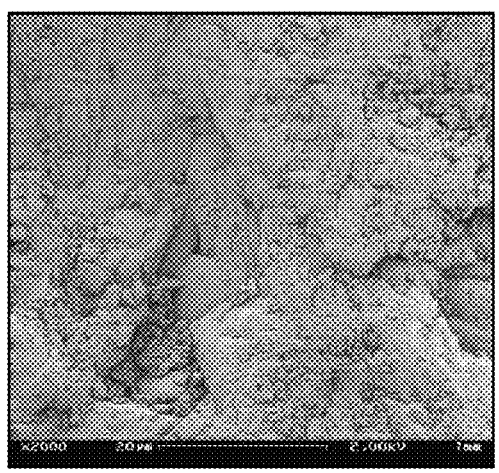
FIG. 29A  FIG. 29B

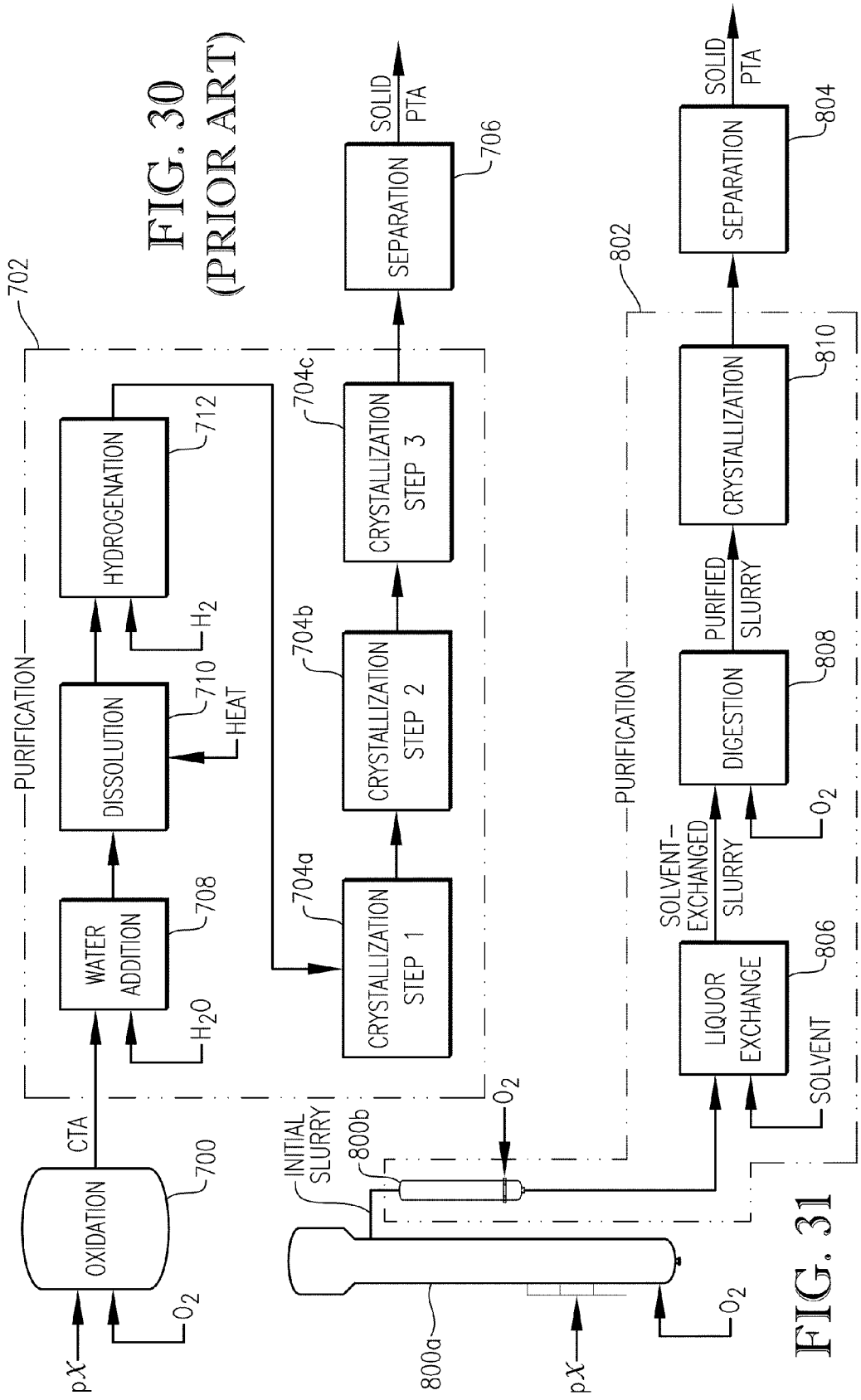

OXIDATION SYSTEM WITH SIDEDRAW SECONDARY REACTOR

CROSS-REFERENCE TO RELATED APPLICATIONS

This Application is a continuation of application Ser. No. 11/846,846, entitled "Oxidation System with Sidedraw Secondary Reactor," filed on Aug. 29, 2007 now U.S. Pat. No. 7,829,037, which Application is a divisional of application Ser. No. 11/366,005, filed on Mar. 1, 2006 now abandoned, the disclosure of which is incorporated herein by reference in its entirety.

FIELD OF THE INVENTION

This invention relates generally to a process for the production of a polycarboxylic acid composition. One aspect of the invention concerns the partial oxidation of a dialkyl aromatic compound (e.g., para-xylene) to produce a crude aromatic dicarboxylic acid (e.g., crude terephthalic acid), which can thereafter be subjected to purification and separation. Another aspect of the invention concerns an improved reactor system that provides for a more effective and economical oxidation process.

BACKGROUND OF THE INVENTION

Oxidation reactions are employed in a variety of existing commercial processes. For example, liquid-phase oxidation is currently used for the oxidation of aldehydes to acids (e.g., propionaldehyde to propionic acid), the oxidation of cyclohexane to adipic acid, and the oxidation of alkyl aromatics to alcohols, acids, or diacids. A particularly significant commercial oxidation process in the latter category (oxidation of alkyl aromatics) is the liquid-phase catalytic partial oxidation of para-xylene to terephthalic acid. Terephthalic acid is an important compound with a variety of applications. The primary use of terephthalic acid is as a feedstock in the production of polyethylene terephthalate (PET). PET is a well-known plastic used in great quantities around the world to make products such as bottles, fibers, and packaging.

In a typical liquid-phase oxidation process, including partial oxidation of para-xylene to terephthalic acid, a liquid-phase feed stream and a gas-phase oxidant stream are introduced into a reactor and form a multi-phase reaction medium in the reactor. The liquid-phase feed stream introduced into the reactor contains at least one oxidizable organic compound (e.g., para-xylene), while the gas-phase oxidant stream contains molecular oxygen. At least a portion of the molecular oxygen introduced into the reactor as a gas dissolves into the liquid phase of the reaction medium to provide oxygen availability for the liquid-phase reaction. If the liquid phase of the multi-phase reaction medium contains an insufficient concentration of molecular oxygen (i.e., if certain portions of the reaction medium are "oxygen-starved"), undesirable side-reactions can generate impurities and/or the intended reactions can be retarded in rate. If the liquid phase of the reaction medium contains too little of the oxidizable compound, the rate of reaction may be undesirably slow. Further, if the liquid phase of the reaction medium contains an excess concentration of the oxidizable compound, additional undesirable side-reactions can generate impurities.

Conventional liquid-phase oxidation reactors are equipped with agitation means for mixing the multi-phase reaction medium contained therein. Agitation of the reaction medium is supplied in an effort to promote dissolution of molecular oxygen into the liquid phase of the reaction medium, maintain relatively uniform concentrations of dissolved oxygen in the liquid phase of the reaction medium, and maintain relatively uniform concentrations of the oxidizable organic compound in the liquid phase of the reaction medium.

Agitation of the reaction medium undergoing liquid-phase oxidation is frequently provided by mechanical agitation means in vessels such as, for example, continuous stirred tank reactors (CSTRs). Although CSTRs can provide thorough mixing of the reaction medium, CSTRs have a number of drawbacks. For example, CSTRs have a relatively high capital cost due to their requirement for expensive motors, fluid-sealed bearings and drive shafts, and/or complex stirring mechanisms. Further, the rotating and/or oscillating mechanical components of conventional CSTRs require regular maintenance. The labor and shutdown time associated with such maintenance adds to the operating cost of CSTRs. However, even with regular maintenance, the mechanical agitation systems employed in CSTRs are prone to mechanical failure and may require replacement over relatively short periods of time.

Bubble column reactors provide an attractive alternative to CSTRs and other mechanically agitated oxidation reactors. Bubble column reactors provide agitation of the reaction medium without requiring expensive and unreliable mechanical equipment. Bubble column reactors typically include an elongated upright reaction zone within which the reaction medium is contained. Agitation of the reaction medium in the reaction zone is provided primarily by the natural buoyancy of gas bubbles rising through the liquid phase of the reaction medium. This natural-buoyancy agitation provided in bubble column reactors reduces capital and maintenance costs relative to mechanically agitated reactors. Further, the substantial absence of moving mechanical parts associated with bubble column reactors provides an oxidation system that is less prone to mechanical failure than mechanically agitated reactors.

When liquid-phase partial oxidation of para-xylene is carried out in a conventional oxidation reactor (CSTR or bubble column), the product withdrawn from the reactor is typically a slurry comprising crude terephthalic acid (CTA) and a mother liquor. CTA contains relatively high levels of impurities (e.g., 4-carboxybenzaldehyde, para-toluic acid, fluorenones, and other color bodies) that render it unsuitable as a feedstock for the production of PET. Thus, the CTA produced in conventional oxidation reactors is typically subjected to a purification process that converts the CTA into purified terephthalic acid (PTA) suitable for making PET.

One typical purification process for converting CTA to PTA includes the following steps: (1) replacing the mother liquor of the CTA-containing slurry with water, (2) heating the CTA/water slurry to dissolve the CTA in water, (3) catalytically hydrogenating the CTA/water solution to convert impurities to more desirable and/or easily-separable compounds, (4) precipitating the resulting PTA from the hydrogenated solution via multiple crystallization steps, and (5) separating the crystallized PTA from the remaining liquids. Although effective, this type of conventional purification process can be very expensive. Individual factors contributing to the high cost of conventional CTA purification methods include, for example, the heat energy required to promote dissolution of the CTA in water, the catalyst required for hydrogenation, the hydrogen stream required for hydrogenation, the yield loss caused by hydrogenation of some terephthalic acid, and the multiple vessels required for multi-step crystallization. Thus, it would be desirable to provide an oxidation system capable of producing a CTA product that could be purified without requiring heat-promoted dissolution in water, hydrogenation, and/or multi-step crystallization.

OBJECTS OF THE INVENTION

It is, therefore, an object of the present invention to provide a more effective and economical liquid-phase oxidation system.

Another object of the invention is to provide a more effective and economical reactor and process for the liquid-phase catalytic partial oxidation of para-xylene to terephthalic acid.

Still another object of the invention is to provide a bubble column reactor that facilitates improved liquid-phase oxidation reactions with reduced formation of impurities.

Yet another object of the invention is to provide a more effective and economical system for producing pure terephthalic acid (PTA) via liquid-phase oxidation of para-xylene to produce crude terephthalic acid (CTA) and subsequently, purifying the CTA to PTA.

A further object of the invention is to provide a bubble column reactor for oxidizing para-xylene and producing a CTA product capable of being purified without requiring heat-promoted dissolution of the CTA in water, hydrogenation of the dissolved CTA, and/or multi-step crystallization of the hydrogenated PTA.

It should be noted that the scope of the present invention, as defined in the appended claims, is not limited to processes or apparatuses capable of realizing all of the objects listed above. Rather, the scope of the claimed invention may encompass a variety of systems that do not accomplish all or any of the above-listed objects. Additional objects and advantages of the present invention will be readily apparent to one skilled in the art upon reviewing the following detailed description and associated drawings.

SUMMARY OF THE INVENTION

One embodiment of the present invention concerns a process for making a polycarboxylic acid composition, the process comprising the following steps: (a) subjecting a multi-phase reaction medium to oxidation in a primary oxidation reactor to thereby produce a first slurry; and (b) subjecting at least a portion of the first slurry to further oxidation in a secondary oxidation reactor, wherein the secondary oxidation reactor is a bubble column reactor.

Another embodiment of the present invention concerns a reactor system. The reactor system includes a primary oxidation reactor and a secondary oxidation reactor. The primary oxidation reactor defines a first inlet and a first outlet. The secondary oxidation reactor is a bubble column reactor that defines a second inlet and a second outlet. The first outlet is coupled in fluid flow communication with the second inlet.

BRIEF DESCRIPTION OF THE DRAWINGS

Preferred embodiments of the invention are described in detail below with reference to the attached drawing figures, wherein;

FIG. 17b is a sectional view of the reactor of FIG. 17a taken along line 17b-17b in FIG. 17a;

FIG. 18b is a sectional view of the reactor of FIG. 18a taken along line 18b-18b in FIG. 18a;

FIG. 19b is a sectional view of the reactor of FIG. 19a taken along line 19b-19b in FIG. 19a;

FIG. 20b is a sectional view of the reactor of FIG. 20a taken along line 20b-20b in FIG. 20a;

FIG. 21b is a sectional view of the reactor of FIG. 21a taken along line 21b-21b in FIG. 21a;

FIG. 22b is a sectional view of the reactor of FIG. 22a taken along line 22b-22b in FIG. 22a;

FIG. 23b is a sectional view of the reactor of FIG. 23a taken along line 23b-23b in FIG. 23a;

FIG. 24b is a sectional view of the reactor of FIG. 24a taken along line 24b-24b in FIG. 24a;

FIG. 25b is a sectional view of the reactor of FIG. 25a taken along line 25b-25b in FIG. 25a;

FIGS. 28A and 28B are magnified views of crude terephthalic acid (CTA) particles produced in accordance with one embodiment of the present invention, particularly illustrating that each CTA particle is a low density, high surface area particle composed of a plurality of loosely-bound CTA sub-particles;

FIGS. 29A and 29B are magnified views of a conventionally-produced CTA, particularly illustrating that the conventional CTA particle has a larger particle size, higher density, and lower surface area than the inventive CTA particle of FIGS. 28A and 28B;

FIG. 30 is a simplified process flow diagram of a prior art process for making purified terephthalic acid (PTA); and FIG. 31 is a simplified process flow diagram of a process for making PTA in accordance with one embodiment of the present invention.

DETAILED DESCRIPTION

One embodiment of the present invention concerns the liquid-phase partial oxidation of an oxidizable compound. Such oxidation is preferably carried out in the liquid phase of a multi-phase reaction medium contained in one or more agitated reactors. Suitable agitated reactors include, for example, bubble-agitated reactors (e.g., bubble column reactors), mechanically agitated reactors (e.g., continuous stirred tank reactors), and flow agitated reactors (e.g., jet reactors). In one embodiment of the invention, the liquid-phase oxidation is carried out using at least one bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority," "primarily," and "predominately" shall mean more than 50 percent. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. As used herein, the term "flow agitation" shall denote agitation of the reaction medium caused by high velocity injection and/or recirculation of one or more fluids in the reaction medium. For example, flow agitation can be provided by nozzles, ejectors, and/or eductors.

In a preferred embodiment of the present invention, less than about 40 percent of the agitation of the reaction medium in the bubble column reactor during oxidation is provided by mechanical and/or flow agitation, more preferably less than about 20 percent of the agitation is provided by mechanical and/or flow agitation, and most preferably less than 5 percent of the agitation is provided by mechanical and/or flow agitation. Preferably, the amount of mechanical and/or flow agitation imparted to the multi-phase reaction medium during oxidation is less than about 3 kilowatts per cubic meter of the reaction medium, more preferably less than about 2 kilowatts per cubic meter, and most preferably less than 1 kilowatt per cubic meter.

Figure 1:
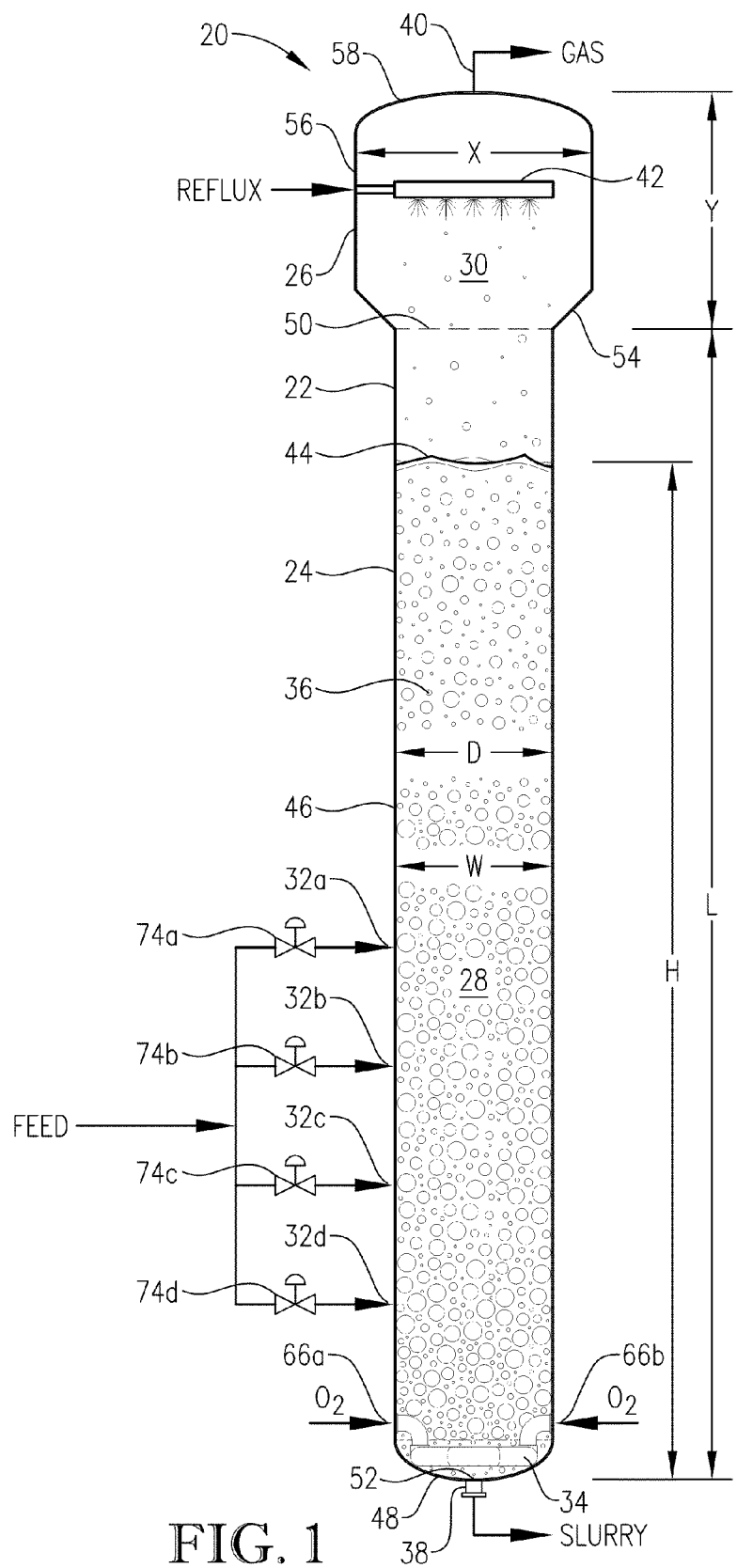
FIG. 1 is a side view of an oxidation reactor constructed in accordance with one embodiment of the present invention, particularly illustrating the introduction of feed, oxidant, and reflux streams into the reactor, the presence of a multi-phase reaction medium in the reactor, and the withdrawal of a gas and a slurry from the top and bottom of the reactor, respectively.

Referring now to FIG. 1, a preferred bubble column reactor 20 is illustrated as comprising a vessel shell 22 having a reaction section 24 and a disengagement section 26. Reaction section 24 defines a reaction zone 28, while disengagement section 26 defines a disengagement zone 30. A predominately liquid-phase feed stream is introduced into reaction zone 28 via feed inlets 32a,b,c,d. A predominately gas-phase oxidant stream is introduced into reaction zone 28 via an oxidant sparger 34 located in the lower portion of reaction zone 28. The liquid-phase feed stream and gas-phase oxidant stream cooperatively form a multi-phase reaction medium 36 within reaction zone 28. Multi-phase reaction medium 36 comprises a liquid phase and a gas phase. More preferably, multiphase reaction medium 36 comprises a three-phase medium having solid-phase, liquid-phase, and gas-phase components. The solid-phase component of the reaction medium 36 preferably precipitates within reaction zone 28 as a result of the oxidation reaction carried out in the liquid phase of reaction medium 36. Bubble column reactor 20 includes a slurry outlet 38 located near the bottom of reaction zone 28 and a gas outlet 40 located near the top of disengagement zone 30. A slurry effluent comprising liquid-phase and solid-phase components of reaction medium 36 is withdrawn from reaction zone 28 via slurry outlet 38, while a predominantly gaseous effluent is withdrawn from disengagement zone 30 via gas outlet 40. The liquid-phase feed stream introduced into bubble column reactor 20 via feed inlets 32a,b,c,d preferably comprises an oxidizable compound, a solvent, and a catalyst system.

The oxidizable compound present in the liquid-phase feed stream preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group," as defined herein, is at least one carbon atom that is bonded only to hydrogen atoms or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

If the oxidizable compound present in the liquid-phase feed stream is a normally-solid compound (i.e., is a solid at standard temperature and pressure), it is preferred for the oxidizable compound to be substantially dissolved in the solvent when introduced into reaction zone 28. It is preferred for the boiling point of the oxidizable compound at atmospheric pressure to be at least about 50° C. More preferably, the boiling point of the oxidizable compound is in the range of from about 80 to about 400° C., and most preferably in the range of from 125 to 155° C. The amount of oxidizable compound present in the liquid-phase feed is preferably in the range of from about 2 to about 40 weight percent, more preferably in the range of from about 4 to about 20 weight percent, and most preferably in the range of from 6 to 15 weight percent.

It is now noted that the oxidizable compound present in the liquid-phase feed may comprise a combination of two or more different oxidizable chemicals. These two or more different chemical materials can be fed commingled in the liquid-phase feed stream or may be fed separately in multiple feed streams. For example, an oxidizable compound comprising para-xylene, meta-xylene, para-tolualdehyde, para-toluic acid, and acetaldehyde may be fed to the reactor via a single inlet or multiple separate inlets.

The solvent present in the liquid-phase feed stream preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably primarily an organic low molecular weight monocarboxylic acid having 1-6 carbon atoms, more preferably 2 carbon atoms. Most preferably, the acid component of the solvent is primarily acetic acid. Preferably, the acid component makes up at least about 75 weight percent of the solvent, more preferably at least about 80 weight percent of the solvent, and most preferably 85 to 98 weight percent of the solvent, with the balance being primarily water. The solvent introduced into bubble column reactor 20 can include small quantities of impurities such as, for example, para-tolualdehyde, terephthaldehyde, 4-carboxybenzaldehyde (4-CBA), benzoic acid, para-toluic acid, para-toluic aldehyde, alpha-bromo-para-toluic acid, isophthalic acid, phthalic acid, trimellitic acid, polyaromatics, and/or suspended particulate. It is preferred that the total amount of impurities in the solvent introduced into bubble column reactor 20 is less than about 3 weight percent.

The catalyst system present in the liquid-phase feed stream is preferably a homogeneous, liquid-phase catalyst system capable of promoting oxidation (including partial oxidation) of the oxidizable compound. More preferably, the catalyst system comprises at least one multivalent transition metal. Still more preferably, the multivalent transition metal comprises cobalt. Even more preferably, the catalyst system comprises cobalt and bromine Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of reaction medium 36 is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of reaction medium 36 is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of reaction medium 36 is maintained in the range of from about 20 to about 1,000 ppmw, more preferably in the range of from about 40 to about 500 ppmw, most preferably in the range of from 50 to 200 ppmw.

The concentrations of the cobalt, bromine, and/or manganese in the liquid phase of reaction medium 36, provided above, are expressed on a time-averaged and volume-averaged basis. As used herein, the term "time-averaged" shall denote an average of at least 10 measurements taken equally over a continuous period of at least 100 seconds. As used herein, the term "volume-averaged" shall denote an average of at least 10 measurements taken at uniform 3-dimensional spacing throughout a certain volume.

The weight ratio of cobalt to bromine (Co:Br) in the catalyst system introduced into reaction zone 28 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced into reaction zone 28 is preferably in the range of from about 0.3:1 to about 40:1, more preferably in the range of from about 5:1 to about 30:1, and most preferably in the range of from 10:1 to 25:1.

The liquid-phase feed stream introduced into bubble column reactor 20 can include small quantities of impurities such as, for example, toluene, ethylbenzene, para-tolualdehyde, terephthaldehyde, 4-carboxybenzaldehyde (4-CBA), benzoic acid, para-toluic acid, para-toluic aldehyde, alpha bromo para-toluic acid, isophthalic acid, phthalic acid, trimellitic acid, polyaromatics, and/or suspended particulate. When bubble column reactor 20 is employed for the production of terephthalic acid, meta-xylene and ortho-xylene are also considered impurities. It is preferred that the total amount of impurities in the liquid-phase feed stream introduced into bubble column reactor 20 is less than about 3 weight percent.

Although FIG. 1 illustrates an embodiment where the oxidizable compound, the solvent, and the catalyst system are mixed together and introduced into bubble column reactor 20 as a single feed stream, in an alternative embodiment of the present invention, the oxidizable compound, the solvent, and the catalyst can be separately introduced into bubble column reactor 20. For example, it is possible to feed a pure para-xylene stream into bubble column reactor 20 via an inlet separate from the solvent and catalyst inlet(s).

The predominately gas-phase oxidant stream introduced into bubble column reactor 20 via oxidant sparger 34 comprises molecular oxygen ($O_2$). Preferably, the oxidant stream comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gasses, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

Referring again to FIG. 1, bubble column reactor 20 is preferably equipped with a reflux distributor 42 positioned above an upper surface 44 of reaction medium 36. Reflux distributor 42 is operable to introduce droplets of a predominately liquid-phase reflux stream into disengagement zone 30 by any means of droplet formation known in the art. More preferably, reflux distributor 42 produces a spray of droplets directed downwardly towards upper surface 44 of reaction medium 36. Preferably, this downward spray of droplets affects (i.e., engages and influences) at least about 50 percent of the maximum horizontal cross-sectional area of disengagement zone 30. More preferably, the spray of droplets affects at least about 75 percent of the maximum horizontal cross-sectional area of disengagement zone 30. Most preferably, the spray of droplets affects at least 90 percent of the maximum horizontal cross-sectional area of disengagement zone 30. This downward liquid reflux spray can help prevent foaming at or above upper surface 44 of reaction medium 36 and can also aid in the disengagement of any liquid or slurry droplets entrained in the upwardly moving gas that flows towards gas outlet 40. Further, the liquid reflux may serve to reduce the amount of particulates and potentially precipitating compounds (e.g., dissolved benzoic acid, para-toluic acid, 4-CBA, terephthalic acid, and catalyst metal salts) exiting in the gaseous effluent withdrawn from disengagement zone 30 via gas outlet 40. In addition, the introduction of reflux droplets into disengagement zone 30 can, by a distillation action, be used to adjust the composition of the gaseous effluent withdrawn via gas outlet 40.

The liquid reflux stream introduced into bubble column reactor 20 via reflux distributor 42 preferably has about the same composition as the solvent component of the liquid-phase feed stream introduced into bubble column reactor 20 via feed inlets 32*a,b,c,d*. Thus, it is preferred for the liquid reflux stream to comprise an acid component and water. The acid component of the reflux stream is preferably a low molecular weight organic monocarboxylic acid having 1-6 carbon atoms, more preferably 2 carbon atoms. Most preferably, the acid component of the reflux stream is acetic acid. Preferably, the acid component makes up at least about 75 weight percent of the reflux stream, more preferably at least about 80 weight percent of the reflux stream, and most preferably 85 to 98 weight percent of the reflux stream, with the balance being water. Because the reflux stream typically has substantially the same composition as the solvent in the liquid-phase feed stream, when this description refers to the "total solvent" introduced into the reactor, such "total solvent" shall include both the reflux stream and the solvent portion of the feed stream.

During liquid-phase oxidation in bubble column reactor 20, it is preferred for the feed, oxidant, and reflux streams to be substantially continuously introduced into reaction zone 28, while the gas and slurry effluent streams are substantially continuously withdrawn from reaction zone 28. As used herein, the term "substantially continuously" shall mean for a period of at least 10 hours interrupted by less than 10 minutes. During oxidation, it is preferred for the oxidizable compound (e.g., para-xylene) to be substantially continuously introduced into reaction zone 28 at a rate of at least about 8,000 kilograms per hour, more preferably at a rate in the range of from about 15,000 to about 200,000 kilograms per hour, still more preferably in the range of from about 22,000 to about 150,000 kilograms per hour, and most preferably in the range of from 30,000 to 100,000 kilograms per hour. Although it is generally preferred for the flow rates of the incoming feed, oxidant, and reflux streams to be substantially steady, it is now noted that one embodiment of the presenting invention contemplates pulsing the incoming feed, oxidant, and/or reflux stream in order to improve mixing and mass transfer. When the incoming feed, oxidant, and/or reflux stream are introduced in a pulsed fashion, it is preferred for their flow rates to vary within about 0 to about 500 percent of the steady-state flow rates recited herein, more preferably within about 30 to about 200 percent of the steady-state flow rates recited herein, and most preferably within 80 to 120 percent of the steady-state flow rates recited herein.

The average space-time rate of reaction (STR) in bubble column oxidation reactor 20 is defined as the mass of the oxidizable compound fed per unit volume of reaction medium 36 per unit time (e.g., kilograms of para-xylene fed per cubic meter per hour). In conventional usage, the amount of oxidizable compound not converted to product would typically be subtracted from the amount of oxidizable compound in the feed stream before calculating the STR. However, conversions and yields are typically high for many of the oxidizable compounds preferred herein (e.g., para-xylene), and it is convenient to define the term herein as stated above. For reasons of capital cost and operating inventory, among others, it is generally preferred that the reaction be conducted with a high STR. However, conducting the reaction at increasingly higher STR may affect the quality or yield of the partial oxidation. Bubble column reactor 20 is particularly useful when the STR of the oxidizable compound (e.g., para-xylene) is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

The oxygen-STR in bubble column oxidation reactor 20 is defined as the weight of molecular oxygen consumed per unit volume of reaction medium 36 per unit time (e.g., kilograms of molecular oxygen consumed per cubic meter per hour). For reasons of capital cost and oxidative consumption of solvent, among others, it is generally preferred that the reaction be conducted with a high oxygen-STR. However, conducting the reaction at increasingly higher oxygen-STR eventually reduces the quality or yield of the partial oxidation. Without being bound by theory, it appears that this possibly relates to the transfer rate of molecular oxygen from the gas phase into the liquid at the interfacial surface area and thence into the bulk liquid. Too high an oxygen-STR possibly leads to too low a dissolved oxygen content in the bulk liquid phase of the reaction medium.

The global-average-oxygen-STR is defined herein as the weight of all oxygen consumed in the entire volume of reaction medium 36 per unit time (e.g., kilograms of molecular oxygen consumed per cubic meter per hour). Bubble column reactor 20 is particularly useful when the global-average-oxygen-STR is in the range of from about 25 kilograms per cubic meter per hour to about 400 kilograms per cubic meter per hour, more preferably in the range of from about 30 kilograms per cubic meter per hour to about 250 kilograms per cubic meter per hour, still more preferably from about 35 kilograms per cubic meter per hour to about 150 kilograms per cubic meter per hour, and most preferably in the range of from 40 kilograms per cubic meter per hour to 100 kilograms per cubic meter per hour.

During oxidation in bubble column reactor 20, it is preferred for the ratio of the mass flow rate of the total solvent (from both the feed and reflux streams) to the mass flow rate of the oxidizable compound entering reaction zone 28 to be maintained in the range of from about 2:1 to about 50:1, more preferably in the range of from about 5:1 to about 40:1, and most preferably in the range of from 7.5:1 to 25:1. Preferably, the ratio of the mass flow rate of solvent introduced as part of the feed stream to the mass flow rate of solvent introduced as part of the reflux stream is maintained in the range of from about 0.5:1 to no reflux stream flow whatsoever, more preferably in the range of from about 0.5:1 to about 4:1, still more preferably in the range of from about 1:1 to about 2:1, and most preferably in the range of from 1.25:1 to 1.5:1.

During liquid-phase oxidation in bubble column reactor 20, it is preferred for the oxidant stream to be introduced into bubble column reactor 20 in an amount that provides molecular oxygen somewhat exceeding the stoichiometric oxygen demand. The amount of excess molecular oxygen required for best results with a particular oxidizable compound affects the overall economics of the liquid-phase oxidation. During liquid-phase oxidation in bubble column reactor 20, it is preferred that the ratio of the mass flow rate of the oxidant stream to the mass flow rate of the oxidizable organic compound (e.g., para-xylene) entering reactor 20 is maintained in the range of from about 0.5:1 to about 20:1, more preferably in the range of from about 1:1 to about 10:1, and most preferably in the range of from 2:1 to 6:1.

Referring again to FIG. 1, the feed, oxidant, and reflux streams introduced into bubble column reactor 20 cooperatively form at least a portion of multi-phase reaction medium 36. Reaction medium 36 is preferably a three-phase medium comprising a solid phase, a liquid phase, and a gas phase. As mentioned above, oxidation of the oxidizable compound (e.g., para-xylene) takes place predominately in the liquid phase of reaction medium 36. Thus, the liquid phase of reaction medium 36 comprises dissolved oxygen and the oxidizable compound. The exothermic nature of the oxidation reaction that takes place in bubble column reactor 20 causes a portion of the solvent (e.g., acetic acid and water) introduced via feed inlets 32a,b,c,d to boil/vaporize. Thus, the gas phase of reaction medium 36 in reactor 20 is formed primarily of vaporized solvent and an undissolved, unreacted portion of the oxidant stream.

Certain prior art oxidation reactors employ heat exchange tubes/fins to heat or cool the reaction medium. However, such heat exchange structures may be undesirable in the inventive reactor and process described herein. Thus, it is preferred for bubble column reactor 20 to include substantially no surfaces that contact reaction medium 36 and exhibit a time-averaged heat flux greater than 30,000 watts per meter squared. In addition, it is preferred for less than about 50 percent of the time-averaged heat of reaction of reaction medium 36 to be removed by heat exchange surfaces, more preferably less than about 30 percent of the heat of reaction is removed by heat exchange surfaces, and most preferably less than 10 percent of the heat or reaction is removed by heat exchange surfaces.

The concentration of dissolved oxygen in the liquid phase of reaction medium 36 is a dynamic balance between the rate of mass transfer from the gas phase and the rate of reactive consumption within the liquid phase (i.e. it is not set simply by the partial pressure of molecular oxygen in the supplying gas phase, though this is one factor in the supply rate of dissolved oxygen and it does affect the limiting upper concentration of dissolved oxygen). The amount of dissolved oxygen varies locally, being higher near bubble interfaces. Globally, the amount of dissolved oxygen depends on the balance of supply and demand factors in different regions of reaction medium 36. Temporally, the amount of dissolved oxygen depends on the uniformity of gas and liquid mixing relative to chemical consumption rates. In designing to match appropriately the supply of and demand for dissolved oxygen in the liquid phase of reaction medium 36, it is preferred for the time-averaged and volume-averaged oxygen concentration in the liquid phase of reaction medium 36 to be maintained above about 1 ppm molar, more preferably in the range from about 4 to about 1,000 ppm molar, still more preferably in the range from about 8 to about 500 ppm molar, and most preferably in the range from 12 to 120 ppm molar.

The liquid-phase oxidation reaction carried out in bubble column reactor 20 is preferably a precipitating reaction that generates solids. More preferably, the liquid-phase oxidation carried out in bubble column reactor 20 causes at least about 10 weight percent of the oxidizable compound (e.g., para-xylene) introduced into reaction zone 28 to form a solid compound (e.g., crude terephthalic acid particles) in reaction medium 36. Still more preferably, the liquid-phase oxidation causes at least about 50 weight percent of the oxidizable compound to form a solid compound in reaction medium 36. Most preferably, the liquid-phase oxidation causes at least 90 weight percent of the oxidizable compound to form a solid compound in reaction medium 36. It is preferred for the total amount of solids in reaction medium 36 to be greater than about 3 percent by weight on a time-averaged and volume-averaged basis. More preferably, the total amount of solids in reaction medium 36 is maintained in the range of from about 5 to about 40 weight percent, still more preferably in the range of from about 10 to about 35 weight percent, and most preferably in the range of from 15 to 30 weight percent. It is preferred for a substantial portion of the oxidation product (e.g., terephthalic acid) produced in bubble column reactor 20 to be present in reaction medium 36 as solids, as opposed to remaining dissolved in the liquid phase of reaction medium 36. The amount of the solid phase oxidation product present in reaction medium 36 is preferably at least about 25 percent by weight of the total oxidation product (solid and liquid phase) in reaction medium 36, more preferably at least about 75 percent by weight of the total oxidation product in reaction medium 36, and most preferably at least 95 percent by weight of the total oxidation product in reaction medium 36. The numerical ranges provided above for the amount of solids in reaction medium 36 apply to substantially steady-state operation of bubble column 20 over a substantially continuous period of time, not to start-up, shut-down, or sub-optimal operation of bubble column reactor 20. The amount of solids in reaction medium 36 is determined by a gravimetric method. In this gravimetric method, a representative portion of slurry is withdrawn from the reaction medium and weighed. At conditions that effectively maintain the overall solid-liquid partitioning present within the reaction medium, free liquid is removed from the solids portion by sedimentation or filtration, effectively without loss of precipitated solids and with less than about 10 percent of the initial liquid mass remaining with the portion of solids. The remaining liquid on the solids is evaporated to dryness, effectively without sublimation of solids. The remaining portion of solids is weighed. The ratio of the weight of the portion of solids to the weight of the original portion of slurry is the fraction of solids, typically expressed as a percentage.

The precipitating reaction carried out in bubble column reactor 20 can cause fouling (i.e., solids build-up) on the surface of certain rigid structures that contact reaction medium 36. Thus, in one embodiment of the present invention, it is preferred for bubble column reactor 20 to include substantially no internal heat exchange, stirring, or baffling structures in reaction zone 28 because such structures would be prone to fouling. If internal structures are present in reaction zone 28, it is desirable to avoid internal structures having outer surfaces that include a significant amount of upwardly facing planar surface area because such upwardly facing planar surfaces would be highly prone to fouling. Thus, if any internal structures are present in reaction zone 28, it is preferred for less than about 20 percent of the total upwardly facing exposed outer surface area of such internal structures to be formed by substantially planar surfaces inclined less than about 15 degrees from horizontal. Internal structures with this type of configuration are referred to herein as having a "non-fouling" configuration.

Referring again to FIG. 1, the physical configuration of bubble column reactor 20 helps provide for optimized oxidation of the oxidizable compound (e.g., para-xylene) with minimal impurity generation. It is preferred for elongated reaction section 24 of vessel shell 22 to include a substantially cylindrical main body 46 and a lower head 48. The upper end of reaction zone 28 is defined by a horizontal plane 50 extending across the top of cylindrical main body 46. A lower end 52 of reaction zone 28 is defined by the lowest internal surface of lower head 48. Typically, lower end 52 of reaction zone 28 is located proximate the opening for slurry outlet 38. Thus, elongated reaction zone 28 defined within bubble column reactor 20 has a maximum length "L" measured from the top end 50 to the bottom end 52 of reaction zone 28 along the axis of elongation of cylindrical main body 46. The length "L" of reaction zone 28 is preferably in the range of from about 10 to about 100 meters, more preferably in the range of from about 20 to about 75 meters, and most preferably in the range of from 25 to 50 meters. Reaction zone 28 has a maximum diameter (width) "D" that is typically equal to the maximum internal diameter of cylindrical main body 46. The maximum diameter "D" of reaction zone 28 is preferably in the range of from about 1 to about 12 meters, more preferably in the range of from about 2 to about 10 meters, still more preferably in the range of from about 3.1 to about 9 meters, and most preferably in the range of from 4 to 8 meters. In a preferred embodiment of the present invention, reaction zone 28 has a length-to-diameter "L:D" ratio in the range of from about 6:1 to about 30:1. Still more preferably, reaction zone 28 has an L:D ratio in the range of from about 8:1 to about 20:1. Most preferably, reaction zone 28 has an L:D ratio in the range of from 9:1 to 15:1.

As discussed above, reaction zone 28 of bubble column reactor 20 receives multi-phase reaction medium 36. Reaction medium 36 has a bottom end coincident with lower end 52 of reaction zone 28 and a top end located at upper surface 44. Upper surface 44 of reaction medium 36 is defined along a horizontal plane that cuts through reaction zone 28 at a vertical location where the contents of reaction zone 28 transitions from a gas-phase-continuous state to a liquid-phase-continuous state. Upper surface 44 is preferably positioned at the vertical location where the local time-averaged gas hold-up of a thin horizontal slice of the contents of reaction zone 28 is 0.9.

Reaction medium 36 has a maximum height "H" measured between its upper and lower ends. The maximum width "W" of reaction medium 36 is typically equal to the maximum diameter "D" of cylindrical main body 46. During liquid-phase oxidation in bubble column reactor 20, it is preferred that H is maintained at about 60 to about 120 percent of L, more preferably about 80 to about 110 percent of L, and most preferably 85 to 100 percent of L. In a preferred embodiment of the present invention, reaction medium 36 has a height-to-width "H:W" ratio greater than about 3:1. More preferably, reaction medium 36 has an H:W ratio in the range of from about 7:1 to about 25:1. Still more preferably, reaction medium 36 has an H:W ratio in the range of from about 8:1 to about 20:1. Most preferably, reaction medium 36 has an H:W ratio in the range of from 9:1 to 15:1. In one embodiment of the invention, L=H and D=W so that various dimensions or ratios provide herein for L and D also apply to H and W, and vice-versa.

The relatively high L:D and H:W ratios provided in accordance with an embodiment of the invention can contribute to several important advantages of the inventive system. As discussed in further detail below, it has been discovered that higher L:D and H:W ratios, as well as certain other features discussed below, can promote beneficial vertical gradients in the concentrations of molecular oxygen and/or the oxidizable compound (e.g., para-xylene) in reaction medium 36. Contrary to conventional wisdom, which would favor a well-mixed reaction medium with relatively uniform concentrations throughout, it has been discovered that the vertical staging of the oxygen and/or the oxidizable compound concentrations facilitates a more effective and economical oxidation reaction. Minimizing the oxygen and oxidizable compound concentrations near the top of reaction medium 36 can help avoid loss of unreacted oxygen and unreacted oxidizable compound through upper gas outlet 40. However, if the concentrations of oxidizable compound and unreacted oxygen are low throughout reaction medium 36, then the rate and/or selectivity of oxidation are reduced. Thus, it is preferred for the concentrations of molecular oxygen and/or the oxidizable compound to be significantly higher near the bottom of reaction medium 36 than near the top of reaction medium 36.

In addition, high L:D and H:W ratios cause the pressure at the bottom of reaction medium 36 to be substantially greater than the pressure at the top of reaction medium 36. This vertical pressure gradient is a result of the height and density of reaction medium 36. One advantage of this vertical pressure gradient is that the elevated pressure at the bottom of the vessel drives more oxygen solubility and mass transfer than would otherwise be achievable at comparable temperatures and overhead pressures in shallow reactors. Thus, the oxidation reaction can be carried out at lower temperatures than would be required in a shallower vessel. When bubble column reactor 20 is used for the partial oxidation of para-xylene to crude terephthalic acid (CTA), the ability to operate at lower reaction temperatures with the same or better oxygen mass transfer rates has a number of advantages. For example, low temperature oxidation of para-xylene reduces the amount of solvent burned during the reaction. As discussed in further detail below, low temperature oxidation also favors the formation of small, high surface area, loosely bound, easily dissolved CTA particles, which can be subjected to more economical purification techniques than the large, low surface area, dense CTA particles produced by conventional high temperature oxidation processes.

During oxidation in reactor 20, it is preferred for the time-averaged and volume-averaged temperature of reaction medium 36 to be maintained in the range of from about 125 to about 200° C., more preferably in the range of from about 140 to about 180° C., and most preferably in the range of from 150 to 170° C. The overhead pressure above reaction medium 36 is preferably maintained in the range of from about 1 to about 20 bar gauge (barg), more preferably in the range of from about 2 to about 12 barg, and most preferably in the range of from 4 to 8 barg. Preferably, the pressure difference between the top of reaction medium 36 and the bottom of reaction medium 36 is in the range of from about 0.4 to about 5 bar, more preferably the pressure difference is in the range of from about 0.7 to about 3 bars, and most preferably the pressure difference is 1 to 2 bar. Although it is generally preferred for the overhead pressure above reaction medium 36 to be maintained at a relatively constant value, one embodiment of the present invention contemplates pulsing the overhead pressure to facilitate improved mixing and/or mass transfer in reaction medium 36. When the overhead pressure is pulsed, it is preferred for the pulsed pressures to range between about 60 to about 140 percent of the steady-state overhead pressure recited herein, more preferably between about 85 and about 115 percent of the steady-state overhead pressure recited herein, and most preferably between 95 and 105 percent of the steady-state overhead pressure recited herein.

A further advantage of the high L:D ratio of reaction zone 28 is that it can contribute to an increase in the average superficial velocity of reaction medium 36. The term "superficial velocity" and "superficial gas velocity," as used herein with reference to reaction medium 36, shall denote the volumetric flow rate of the gas phase of reaction medium 36 at an elevation in the reactor divided by the horizontal cross-sectional area of the reactor at that elevation. The increased superficial velocity provided by the high L:D ratio of reaction zone 28 can promote local mixing and increase the gas hold-up of reaction medium 36. The time-averaged superficial velocities of reaction medium 36 at one-quarter height, half height, and/or three-quarter height of reaction medium 36 are preferably greater than about 0.3 meters per second, more preferably in the range of from about 0.8 to about 5 meters per second, still more preferably in the range of from about 0.9 to about 4 meters per second, and most preferably in the range of from 1 to 3 meters per second.

Referring again to FIG. 1, disengagement section 26 of bubble column reactor 20 is simply a widened portion of vessel shell 22 located immediately above reaction section 24. Disengagement section 26 reduces the velocity of the upwardly-flowing gas phase in bubble column reactor 20 as the gas phase rises above the upper surface 44 of reaction medium 36 and approaches gas outlet 40. This reduction in the upward velocity of the gas phase helps facilitate removal of entrained liquids and/or solids in the upwardly flowing gas phase and thereby reduces undesirable loss of certain components present in the liquid phase of reaction medium 36.

Disengagement section 26 preferably includes a generally frustoconical transition wall 54, a generally cylindrical broad sidewall 56, and an upper head 58. The narrow lower end of transition wall 54 is coupled to the top of cylindrical main body 46 of reaction section 24. The wide upper end of transition wall 54 is coupled to the bottom of broad sidewall 56. It is preferred for transition wall 54 to extend upwardly and outwardly from its narrow lower end at an angle in the range of from about 10 to about 70 degrees from vertical, more preferably in the range of about 15 to about 50 degrees from vertical, and most preferably in the range of from 15 to 45 degrees from vertical. Broad sidewall 56 has a maximum diameter "X" that is generally greater than the maximum diameter "D" of reaction section 24, though when the upper portion of reaction section 24 has a smaller diameter than the overall maximum diameter of reaction section 24, then X may actually be smaller than D. In a preferred embodiment of the present invention, the ratio of the diameter of broad sidewall 56 to the maximum diameter of reaction section 24 "X:D" is in the range of from about 0.8:1 to about 4:1, most preferably in the range of from 1.1:1 to 2:1. Upper head 58 is coupled to the top of broad sidewall 56. Upper head 58 is preferably a generally elliptical head member defining a central opening that permits gas to escape disengagement zone 30 via gas outlet 40. Alternatively, upper head 58 may be of any shape, including conical. Disengagement zone 30 has a maximum height "Y" measured from the top 50 of reaction zone 28 to the uppermost portion of disengagement zone 30. The ratio of the length of reaction zone 28 to the height of disengagement zone 30 "L:Y" is preferably in the range of from about 2:1 to about 24:1, more preferably in the range of from about 3:1 to about 20:1, and most preferably in the range of from 4:1 to 16:1.

Figure 2:
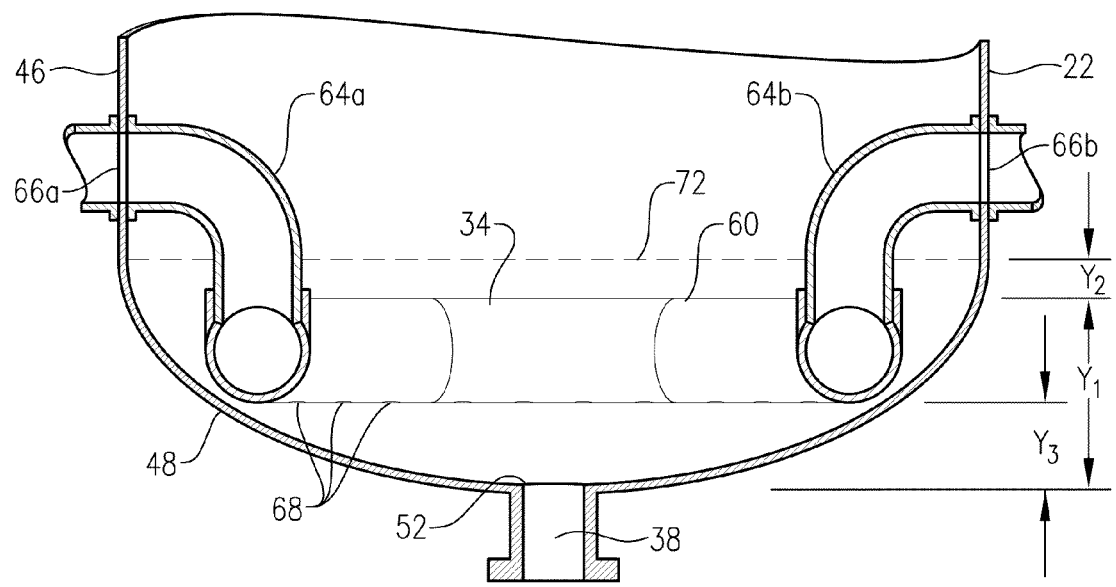
FIG. 2 is an enlarged sectional side view of the bottom of the bubble column reactor taken along line 2-2 in FIG. 3, particularly illustrating the location and configuration of a oxidant sparger used to introduce the oxidant stream into the reactor.
Figure 3:
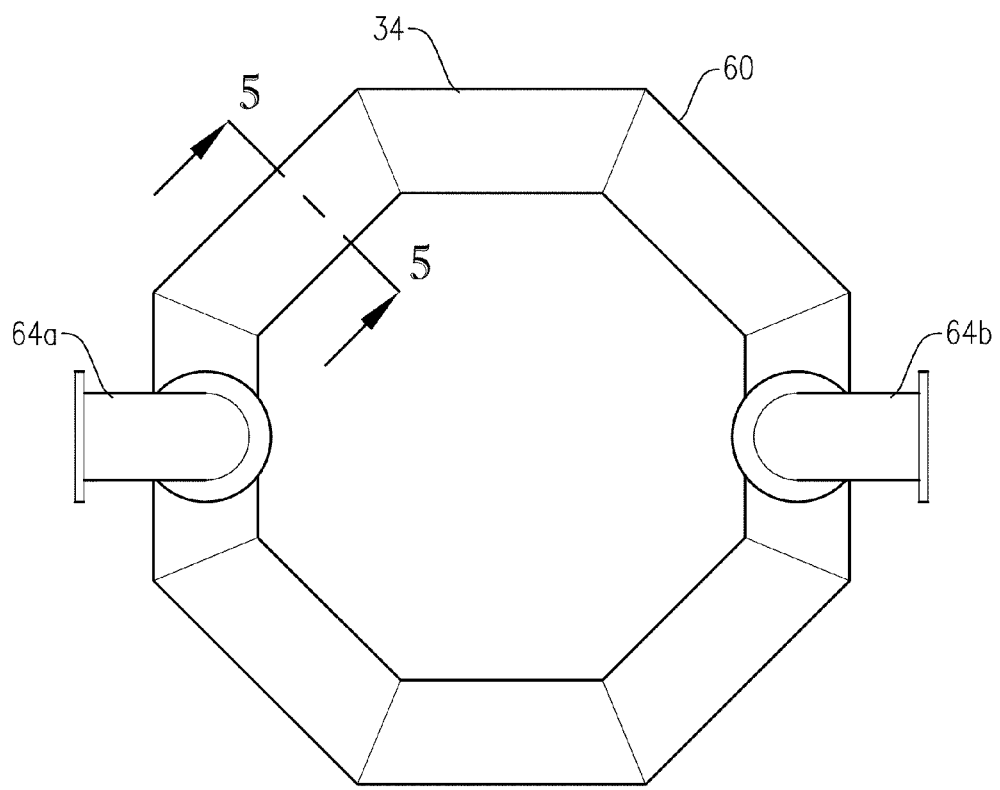
FIG. 3 is a top view of the oxidant sparger of FIG. 2, particularly illustrating that there are no oxidant discharge openings in the top of the oxidant sparger.

Referring now to FIGS. 1-5, the location and configuration of oxidant sparger 34 will now be discussed in greater detail. FIGS. 2 and 3 show that oxidant sparger 34 can include a ring member 60 and a pair of oxidant entry conduits 64a,b. Conveniently, these oxidant entry conduits 64a,b can enter the vessel at an elevation above the ring member 60 and then turn downwards as shown in FIG. 2. Alternatively, an oxidant entry conduit may enter the vessel below the ring member 60 or on about the same horizontal plane as ring member 60. Each oxidant entry conduit 64a,b includes a first end coupled to a respective oxidant inlet 66a,b formed in the vessel shell 22 and a second end fluidly coupled to ring member 60. Ring member 60 is preferably formed of conduits, more preferably of a plurality of straight conduit sections, and most preferably a plurality of straight pipe sections, rigidly coupled to one another to form a tubular polygonal ring. Preferably, ring member 60 is formed of at least 3 straight pipe sections, more preferably 6 to 10 pipe sections, and most preferably 8 pipe sections. Accordingly, when ring member 60 is formed of 8 pipe sections, it has a generally octagonal configuration. It is preferred for the pipe sections that make up oxidant entry conduits 64a,b and ring member 60 to have a nominal diameter greater than about 0.1 meter, more preferable in the range of from about 0.2 to about 2 meters, and most preferably in the range of from 0.25 to 1 meters. As perhaps best illustrated in FIG. 3, it is preferred that substantially no openings are formed in the upper portion of sparger ring 60.

Figure 4:
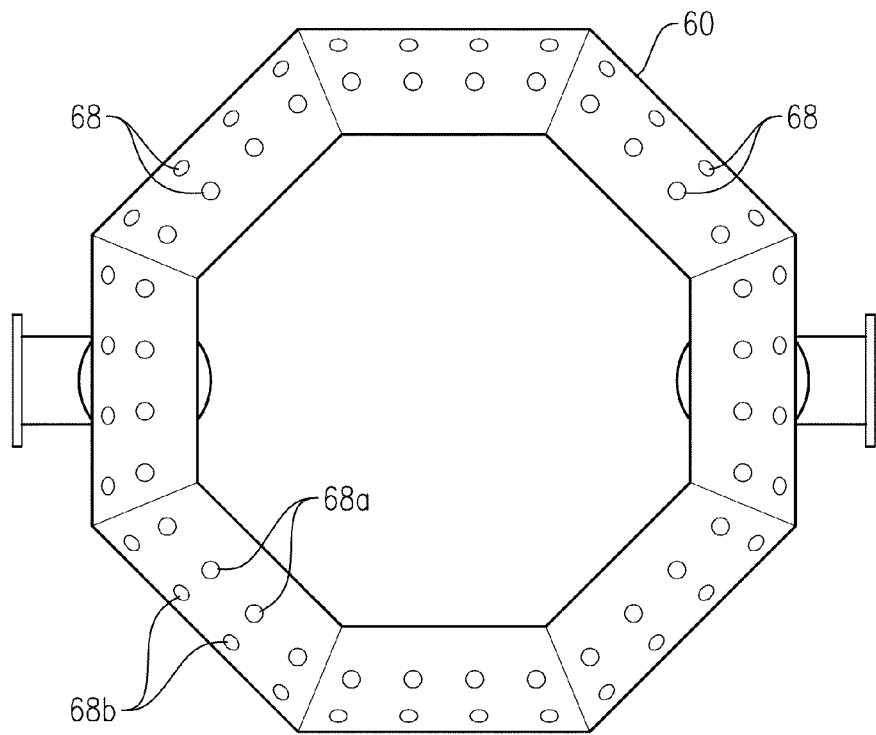
FIG. 4 is a bottom view of the oxidant sparger of FIG. 2, particularly illustrating the configuration of the oxidant discharge openings in the bottom of the oxidant sparger.
Figure 5:
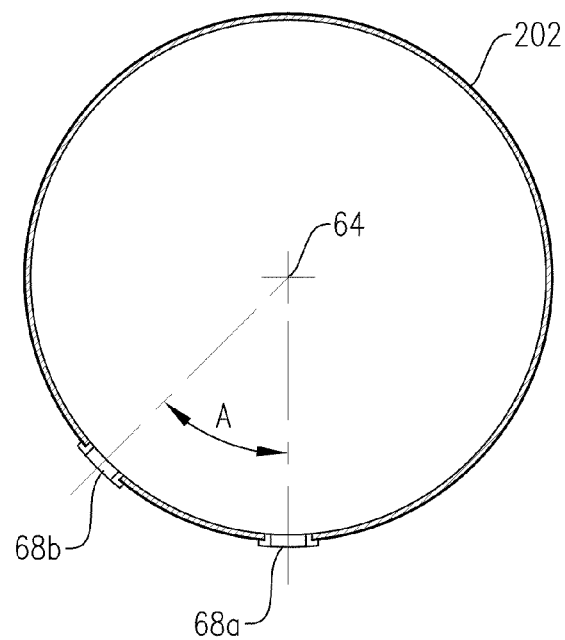
FIG. 5 is a sectional side view of the oxidant sparger taken along line 5-5 in FIG. 3, particularly illustrating the orientation of the oxidant discharge openings in the bottom of the oxidant sparger.

As perhaps best illustrated in FIGS. 4 and 5, the bottom portion of oxidant sparger ring 60 presents a plurality of oxidant openings 68. Oxidant openings 68 are preferably configured such that at least about 1 percent of the total open area defined by oxidant openings 68 is located below the centerline 64 (FIG. 5) of ring member 60, where centerline 64 is located at the elevation of the volumetric centroid of ring member 60. More preferably, at least about 5 percent of the total open area defined by all oxidant openings 68 is located below centerline 64, with at least about 2 percent of the total open area being defined by openings 68 that discharge the oxidant stream in a generally downward direction within about 30 degrees of vertical. Still more preferably, at least about 20 percent of the total open area defined by all oxidant openings 68 is located below centerline 64, with at least about 10 percent of the total open area being defined by openings 68 that discharge the oxidant stream in a generally downward direction within 30 degrees of vertical. Most preferably, at least about 75 percent of the total open area defined by all oxidant openings 68 is located below centerline 64, with at least about 40 percent of the total open area being defined by openings 68 that discharge the oxidant stream in a generally downward direction within 30 degrees of vertical. The fraction of the total open area defined by all oxidant openings 68 that are located above centerline 64 is preferably less than about 75 percent, more preferably less than about 50 percent, still more preferably less than about 25 percent, and most preferably less than 5 percent.

As illustrated in FIGS. 4 and 5, oxidant openings 68 include downward openings 68a and skewed openings 68b. Downward openings 68a are configured to discharge the oxidant stream generally downwardly at an angle within about 30 degrees of vertical, more preferably within about 15 degrees of vertical, and most preferably within 5 degrees of vertical. Referring now to FIG. 5, skewed openings 68b are configured to discharge the oxidant stream generally outwardly and downwardly at an angle "A" that is in the range of from about 15 to about 75 degrees from vertical, more preferably angle A is in the range of from about 30 to about 60 degrees from vertical, and most preferably angle A is in the range of 40 to 50 degrees from vertical.

It is preferred for substantially all oxidant openings 68 to have approximately the same diameter. The diameter of oxidant openings 68 is preferably in the range of from about 2 to about 300 millimeters, more preferably in the range of from about 4 to about 120 millimeters, and most preferably in the range of from 8 to 60 millimeters. The total number of oxidant openings 68 in ring member 60 is selected to meet the low pressure drop criteria detailed below. Preferably, the total number of oxidant openings 68 formed in ring member 60 is at least about 10, more preferably the total number of oxidant openings 68 is in the range of from about 20 to about 200, and most preferably the total number of oxidant openings 68 is in the range of from 40 to 100.

Although FIGS. 1-5 illustrate a very specific configuration for oxidant sparger 34, it is now noted that a variety of oxidant sparger configurations can be employed to achieve the advantages described herein. For example, an oxidant sparger does not necessarily need to have the octagonal ring member configuration illustrated in FIGS. 1-5. Rather, it is possible for an oxidant sparger to be formed of any configuration of flow conduit(s) that employs a plurality of spaced-apart openings for discharging the oxidant stream. The size, number, and discharge direction of the oxidant openings in the flow conduit are preferably within the ranges stated above. Further, the oxidant sparger is preferably configured to provide the azimuthal and radial distribution of molecular oxygen described above.

Regardless of the specific configuration of oxidant sparger 34, it is preferred for the oxidant sparger to be physically configured and operated in a manner that minimizes the pressure drop associated with discharging the oxidant stream out of the flow conduit(s), through the oxidant openings, and into the reaction zone. Such pressure drop is calculated as the time-averaged static pressure of the oxidant stream inside the flow conduit at oxidant inlets 66a,b of the oxidant sparger minus the time-averaged static pressure in the reaction zone at the elevation where one-half of the oxidant stream is introduced above that vertical location and one-half of the oxidant stream is introduced below that vertical location. In a preferred embodiment of the present invention, the time-averaged pressure drop associated with discharging the oxidant stream from the oxidant sparger is less than about 0.3 megapascal (MPa), more preferably less than about 0.2 MPa, still more preferably less than about 0.1 MPa, and most preferably less than 0.05 MPa.

Optionally, a continuous or intermittent flush can be provided to oxidant sparger 34 with a liquid (e.g., acetic acid, water, and/or para-xylene) to prevent fouling of the oxidant sparger with solids. When such a liquid flush is employed, it is preferred for an effective amount of the liquid (i.e., not just the minor amount of liquid droplets that might naturally be present in the oxidant stream) to be passed through the oxidant sparger and out of the oxidant openings for at least one period of more than one minute each day. When a liquid is continuously or periodically discharged from oxidant sparger 34, it is preferred for the time-averaged ratio of the mass flow rate of the liquid through the oxidant sparger to the mass flow rate of the molecular oxygen through the oxidant sparger to be in the range of from about 0.05:1 to about 30:1, or in the range of from about 0.1:1 to about 2:1, or even in the range of from 0.2:1 to 1:1.

In many conventional bubble column reactors containing a multi-phase reaction medium, substantially all of the reaction medium located below the oxidant sparger (or other mechanism for introducing the oxidant stream into the reaction zone) has a very low gas hold-up value. As known in the art, "gas hold-up" is simply the volume fraction of a multi-phase medium that is in the gaseous state. Zones of low gas hold-up in a medium can also be referred to as "unaerated" zones. In many conventional slurry bubble column reactors, a significant portion of the total volume of the reaction medium is located below the oxidant sparger (or other mechanism for introducing the oxidant stream into the reaction zone). Thus, a significant portion of the reaction medium present at the bottom of conventional bubble column reactors is unaerated.

It has been discovered that minimizing the amount of unaerated zones in a reaction medium subjected to oxidization in a bubble column reactor can minimize the generation of certain types of undesirable impurities. Unaerated zones of a reaction medium contain relatively few oxidant bubbles. This low volume of oxidant bubbles reduces the amount of molecular oxygen available for dissolution into the liquid phase of the reaction medium. Thus, the liquid phase in an unaerated zone of the reaction medium has a relatively low concentration of molecular oxygen. These oxygen-starved, unaerated zones of the reaction medium have a tendency to promote undesirable side reactions, rather than the desired oxidation reaction. For example, when para-xylene is partially oxidized to form terephthalic acid, insufficient oxygen availability in the liquid phase of the reaction medium can cause the formation of undesirably high quantities of benzoic acid and coupled aromatic rings, notably including highly undesirable colored molecules known as fluorenones and anthraquinones.

In accordance with one embodiment of the present invention, liquid-phase oxidation is carried out in a bubble column reactor configured and operated in a manner such that the volume fraction of the reaction medium with low gas hold-up values is minimized This minimization of unaerated zones can be quantified by theoretically partitioning the entire volume of the reaction medium into 2,000 discrete horizontal slices of uniform volume. With the exception of the highest and lowest horizontal slices, each horizontal slice is a discrete volume bounded on its sides by the sidewall of the reactor and bounded on its top and bottom by imaginary horizontal planes. The highest horizontal slice is bounded on its bottom by an imaginary horizontal plane and on its top by the upper surface of the reaction medium. The lowest horizontal slice is bounded on its top by an imaginary horizontal plane and on its bottom by the lower end of the vessel. Once the reaction medium has been theoretically partitioned into 2,000 discrete horizontal slices of equal volume, the time-averaged and volume-averaged gas hold-up of each horizontal slice can be determined When this method of quantifying the amount of unaerated zones is employed, it is preferred for the number of horizontal slices having a time-averaged and volume-averaged gas hold-up less than 0.1 to be less than 30, more preferably less than 15, still more preferably less than 6, even more preferably less than 4, and most preferably less than 2. It is preferred for the number of horizontal slices having a gas hold-up less than 0.2 to be less than 80, more preferably less than 40, still more preferably less than 20, even more preferably less than 12, and most preferably less than 5. It is preferred for the number of horizontal slices having a gas hold-up less than 0.3 to be less than 120, more preferably less than 80, still more preferably less than 40, even more preferably less than 20, and most preferably less than 15.

Referring again to FIGS. 1 and 2, it has been discovered that positioning oxidant sparger 34 lower in reaction zone 28 provides several advantages, including reduction of the amount of unaerated zones in reaction medium 36. Given a height "H" of reaction medium 36, a length "L" of reaction zone 28, and a maximum diameter "D" of reaction zone 28, it is preferred for a majority (i.e., >50 percent by weight) of the oxidant stream to be introduced into reaction zone 28 within about 0.025H, 0.022L, and/or 0.25D of lower end 52 of reaction zone 28. More preferably, a majority of the oxidant stream is introduced into reaction zone 28 within about 0.02H, 0.018L, and/or 0.2D of lower end 52 of reaction zone 28. Most preferably, a majority of the oxidant stream is introduced into reaction zone 28 within 0.015H, 0.013L, and/or 0.15D of lower end 52 of reaction zone 28.

In the embodiment illustrated in FIG. 2, the vertical distance "$Y_1$" between lower end 52 of reaction zone 28 and the outlet of upper oxidant openings 68 of oxidant sparger 34 is less than about 0.25H, 0.022L, and/or 0.25D, so that substantially all of the oxidant stream enters reaction zone 28 within about 0.25H, 0.022L, and/or 0.25D of lower end 52 of reaction zone 28. More preferably, $Y_1$ is less than about 0.02H, 0.018L, and/or 0.2D. Most preferably, $Y_1$ is less than 0.015H, 0.013L, and/or 0.15D, but more than 0.005H, 0.004L, and/or 0.06D. FIG. 2 illustrates a tangent line 72 at the location where the bottom edge of cylindrical main body 46 of vessel shell 22 joins with the top edge of elliptical lower head 48 of vessel shell 22. Alternatively, lower head 48 can be of any shape, including conical, and the tangent line is still defined as the bottom edge of cylindrical main body 46. The vertical distance "$Y_2$" between tangent line 72 and the top of oxidant sparger 34 is preferably at least about 0.0012H, 0.001L, and/or 0.01D; more preferably at least about 0.005H, 0.004L, and/or 0.05D; and most preferably at least 0. O1H, 0.008L, and/or 0.1D. The vertical distance "$Y_3$" between lower end 52 of reaction zone 28 and the outlet of lower oxidant openings 70 of oxidant sparger 34 is preferably less than about 0.015H, 0.013L, and/or 0.15D; more preferably less than about 0.012H, 0.01L, and/or 0.1D; and most preferably less than 0.01H, 0.008L, and/or 0.075D, but more than 0.003H, 0.002L, and/or 0.025D.

In addition to the advantages provided by minimizing unaerated zones (i.e., zones with low gas hold-up) in reaction medium 36, it has been discovered that oxidation can be enhanced by maximizing the gas hold-up of the entire reaction medium 36. Reaction medium 36 preferably has time-averaged and volume-averaged gas hold-up of at least about 0.4, more preferably in the range of from about 0.6 to about 0.9, and most preferably in the range of from 0.65 to 0.85. Several physical and operational attributes of bubble column reactor 20 contribute to the high gas hold-up discussed above. For example, for a given reactor size and flow of oxidant stream, the high L:D ratio of reaction zone 28 yields a lower diameter which increases the superficial velocity in reaction medium 36 which in turn increases gas hold-up. Additionally, the actual diameter of a bubble column and the L:D ratio are known to influence the average gas hold-up even for a given constant superficial velocity. In addition, the minimization of unaerated zones, particularly in the bottom of reaction zone 28, contributes to an increased gas hold-up value. Further, the overhead pressure and mechanical configuration of the bubble column reactor can affect operating stability at the high superficial velocities and gas hold-up values disclosed herein.

Referring again to FIG. 1, it has been discovered that improved distribution of the oxidizable compound (e.g., para-xylene) in reaction medium 36 can be provided by introducing the liquid-phase feed stream into reaction zone 28 at multiple vertically-spaced locations. Preferably, the liquid-phase feed stream is introduced into reaction zone 28 via at least 3 feed openings, more preferably at least 4 feed openings. As used herein, the term "feed openings" shall denote openings where the liquid-phase feed stream is discharged into reaction zone 28 for mixing with reaction medium 36. It is preferred for at least 2 of the feed openings to be vertically-spaced from one another by at least about 0.5D, more preferably at least about 1.5D, and most preferably at least 3D. However, it is preferred for the highest feed opening to be vertically-spaced from the lowest oxidant opening by not more than about 0.75H, 0.65L, and/or 8D; more preferably not more than about 0.5H, 0.4L, and/or 5D; and most preferably not more than 0.4H, 0.35L, and/or 4D.

Although it is desirable to introduce the liquid-phase feed stream at multiple vertical locations, it has also been discovered that improved distribution of the oxidizable compound in reaction medium 36 is provided if the majority of the liquid-phase feed stream is introduced into the bottom half of reaction medium 36 and/or reaction zone 28. Preferably, at least about 75 weight percent of the liquid-phase feed stream is introduced into the bottom half of reaction medium 36 and/or reaction zone 28. Most preferably, at least 90 weight percent of the liquid-phase feed stream is introduced into the bottom half of reaction medium 36 and/or reaction zone 28. In addition, it is preferred for at least about 30 weight percent of the liquid-phase feed stream to be introduced into reaction zone 28 within about 1.5D of the lowest vertical location where the oxidant stream is introduced into reaction zone 28. This lowest vertical location where the oxidant stream is introduced into reaction zone 28 is typically at the bottom of oxidant sparger; however, a variety of alternative configurations for introducing the oxidant stream into reaction zone 28 are contemplated by a preferred embodiment of the present invention. Preferably, at least about 50 weight percent of the liquid-phase feed is introduced within about 2.5D of the lowest vertical location where the oxidant stream is introduced into reaction zone 28. Preferably, at least about 75 weight percent of the liquid-phase feed stream is introduced within about 5D of the lowest vertical location where the oxidant stream is introduced into reaction zone 28.

Each feed opening defines an open area through which the feed is discharged. It is preferred that at least about 30 percent of the cumulative open area of all the feed inlets is located within about 1.5D of the lowest vertical location where the oxidant stream is introduced into reaction zone 28. Preferably, at least about 50 percent of the cumulative open area of all the feed inlets is located within about 2.5D of the lowest vertical location where the oxidant stream is introduced into reaction zone 28. Preferably, at least about 75 percent of the cumulative open area of all the feed inlets is located within about 5D of the lowest vertical location where the oxidant stream is introduced into reaction zone 28.

Referring again to FIG. 1, in one embodiment of the present invention, feed inlets 32a,b,c,d are simply a series of vertically-aligned openings along one side of vessel shell 22. These feed openings preferably have substantially similar diameters of less than about 7 centimeters, more preferably in the range of from about 0.25 to about 5 centimeters, and most preferably in the range of from 0.4 to 2 centimeters. Bubble column reactor 20 is preferably equipped with a system for controlling the flow rate of the liquid-phase feed stream out of each feed opening. Such flow control system preferably includes an individual flow control valve 74a,b,c,d for each respective feed inlet 32a,b,c,d. In addition, it is preferred for bubble column reactor 20 to be equipped with a flow control system that allows at least a portion of the liquid-phase feed stream to be introduced into reaction zone 28 at an elevated inlet superficial velocity of at least about 2 meters per second, more preferably at least about 5 meters per second, still more preferably at least about 6 meters per second, and most preferably in the range of from 8 to 20 meters per second. As used herein, the term "inlet superficial velocity" denotes the time-averaged volumetric flow rate of the feed stream out of the feed opening divided by the area of the feed opening. Preferably, at least about 50 weight percent of the feed stream is introduced into reaction zone 28 at an elevated inlet superficial velocity. Most preferably, substantially all the feed stream is introduced into reaction zone 28 at an elevated inlet superficial velocity.

Figure 6:
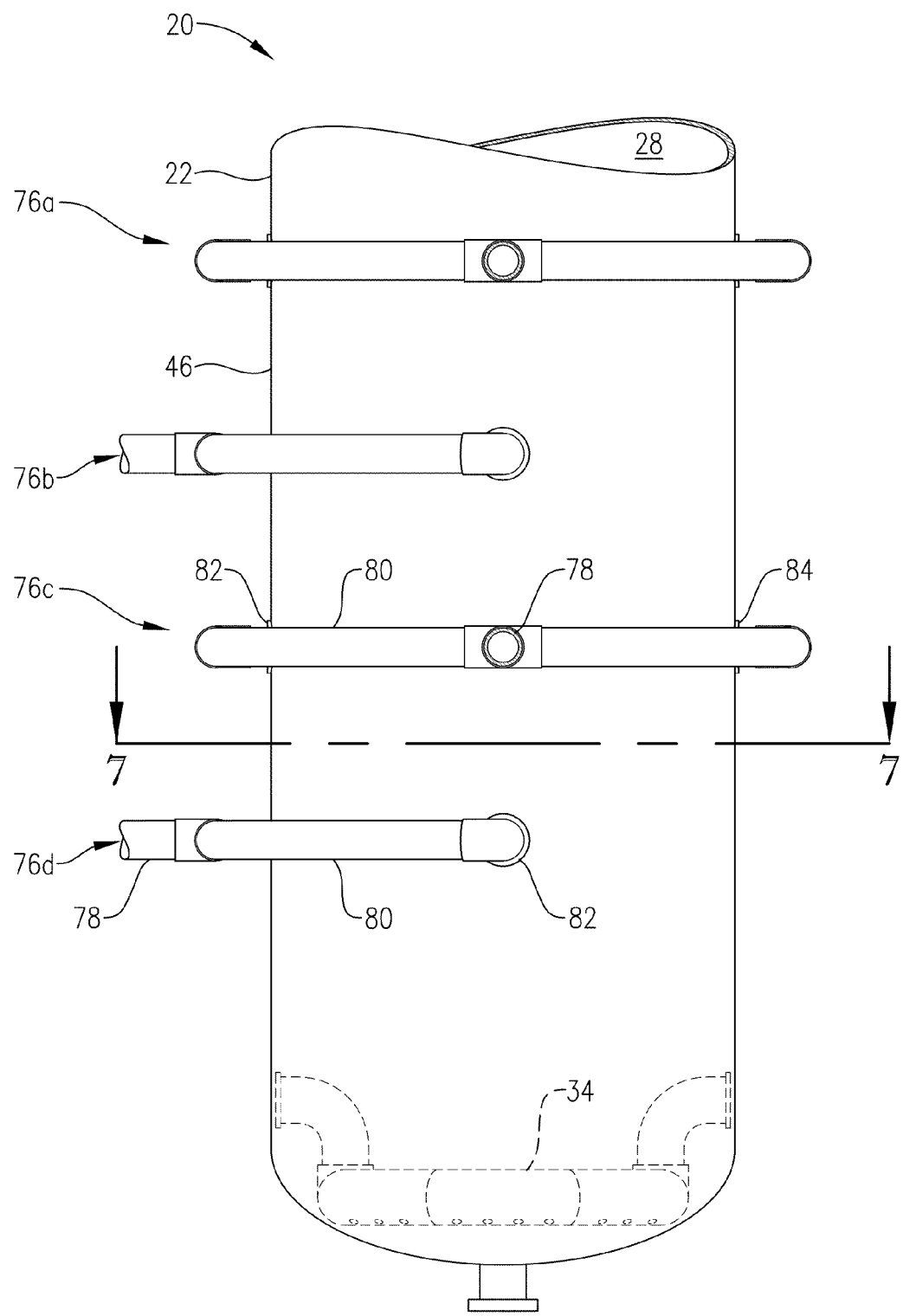
FIG. 6 is an enlarged side view of the bottom portion of the bubble column reactor, particular illustrating a system for introducing the feed stream into the reactor at multiple, vertically-space locations.
Figure 7:
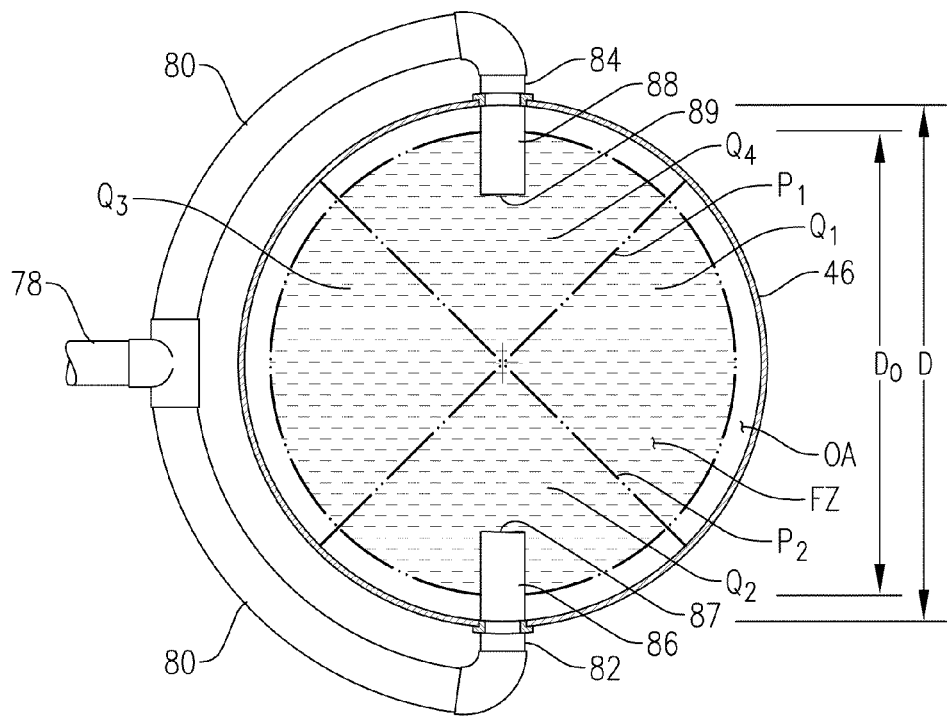
FIG. 7 is a sectional top view taken along line 7-7 in FIG. 6, particularly illustrating how the feed introduction system shown in FIG. 6 distributes the feed stream into in a preferred radial feed zone (FZ) and more than one azimuthal quadrant ($Q_1$, $Q_2$, $Q_3$, $Q_4$)

Referring now to FIGS. 6 and 7, an alternative system for introducing the liquid-phase feed stream into reaction zone 28 is illustrated. In this embodiment, the feed stream is introduced into reaction zone 28 at four different elevations. Each elevation is equipped with a respective feed distribution system 76a,b,c,d. Each feed distribution system 76 includes a main feed conduit 78 and a manifold 80. Each manifold 80 is provided with at least two outlets 82,84 coupled to respective insert conduits 86,88, which extend into reaction zone 28 of vessel shell 22. Each insert conduit 86,88 presents a respective feed opening 87,89 for discharging the feed stream into reaction zone 28. Feed openings 87,89 preferably have substantially similar diameters of less than about 7 centimeters, more preferably in the range of from about 0.25 to about 5 centimeters, and most preferably in the range of from 0.4 to 2 centimeters. It is preferred for feed openings 87,89 of each feed distribution system 76a,b,c,d to be diametrically opposed so as to introduce the feed stream into reaction zone 28 in opposite directions. Further, it is preferred for the diametrically opposed feed openings 86,88 of adjacent feed distribution systems 76 to be oriented at 90 degrees of rotation relative to one another. In operation, the liquid-phase feed stream is charged to main feed conduit 78 and subsequently enters manifold 80. Manifold 80 distributes the feed stream evenly for simultaneous introduction on opposite sides of reactor 20 via feed openings 87,89.

Figure 8:
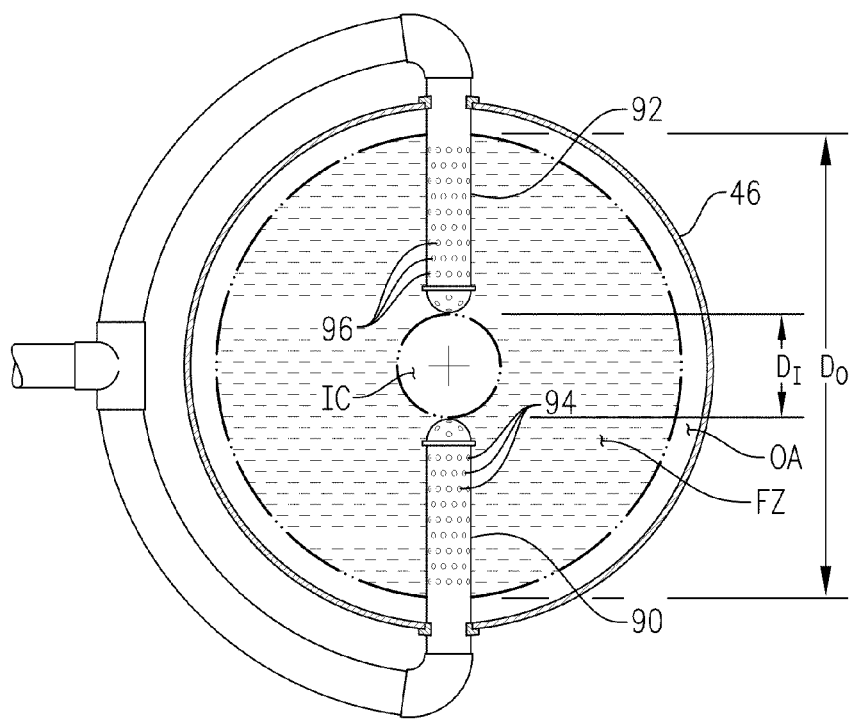
FIG. 8 is a sectional top view similar to FIG. 7, but illustrating an alternative means for discharging the feed stream into the reactor using bayonet tubes each having a plurality of small feed openings.

FIG. 8 illustrates an alternative configuration wherein each feed distribution system 76 is equipped with bayonet tubes 90,92 rather than insert conduits 86,88 (shown in FIG. 7). Bayonet tubes 90,92 project into reaction zone 28 and include a plurality of small feed openings 94,96 for discharging the liquid-phase feed into reaction zone 28. It is preferred for the small feed openings 94,96 of bayonet tubes 90,92 to have substantially the same diameters of less than about 50 millimeters, more preferably about 2 to about 25 millimeters, and most preferably 4 to 15 millimeters.

Figure 9:
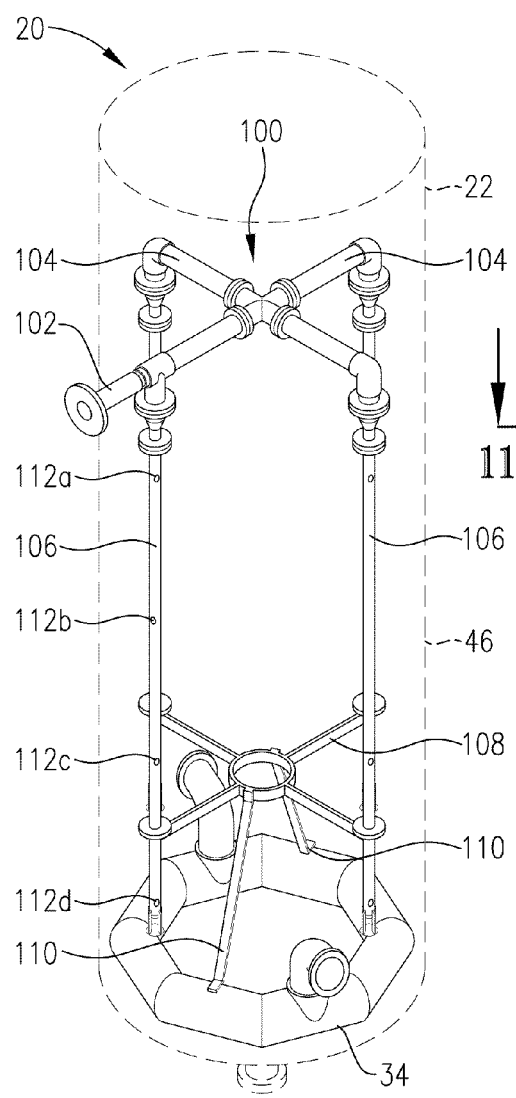
FIG. 9 is an isometric view of an alternative system for introducing the feed stream into the reaction zone at multiple vertically-space locations without requiring multiple vessel penetrations, particularly illustrating that the feed distribution system can be at least partly supported on the oxidant sparger.
Figure 11:
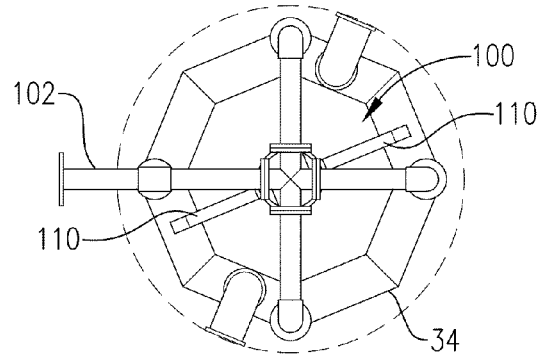
FIG. 11 is a sectional top view taken along line 11-11 in FIG. 10 and further illustrating the single-penetration feed distribution system supported on the oxidant sparger.
Figure 10:
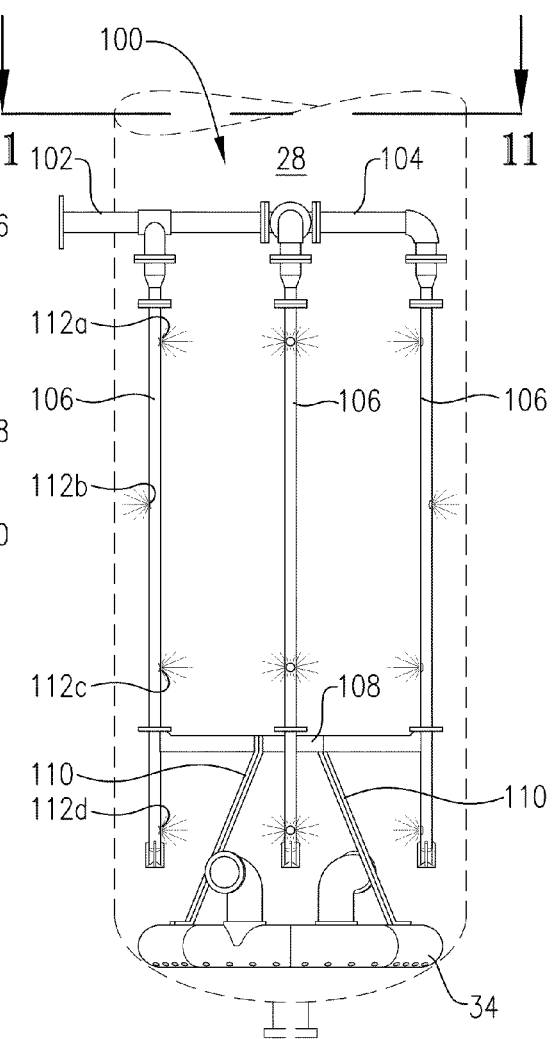
FIG. 10 is a side view of the single-penetration feed distribution system and oxidant sparger illustrated in FIG. 9.

FIGS. 9-11 illustrate an alternative feed distribution system 100. Feed distribution system 100 introduces the liquid-phase feed stream at a plurality of vertically-spaced and laterally-spaced locations without requiring multiple penetrations of the sidewall of bubble column reactor 20. Feed introduction system 100 generally includes a single inlet conduit 102, a header 104, a plurality of upright distribution tubes 106, a lateral support mechanism 108, and a vertical support mechanism 110. Inlet conduit 102 penetrates the sidewall of main body 46 of vessel shell 22. Inlet conduit 102 is fluidly coupled to header 104. Header 104 distributes the feed stream received from inlet conduit 102 evenly among upright distribution tubes 106. Each distribution tube 106 has a plurality of vertically-spaced feed openings 112a,b,c,d for discharging the feed stream into reaction zone 28. Lateral support mechanism 108 is coupled to each distribution tube 106 and inhibits relative lateral movement of distribution tubes 106. Vertical support mechanism 110 is preferably coupled to lateral support mechanism 108 and to the top of oxidant sparger 34. Vertical support mechanism 110 substantially inhibits vertical movement of distribution tubes 106 in reaction zone 28. It is preferred for feed openings 112 to have substantially the same diameters of less than about 50 millimeters, more preferably about 2 to about 25 millimeters, and most preferably 4 to 15 millimeters. The vertical spacing of feed openings 112 of feed distribution system 100 illustrated in FIGS. 9-11 can be substantially the same as described above with reference to the feed distribution system of FIG. 1. Optionally, feed openings can be elongated nozzles rather than simple holes. Optionally, one or more flow deflection apparatus can lie outside of the flow conduit and in path of fluids exiting therefrom into the reaction medium. Optionally, an opening near the bottom of a flow conduit can be sized to purge solids from inside the liquid-phase feed distribution system, either continuously or intermittently. Optionally, mechanical devices such as flapper assemblies, check valves, excess flow valves, power operated valves and the like may be used either to prevent ingress of solids during operational upsets or to discharge accumulated solids from within the liquid-phase feed distribution system.

It has been discovered that the flow patterns of the reaction medium in many bubble column reactors can permit uneven azimuthal distribution of the oxidizable compound in the reaction medium, especially when the oxidizable compound is primarily introduced along one side of the reaction medium. As used herein, the term "azimuthal" shall denote an angle or spacing around the upright axis of elongation of the reaction zone. As used herein, "upright" shall mean within 45° of vertical. In one embodiment of the present invention, the feed stream containing the oxidizable compound (e.g., para-xylene) is introduced into the reaction zone via a plurality of azimuthally-spaced feed openings. These azimuthally-spaced feed openings can help prevent regions of excessively high and excessively low oxidizable compound concentrations in the reaction medium. The various feed introduction systems illustrated in FIGS. 6-11 are examples of systems that provide proper azimuthal spacing of feed openings.

Referring again to FIG. 7, in order to quantify the azimuthally-spaced introduction of the liquid-phase feed stream into the reaction medium, the reaction medium can be theoretically partitioned into four upright azimuthal quadrants "$Q_1, Q_2, Q_3, Q_4$" of approximately equal volume. These azimuthal quadrants "$Q_1, Q_2, Q_3, Q_4$" are defined by a pair of imaginary intersecting perpendicular vertical planes "$P_1, P_2$" extending beyond the maximum vertical dimension and maximum radial dimension of the reaction medium. When the reaction medium is contained in a cylindrical vessel, the line of intersection of the imaginary intersecting vertical planes $P_1, P_2$ will be approximately coincident with the vertical centerline of the cylinder, and each azimuthal quadrant $Q_1, Q_2, Q_3, Q_4$ will be a generally wedge-shaped vertical volume having a height equal to the height of the reaction medium. It is preferred for a substantial portion of the oxidizable compound to be discharged into the reaction medium via feed openings located in at least two different azimuthal quadrants.

In a preferred embodiment of the present invention, not more than about 80 weight percent of the oxidizable compound is discharged into the reaction medium through feed openings that can be located in a single azimuthal quadrant. More preferably, not more than about 60 weight percent of the oxidizable compound is discharged into the reaction medium through feed openings that can be located in a single azimuthal quadrant. Most preferably, not more than 40 weight percent of the oxidizable compound is discharged into the reaction medium through feed openings that can be located in a single azimuthal quadrant. These parameters for azimuthal distribution of the oxidizable compound are measured when the azimuthal quadrants are azimuthally oriented such that the maximum possible amount of oxidizable compound is being discharged into one of the azimuthal quadrants. For example, if the entire feed stream is discharged into the reaction medium via two feed openings that are azimuthally spaced from one another by 89 degrees, for purposes of determining azimuthal distribution in four azimuthal quadrants, 100 weight percent of the feed stream is discharged into the reaction medium in a single azimuthal quadrant because the azimuthal quadrants can be azimuthally oriented in such a manner that both of the feed openings are located in a single azimuthal quadrant.

In addition to the advantages associated with the proper azimuthal-spacing of the feed openings, it has also been discovered that proper radial spacing of the feed openings in a bubble column reactor can also be important. It is preferred for a substantial portion of the oxidizable compound introduced into the reaction medium to be discharged via feed openings that are radially spaced inwardly from the sidewall of the vessel. Thus, in one embodiment of the present invention, a substantial portion of the oxidizable compound enters the reaction zone via feed openings located in a "preferred radial feed zone" that is spaced inwardly from the upright sidewalls defining the reaction zone.

Referring again to FIG. 7, the preferred radial feed zone "FZ" can take the shape of a theoretical upright cylinder centered in reaction zone 28 and having an outer diameter "$D_O$" of 0.9D, where "D" is the diameter of reaction zone 28. Thus, an outer annulus "OA" having a thickness of 0.05D is defined between the preferred radial feed zone FZ and the inside of the sidewall defining reaction zone 28. It is preferred for little or none of the oxidizable compound to be introduced into reaction zone 28 via feed openings located in this outer annulus OA.

In another embodiment, it is preferred for little or none of the oxidizable compound to be introduced into the center of reaction zone 28. Thus, as illustrated in FIG. 8, the preferred radial feed zone FZ can take the shape of a theoretical upright annulus centered in reaction zone 28, having an outer diameter $D_O$ of 0.9D, and having an inner diameter $D_I$ of 0.2D. Thus, in this embodiment, an inner cylinder IC having a diameter of 0.2D is "cut out" of the center of the preferred radial feed zone FZ. It is preferred for little or none of the oxidizable compound to be introduced into reaction zone 28 via feed openings located in this inner cylinder IC.

In a preferred embodiment of the present invention, a substantial portion of the oxidizable compound is introduced into reaction medium 36 via feed openings located in the preferred radial feed zone, regardless of whether the preferred radial feed zone has the cylindrical or annular shape described above. More preferably, at least about 25 weight percent of the oxidizable compound is discharged into reaction medium 36 via feed openings located in the preferred radial feed zone. Still more preferably, at least about 50 weight percent of the oxidizable compound is discharged into reaction medium 36 via feed openings located in the preferred radial feed zone. Most preferably, at least 75 weight percent of the oxidizable compound is discharged into reaction medium 36 via feed openings located in the preferred radial feed zone.

Although the theoretical azimuthal quadrants and theoretical preferred radial feed zone illustrated in FIGS. 7 and 8 are described with reference to the distribution of the liquid-phase feed stream, it has been discovered that proper azimuthal and radial distribution of the gas-phase oxidant stream can also provide certain advantages. Thus, in one embodiment of the present invention, the description of the azimuthal and radial distribution of the liquid-phase feed stream, provided above, also applies to the manner in which the gas-phase oxidant stream is introduced into the reaction medium 36.

Figure 12:
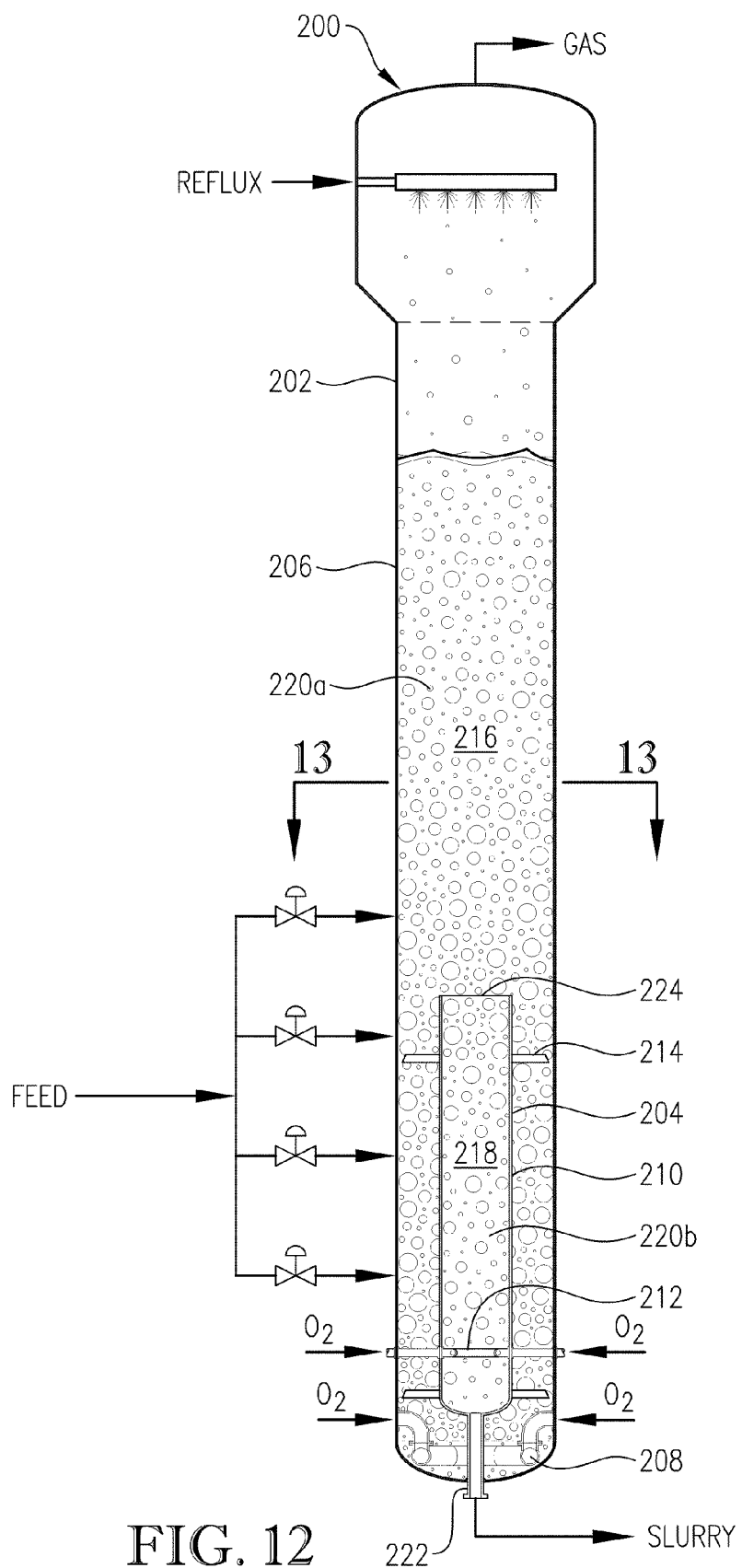
FIG. 12 is a side view of a bubble column reactor equipped with internal and external reaction vessels.
Figure 13:
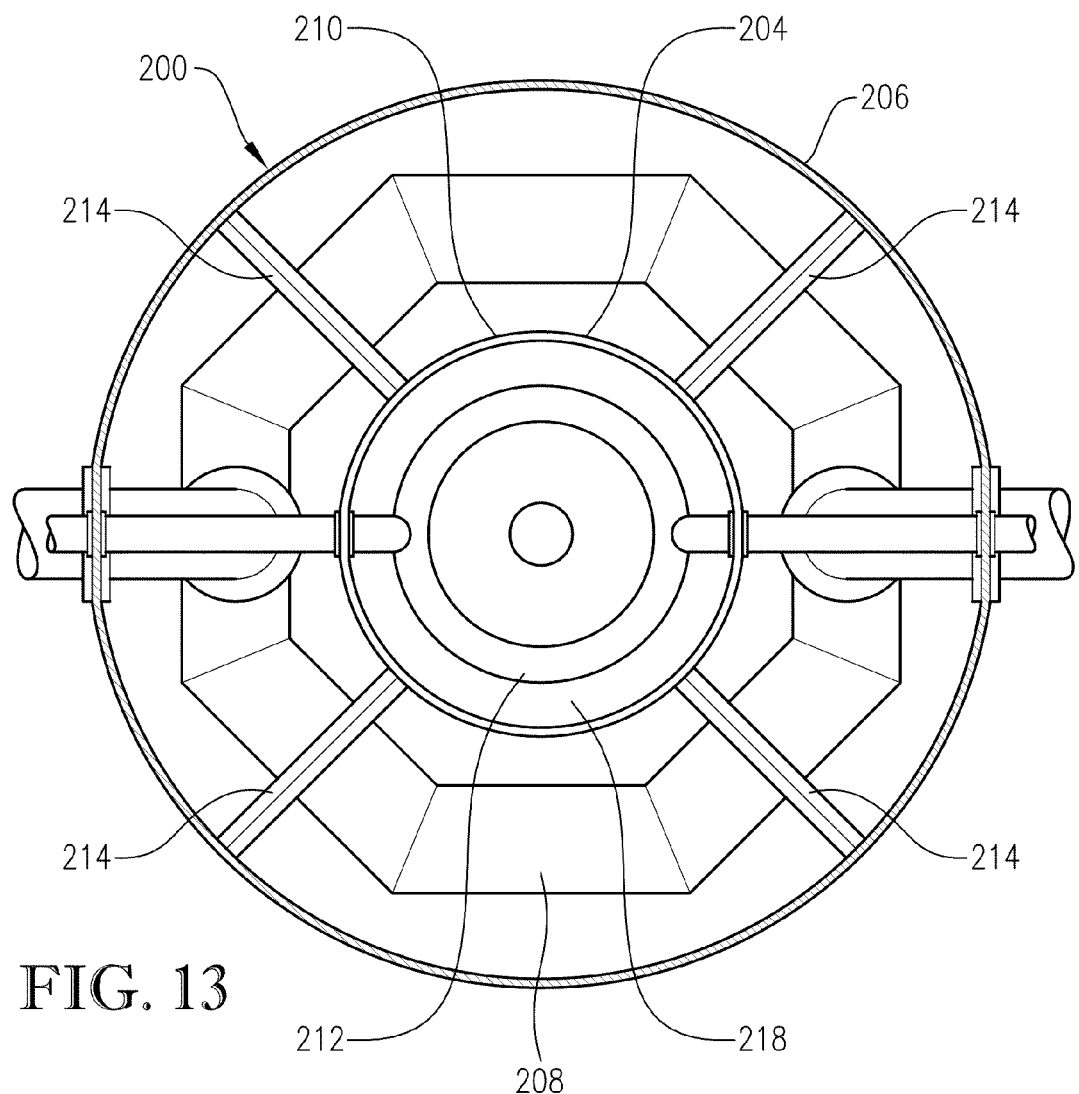
FIG. 13 is an enlarged sectional view of the bubble column reactor of FIG. 12 taken along line 13-13, particularly illustrating the relative orientation of the internal and external reaction vessels.

Referring now to FIGS. 12 and 13, there is illustrated an alternative bubble column reactor 200 having a reactor-in-reactor configuration. Bubble column reactor 200 includes an external reactor 202 and an internal reactor 204, with internal reactor 204 being at least partly disposed in external reactor 202. In a preferred embodiment, both external and internal reactors 202 and 204 are bubble column reactors. Preferably, external reactor 202 includes an external reaction vessel 206 and an external oxidant sparger 208, while internal reactor 204 includes an internal reaction vessel 210 and an internal oxidant sparger 212.

Although FIGS. 12 and 13 illustrate internal reaction vessel 210 as being fully disposed in external reaction vessel 206, it is possible for internal reaction vessel 210 to be only partial disposed in external reaction vessel 206. However, it is preferred for at least about 50, 90, 95, or 100 percent of the height of internal reaction vessel 210 to be located in external reaction vessel 206. Furthermore, it is preferred that a portion of each reaction vessel is elevated above a portion of the other reaction vessel by at least about 0.01, 0.2, 1, or 2 times the maximum diameter of the external reaction vessel.

In a preferred embodiment of the present invention, external and internal reaction vessels 206 and 210 each include a respective upright sidewall having a generally cylindrical configuration. Preferably, the upright sidewalls of external and internal reaction vessels 206 and 210 are substantially concentric and define an annulus therebetween. Internal reaction vessel 210 is supported vertically from external reaction vessel 206, preferably principally by upright supports between the lower portions of the respective vessels. In addition, internal reaction vessel 210 can be supported by external reaction vessel 206 via a plurality of lateral support members 214 extending between the upright sidewall of external and internal reaction vessels 206 and 210. Preferably, such lateral support members 214 have a non-fouling configuration with minimal upwardly-facing planar surface, as previously defined.

Although it is preferred for the upright sidewall of internal reaction vessel 210 to be substantially cylindrical, it is possible for certain portions of the upright sidewall of internal reaction vessel 210 to be concave with respect to an adjacent portion of second reaction zone 218. Preferably, any portion of the upright sidewall of internal reaction vessel 210 that is concave with respect to an adjacent portion of second reaction zone 218 accounts for less than about 25, 10, 5, or 0.1 percent of the total surface area of the upright sidewall of internal reaction vessel 210. Preferably, the ratio of the maximum height of the upright sidewall of internal reaction vessel 210 to the maximum height of the upright sidewall of external reaction vessel 206 is in the range of from about 0.1:1 to about 0.9:1, more preferably in the range of from about 0.2:1 to about 0.8:1, and most preferably in the range of from 0.3:1 to 0.7:1.

External reaction vessel 206 defines therein a first reaction zone 216, while internal reaction vessel 210 defines therein a second reaction zone 218. Preferably, external and internal reaction vessels 206 and 210 are aligned vertically such that the volumetric centroid of second reaction zone 218 is horizontally displaced from the volumetric centroid of first reaction zone 216 by less than about 0.4, 0.2, 0.1, or 0.01 times the maximum horizontal diameter of first reaction zone 216. Preferably, the ratio of the maximum horizontal cross sectional area of first reaction zone 216 to second reaction zone 218 is in the range of from about 0.01:1 to about 0.75:1, more preferably in the range of from about 0.03:1 to about 0.5:1, and most preferably in the range of from 0.05:1 to 0.3:1. Preferably, the ratio of the horizontal cross sectional area of second reaction zone 218 to the horizontal cross sectional area of the annulus defined between external and internal reaction vessels 206 and 210 is at least about 0.02:1, more preferably in the range of from about 0.05:1 to about 2:1, and most preferably in the range of from about 0.1:1 to about 1:1, where the cross sectional area is measured at ¼-height, ½-height, and/or ¾-height of second reaction zone 218. Preferably, at least about 50, 70, 90, or 100 percent of the volume of second reaction zone 218 is located in external reaction vessel 206. Preferably, the ratio of the volume of first reaction zone 216 to the volume of second reaction zone 218 is in the range of from about 1:1 to about 100:1, more preferably in the range of from about 4:1 to about 50:1, and most preferably in the range of from 8:1 to 30:1. Preferably, first reaction zone 216 has a ratio of maximum vertical height to maximum horizontal diameter in the range of from about 3:1 to about 30:1, more preferably about 6:1 to about 20:1, and most preferably in the range of from 9:1 to 15:1. Preferably, second reaction zone 218 has a ratio of maximum vertical height to maximum horizontal diameter in the range of from about 0.3:1 to about 100:1, more preferably in the range of from about 1:1 to about 50:1, and most preferably in the range of from 3:1 to 30:1. Preferably, the maximum horizontal diameter of second reaction zone 218 is in the range of from about 0.1 to about 5 meters, more preferably in the range of from about 0.3 to about 4 meters, and most preferably in the range of from 1 to 3 meters. Preferably, the maximum vertical height of second reaction zone 218 is in the range of from about 1 to about 100 meters, more preferably in the range of from about 3 to about 50 meters, and most preferably in the range of from 10 to 30 meters. Preferably, the ratio of the maximum horizontal diameter of second reaction zone 218 to the maximum horizontal diameter of first reaction zone 216 is in the range of from about 0.05:1 to about 0.8:1, more preferably in the range of from about 0.1:1 to about 0.6:1, and most preferably in the range of 0.2:1 to 0.5:1. Preferably, the ratio of the maximum vertical height of second reaction zone 218 to the maximum vertical height of first reaction zone 216 is in the range of from about 0.03:1 to about 1:1, more preferably in the range of from about 0.1:1 to about 0.9:1, and most preferably in the range of from 0.3:1 to 0.8:1. Any parameters (e.g., height, width, area, volume, relative horizontal placement, and relative vertical placement) specified herein for external reaction vessel 206 and appurtenances are also construed as applying to first reaction zone 216 defined by external reaction vessel 206, and vice versa. Further, any parameters specified herein for internal reaction vessel 210 and appurtenances are also construed as applying to second reaction zone 218 defined by internal reaction vessel 210, and vice versa.

During operation of bubble column reactor 200, a multiphase reaction medium 220 is first subjected to oxidation in first reaction zone 216 and then subjected to oxidation in second reaction zone 218. Thus, during normal operation, a first portion of reaction medium 220a is located in first reaction zone 216, while a second portion of reaction medium 220b is located in second reaction zone 218. After being processed in second reaction zone 218, a slurry phase (i.e., liquid and solid phases) of reaction medium 220b is withdrawn from second reaction zone 218 and discharged from bubble column reactor 200 via a slurry outlet 222 for subsequent downstream processing.

Internal reactor 204 preferably comprises at least one internal gas opening that permits additional molecular oxygen to be discharged into second reaction zone 218. Preferably, a plurality of internal gas openings are defined by internal oxidant sparger 212. The disclosures for oxidant sparger 34 of FIGS. 1-5 also apply to internal oxidant sparger 212 for conduit sizes and configurations, opening sizing and configuration, operating pressure drop, and liquid flushing. In notable distinction, it is preferable to locate oxidant sparger 212 relatively higher in order to use a lower portion of internal reaction vessel 210 as a deaeration zone. For example, embodiments disclosed herein for oxidation of para-xylene to form TPA provide a greatly diminished space time reaction rate near the bottom of second reaction zone 218, and this mitigates the effects of deaeration on impurity formation. Internal reaction vessel 210 has a maximum height "$H_i$". It is preferred for at least about 50, 75, 95, or 100 percent of the total open area defined by all of the internal gas openings to be spaced at least $0.05H_i$, $0.1H_i$, or $0.25H_i$ from the top of internal reaction vessel 210. It is also preferred for at least about 50, 75, 95, or 100 percent of the total open area defined by all of the internal gas openings to be spaced less than about $0.5H_i$, $0.25H_i$, or $0.1H_i$ above the bottom of internal reaction vessel 210. Preferably, at least about 50, 75, 95, or 100 percent of the total open area defined by all of the internal gas openings are spaced at least about 1, 5, or 10 meters from the top of internal reaction vessel 210 and at least about 0.5, 1, or 2 meters from the bottom of internal reaction vessel 210. It is preferred for at least about 50, 75, 95, or 100 percent of the total open area defined by all of the internal gas openings to communicate directly with second reaction zone 218 and not communicate directly with first reaction zone 216. As used herein, the term "open area" denotes the minimum surface area (planar or nonplanar) that would close off an opening.

In general, the manner in which the feed, oxidant, and reflux streams are introduced into external reactor 202 and the manner in which external reactor 202 is operated are substantially the same as described above with reference to bubble column reactor 20 of FIGS. 1-11. However, one difference between external reactor 202 (FIGS. 12 and 13) and bubble column reactor 20 (FIGS. 1-11) is that external reactor 202 does not include an outlet that permits the slurry phase of reaction medium 220$a$ to be directly discharged from external reaction vessel 206 for downstream processing. Rather, bubble column reactor 200 requires the slurry phase of reaction medium 220$a$ to first pass through internal reactor 204 before being discharged from bubble column reactor 200. As mentioned above, in second reaction zone 218 of internal reactor 204, reaction medium 220$b$ is subjected to further oxidation to help purify the liquid and/or solid phases of reaction medium 220$b$.

In a process wherein para-xylene is fed to reaction zone 216, the liquid phase of reaction medium 220$a$ that exits first reaction zone 216 and enters second reaction zone 218 typically contains at least some para-toluic acid. It is preferred for a substantial portion of the para-toluic acid entering second reaction zone 218 to be oxidized in second reaction zone 218. Thus, it is preferred for the time-averaged concentration of para-toluic acid in the liquid phase of reaction medium 220$b$ exiting second reaction zone 218 to be less than the time-averaged concentration of para-toluic acid in the liquid phase of reaction medium 220$a/b$ entering second reaction zone 218. Preferably, the time-averaged concentration of para-toluic acid in the liquid phase of reaction medium 220$b$ exiting second reaction zone 218 is less than about 50, 10, or 5 percent of the time-averaged concentration of para-toluic acid in the liquid phase of reaction medium 220$a/b$ entering second reaction zone 218. Preferably, the time-averaged concentration of para-toluic acid in the liquid phase of reaction medium 220$a/b$ entering second reaction zone 218 is at least about 250 ppmw, more preferably in the range of from about 500 to about 6,000 ppmw, and most preferably in the range of from 1,000 to 4,000 ppmw. Preferably, the time-averaged concentration of para-toluic acid in the liquid phase of reaction medium 220$b$ exiting second reaction zone 218 is less than about 1,000, 250, or 50 ppmw.

Internal reaction vessel 210 is equipped with at least one direct opening that permits reaction medium 220$a/b$ to pass directly between reaction zone 216 and second reaction zone 218. It is preferred for substantially all of the direct openings in internal reaction vessel 210 to be located near the top of internal reaction vessel 210. Preferably, at least about 50, 75, 90, or 100 percent of the total open area defined by all of the direct openings is spaced less than about 0.5H$_i$, 0.25H$_i$ or 0.1H$_i$ from the top of internal reaction vessel 210. Preferably, less than about 50, 25, 10, or 1 percent of the total open area defined by the direct openings in internal reaction vessel 210 is spaced more than about 0.5H$_i$, 0.25H$_i$ or 0.1H$_i$ from the top of internal reaction vessel 210. Most preferably, the direct opening defined by internal reaction vessel 210 is a single upper opening 224 located at the upper-most end of internal reaction vessel 210. The ratio of the open area of upper opening 224 to the maximum horizontal cross sectional area of second reaction zone 218 is preferably at least about 0.1:1, 0.2:1, or 0.5:1.

During normal operation of bubble column reactor 200, reaction medium 220 passes from first reaction zone 216, through the direct opening(s) (e.g., upper opening 224) in internal reaction vessel 210, and into second reaction zone 218. In second reaction zone 218, the slurry phase of reaction medium 220$b$ travels in a generally downward direction through second reaction zone 218, while the gas phase of reaction medium 220$b$ travels in a generally upward direction. Preferably, internal reaction vessel 210 defines at least one discharge opening that permits the slurry phase to exit second reaction zone 218. The slurry phase exiting the discharge opening of internal reaction vessel 210 then exits bubble column reactor 200 via slurry outlet 222. Preferably, discharge opening is located at or near the bottom of internal reaction vessel 210. Preferably at least about 50, 75, 90, or 100 percent of the total open area defined by all discharge openings in internal reaction vessel 210 is located within about 0.5H$_i$, 0.25H$_i$ or 0.1H$_i$ of the bottom of internal reaction vessel 210.

As reaction medium 220$b$ is processed in second reaction zone 218 of internal reactor 204, it is preferred for the gas hold-up of reaction medium 220$b$ to decrease as the slurry phase of reaction medium 220$b$ flows downwardly through second reaction zone 218. Preferably, the ratio of the time-averaged gas hold-up of reaction medium 220$a/b$ entering second reaction zone 218 to reaction medium 220$b$ exiting second reaction zone 218 is at least about 2:1, 10:1, or 25:1. Preferably, the time-averaged gas hold-up of reaction medium 220$a/b$ entering second reaction zone 218 is in the range of from about 0.4 to about 0.9, more preferably in the range of from about 0.5 to about 0.8, and most preferably in the range of from 0.55 to 0.7. Preferably, the time-averaged gas hold-up of reaction medium 220$b$ exiting second reaction zone 218 is less than about 0.1, 0.05, or 0.02. Preferably, the ratio of the time-averaged gas hold-up of reaction medium 220$a$ in first reaction zone 216 to reaction medium 220$b$ in second reaction zone 218 is greater than about 1:1, more preferably in the range of from about 1.25:1 to about 5:1, and most preferably in the range of from 1.5:1 to 4:1, where the gas hold-up values are measured at any height of first and second reaction zones 216 and 218, at any corresponding heights of first and second reaction zones 216 and 218, at ¼-height of first and/or second reaction zones 216 and 218, at ½-height of first and/or second reaction zones 216 and 218, at ¾-height of first and/or second reaction zones 216 and 218, and/or are average values over the entire heights of first and/or second reaction zones 216 and 218. Preferably, the time-averaged gas hold-up of the portion of reaction medium 220$a$ in first reaction zone 216 is in the range of from about 0.4 to about 0.9, more preferably in the range of from about 0.5 to about 0.8, and most preferably in the range of from 0.55 to 0.70, where the gas hold-up is measured at any height of first reaction zone 216, at ¼-height of first reaction zone 216, at ½-height of first reaction zone 216, at ¾-height of first reaction zone 216, and/or is an average over the entire height of first reaction zone 216. Preferably, the time-averaged gas hold-up of the portion of reaction medium 220$b$ in second reaction zone 218 is in the range of from about 0.01 to about 0.6, more preferably in the range of from about 0.03 to about 0.3, and most preferably in the range of from 0.08 to 0.2, where the gas hold-up is measured at any height of second reaction zone 218, at ¼-height of second reaction zone 218, and ½-height of second reaction zone 218, at ¾-height of second reaction zone 218, and/or is an average over the entire height of second reaction zone 218.

The temperature of reaction medium 220 is preferably approximately the same in first and second reaction zones 216 and 218. Preferably, such temperature is in the range of from about 125 to about 200° C., more preferably in the range of from about 140 to about 180° C., and most preferably in the range of from 150 to 170° C. However, temperature differences preferably are formed within first reaction zone 216 that are the same as disclosed herein with reference to FIG. 28. Preferably, temperature differences of the same magnitudes also exist within second reaction zone 218 and also between first reaction zone 216 and second reaction zone 218. These additional temperature gradients relate to chemical reaction occurring in second reaction zone 218, the introduction additional oxidant to second reaction zone 218, and the static pressures extant in second reaction zone 218 compared to those in first reaction zone 216. As disclosed above, the bubble hold-up is preferably greater in first reaction zone 216 than in second reaction zone 218. Thus, at elevations below upper opening 224, the static pressure in reaction zone 216 is greater than in second reaction zone 218. The magnitude of this pressure difference depends on the magnitude of liquid or slurry density and on the difference in bubble hold-up between the two reaction zones. The magnitude of this pressure difference increases at elevations further below upper opening 224.

In one embodiment of the present invention, a portion of the oxidizable compound (e.g., para-xylene) fed to bubble column reactor 200 is introduced directly into second reaction zone 218 of internal reactor 204. However, it is preferred for at least about 90, 95, 99, or 100 mole percent of the total oxidizable compound fed to bubble column reactor 200 to be introduced into first reaction zone 216 (rather than second reaction zone 218). Preferably, the molar ratio of the amount of oxidizable compound introduced into first reaction zone 216 to the amount of oxidizable compound introduced into second reaction zone 218 is at least about 2:1, 4:1, or 8:1.

Although FIGS. 12 and 13 depict a configuration where a portion of the total molecular oxygen fed to bubble column reactor 200 is introduced into second reaction zone 218 of internal reactor 204 via internal oxidant sparger 212, it is preferred for the majority of the total molecular oxygen fed to bubble column reactor 200 to be introduced into first reaction zone 216, with the balance being introduced into the second reaction zone 218. Preferably, at least about 70, 90, 95, or 98 mole percent of the total molecular oxygen fed to bubble column reactor 200 is introduced into first reaction zone 216. Preferably, the molar ratio of the amount of molecular oxygen introduced into first reaction zone 216 to the amount of molecular oxygen introduced into second reaction zone 218 is at least about 2:1, more preferably in the range of from about 4:1 to about 200:1, most preferably in the range of from 10:1 to 100:1. Although it is possible for some of the solvent and/or oxidizable compound (e.g., para-xylene) to be fed directly to second reaction zone 218, it is preferred for less than about 10, 5, or 1 weight percent of the total amount of solvent and/or oxidizable compound fed to bubble column reactor 200 to be fed directly to second reaction zone 218.

The volume, residence time, and space time rate of medium 220a in first reaction zone 216 of external reaction vessel 206 are preferably substantially greater than the volume, residence time, and space time rate of reaction medium 220b in second reaction zone 218 of internal reaction vessel 210. Therefore, the majority of the oxidizable compound (e.g., para-xylene) fed to bubble column reactor 200 is preferably oxidized in first reaction zone 216. Preferably, at least about 80, 90, or 95 weight percent of all the oxidizable compound that is oxidized in bubble column reactor 200 is oxidized in first reaction zone 216. It is preferred for the time-averaged superficial gas velocity of reaction medium 220a in first reaction zone 216 to be at least about 0.2, 0.4, 0.8, or 1 meters per second, where the superficial gas velocity is measured at any height of first reaction zone 216, at ¼-height of first reaction zone 216, at ½-height of first reaction zone 216, at ¾-height of first reaction zone 216, and/or is an average over the entire height of first reaction zone 216.

Although reaction medium 220b in second reaction zone 218 can have the same superficial gas velocity as reaction medium 220a in first reaction zone 216, it is preferred that the time-averaged superficial gas velocity of reaction medium 220b in second reaction zone 218 is less than the time-averaged and volume-averaged superficial gas velocity of reaction medium 220b in second reaction zone 218. This reduced superficial gas velocity in second reaction zone 218 is made possible by, for example, the reduced demand for molecular oxygen in second reaction zone 218 compared to first reaction zone 216. Preferably, the ratio of the time-averaged superficial gas velocity of reaction medium 220a in first reaction zone 216 to reaction medium 220b in second reaction zone 218 is at least about 1.25:1, 2:1, or 5:1, where the superficial gas velocities are measured at any height of first and second reaction zones 216 and 218, at any corresponding heights of first and second reaction zones 216 and 218, at ¼-height of first and/or second reaction zones 216 and 218, at ½-height of first and/or second reaction zones 216 and 218, at ¾-height of first and/or second reaction zones 216 and 218, and/or are average values over the entire heights of first and/or second reaction zones 216 and 218. Preferably, the time-averaged and volume-averaged superficial gas velocity of reaction medium 220b in second reaction zone 218 is less than about 0.2, 0.1, or 0.06 meters per second, where the superficial gas velocity is measured at any height of second reaction zone 218, at ¼-height of second reaction zone 218, at ½-height of second reaction zone 218, at ¾-height of second reaction zone 218, and/or is an average over the entire height of second reaction zone 218. With these lower superficial gas velocities, downward flow of the slurry phase of reaction medium 220b in second reaction zone 218 can be made to move directionally toward plug flow. For example, during oxidation of para-xylene to form TPA, the relative vertical gradient of liquid phase concentration of para-toluic acid can be much greater in second reaction zone 218 than in first reaction zone 216. This is notwithstanding that second reaction zone 218 is a bubble column having axial mixing of liquid and of slurry compositions. The time-averaged superficial velocity of the slurry phase (solid+liquid) and the liquid phase of reaction medium 220b in second reaction zone 218 are preferably less than about 0.2, 0.1, or 0.06 meters per second, where the superficial velocity is measured at any height of second reaction zone 218, at ¼-height of second reaction zone 218, at ½-height of second reaction zone 218, at ¾-height of second reaction zone 218, and/or is an average over the entire height of second reaction zone 218.

In one embodiment of the present invention, bubble column reactor 200 is operated in a manner that permits solids sedimentation in internal reactor 204. If solids sedimentation is desired, it is preferred for the time-averaged and volume-averaged superficial gas velocity of reaction medium 220b in second reaction zone 218 to be less than about 0.05, 0.03, or 0.01 meters per second.

Further, if solids sedimentation is desired, it is preferred for the time-averaged and volume-averaged superficial velocity of the slurry and liquid phases of reaction medium 220b in second reaction zone 218 to be less than about 0.01, 0.005, or 0.001 meters per second.

While it is possible for some of the slurry phase exiting internal reactor 204 to be directly recirculated back to first reaction zone 216 without further downstream processing, it is preferred for direct recirculation of reaction medium 220b from the lower elevations of second reaction zone 218 to first reaction zone 216 to be minimized Preferably, the mass of reaction medium 220b (solid, liquid, and gas phases) exiting the lower 25 percent of the volume of second reaction zone 218 and directly recirculated back to first reaction zone 216 without further downstream processing is less than 10, 1, or 0.1 times the mass (solid, liquid, and gas phases) of reaction medium 220b exiting second reaction zone 218 and thereafter subjected to downstream processing. Preferably, the mass of reaction medium 220b exiting the lower 50 percent of the volume of second reaction zone 218 and directly recirculated back to first reaction zone 216 without further downstream processing is less than 20, 2, or 0.2 times the mass of reaction medium 220b exiting second reaction zone 218 and thereafter subjected to downstream processing. Preferably, less than about 50, 75, or 90 weight percent of the liquid phase of reaction medium 220b exiting second reaction zone 218 via openings in the lower 90, 60, 50, or 5 percent of the volume of second reaction zone 218 is introduced into first reaction zone 216 within 60, 20, 5, or 1 minutes after exiting second reaction zone 218. Preferably, the liquid phase of reaction medium 220b located in second reaction zone 218 has a mass-averaged residence time in second reaction zone 218 of at least about 1 minute, more preferably in the range of from about 2 to about 60 minutes, and most preferably in the range of from 5 to 30 minutes. Preferably, less than about 50, 75, or 90 weight percent of the liquid phase of reaction medium 220a/b introduced into second reaction zone 218 enters second reaction zone 218 in the lower 90, 60, or 30 percent of the volume of second reaction zone 218. Preferably, less than about 50, 75, or 90 weight percent of the total liquid phase of reaction medium 220a/b introduced as a liquid-phase feed stream into first reaction zone 216 enters first reaction zone 216 within 60, 20, 5, or 1 minutes after being withdrawn from second reaction zone 218 via slurry outlet 222. Preferably, at least about 75, 90, 95, or 99 weight percent of the liquid phase of reaction medium 220b withdrawn from second reaction zone 218 exits second reaction zone 218 via openings in the lower 90, 60, 30, or 5 percent of the volume of second reaction zone 218.

The design of reactor-in-reactor bubble column reactor 200 can be varied in many ways without departing from the ambit of the present invention. For example, internal reaction vessel 210 can have a greater height than external reaction vessel 206 if internal reaction vessel 210 extends below the lower end of external reaction vessel 206. External and internal reaction vessels 206 and 210 can be cylindrical, as illustrated, or can have another shape. External and internal reaction vessels 206 and 210 need not be axisymmetric, axially vertical, or concentric. The gas phase exiting internal reactor 204 can be routed outside bubble column reactor 200 without being commingled with reaction medium 220a in first reaction zone 216. However, for flammability safety, it is desirable to limit volumes of trapped gas pockets to less than about 10, 2, or 1 cubic meters. In addition, the slurry phase exiting internal reactor 204 need not exit via a single slurry opening in the bottom of internal reaction vessel 210. The slurry phase can exit bubble column reactor 200 though a side outlet in a pressure containing sidewall of external reactor 202.

Figure 14:
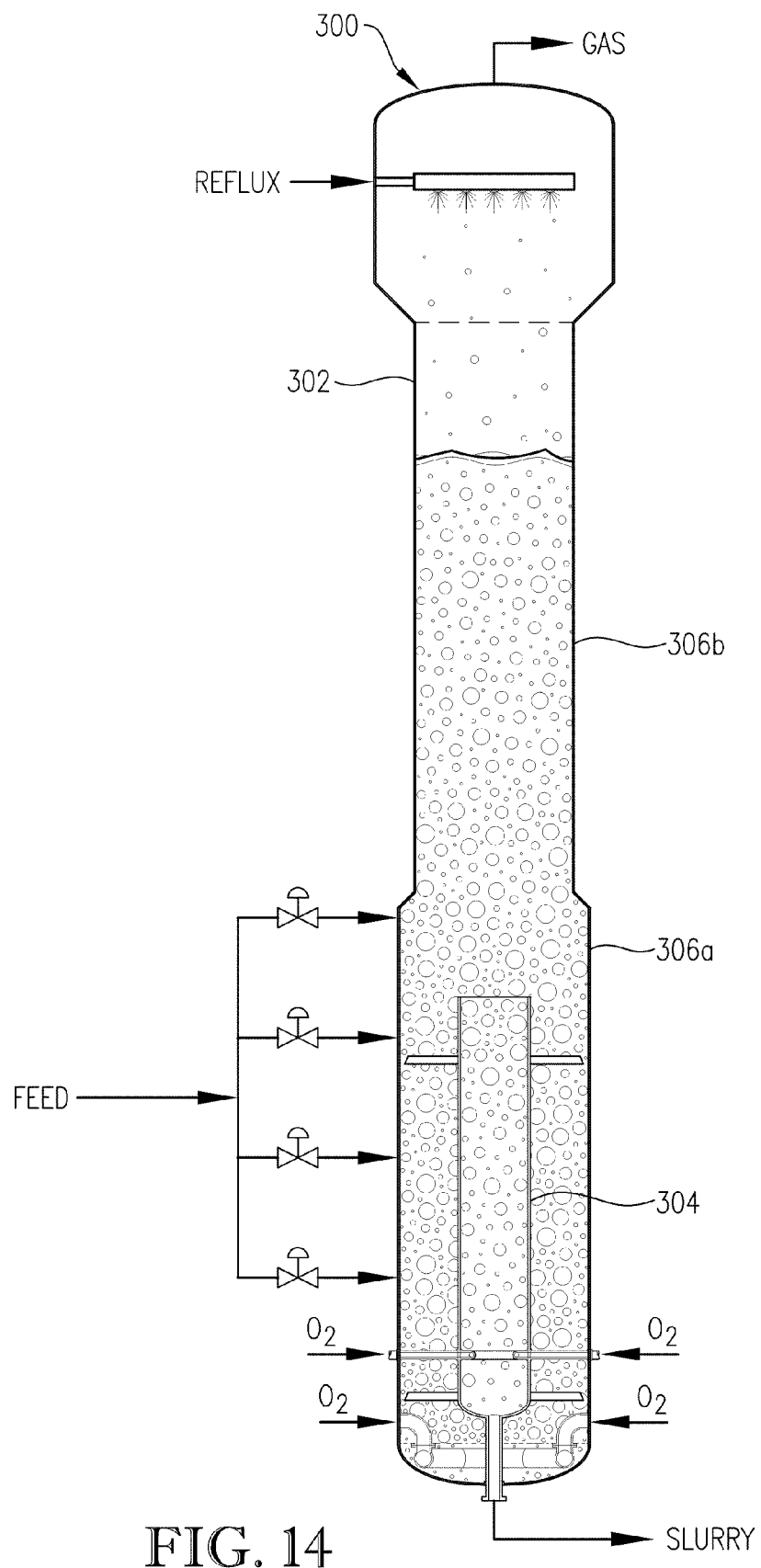
FIG. 14 is a side view of an alternative bubble column reactor equipped with internal and external reaction vessels, particularly illustrating that the external reaction vessel has a stepped diameter.

Referring now to FIG. 14, there is illustrated a bubble column reactor 300 having a reactor-in-reactor and staged-diameter configuration. Bubble column reactor 300 comprises an external reactor 302 and an internal reactor 304. External reactor 302 includes an external reaction vessel 306 having a broad lower section 306a and a narrow upper section 306b. Preferably, the diameter of narrow upper section 306b is smaller than the diameter of broad lower section 306a. With the exception of the staged-diameter configuration of the external reaction vessel, bubble column reactor 300 of FIG. 14 is preferably configured and operated in substantially the same manner as bubble column reactor 200 of FIGS. 12 and 13, described above.

Figure 15:
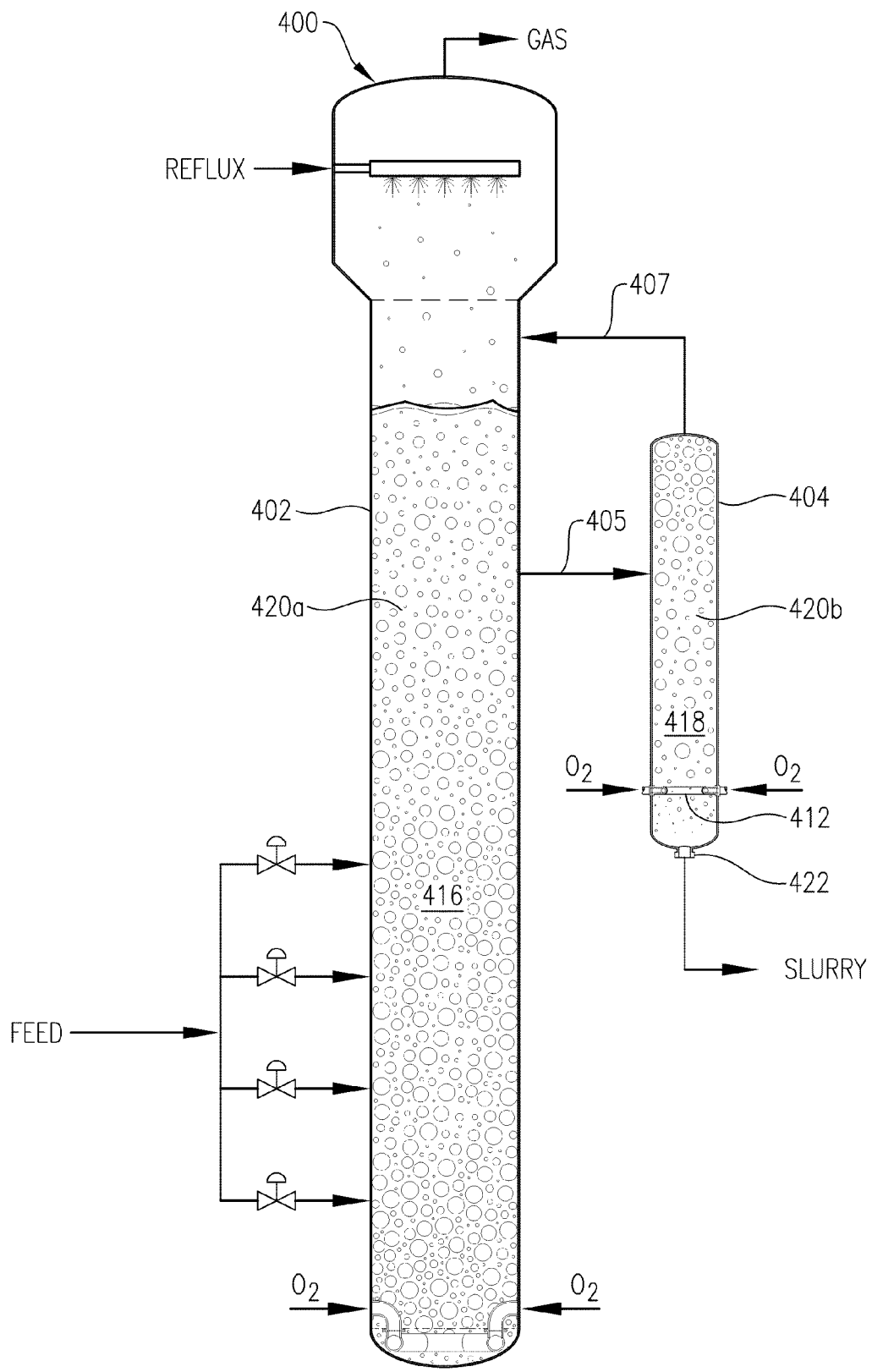
FIG. 15 is a side view of a bubble column reactor equipped with an external secondary oxidation reactor that receives a slurry from a sidedraw in the primary oxidation reactor.

Referring now to FIG. 15, there is illustrated a reactor system 400 comprising a primary oxidation reactor 402 and a secondary oxidation reactor 404. Primary oxidation reactor 402 is preferably configured and operated in substantially the same manner as external reactor 202 of FIGS. 12 and 13.

Secondary oxidation reactor 404 is preferably configured and operated in substantially the same manner as internal reactor 204 of FIGS. 12 and 13. However, the main difference between reactor system 400 of FIG. 15 and bubble column reactor 200 of FIGS. 12 and 13 is that secondary oxidation reactor 404 of reactor system 400 is located outside of primary oxidation reactor 402. In reaction system 400 of FIG. 15, an inlet conduit 405 is employed to transfer a portion of the reaction medium 420 from primary oxidation reactor 402 to secondary oxidation reactor 404. Further, an outlet conduit 407 is used to transfer overhead gasses from the top of secondary oxidation reactor 404 to primary oxidation reactor 402.

During normal operation of reaction system 400, reaction medium 420 first undergoes oxidation in a primary reaction zone 416 of primary oxidation reactor 402. Reaction medium 420a is then withdrawn from primary reaction zone 416 and transferred to a secondary reaction zone 418 via conduit 405. In secondary reaction zone 418, the liquid and/or solid phases of reaction medium 420b are subjected to further oxidation. It is preferred for at least about 50, 75, 95, or 99 weight percent of liquid and/or solid phases withdrawn from primary reaction zone 416 to be processed in secondary reaction zone 416. Overhead gasses exit an upper gas outlet of secondary oxidation reactor 404 and are transferred back to primary oxidation reactor 402 via conduit 407. A slurry phase of reaction medium 420b exits a lower slurry outlet 422 of secondary oxidation reactor 404 and is thereafter subjected to further downstream processing.

Inlet conduit 405 may attach to primary oxidation reactor 402 at any height. Although not shown in FIG. 15, reaction medium 420 can be mechanically pumped to secondary reaction zone 418 if desired. However, it is more preferable to use elevation head (gravity) to transfer reaction medium 420 from primary reaction zone 416 through inlet conduit 405 and into secondary reaction zone 418. Accordingly it is preferable that inlet conduit 405 is connected on one end to the upper 50, 30, 20, or 10 percent of the total height and/or volume of primary reaction zone 416. Preferably, the other end of inlet conduit 405 is attached to the upper 30, 20, 10, or 5 percent of the total height and/or volume of secondary reaction zone 418. Preferably, inlet conduit 405 is horizontal and/or sloping downward from primary oxidation reactor 402 toward secondary oxidation reactor 404. Outlet conduit 407 may attach to any elevation in secondary oxidation reactor 404, but it is preferable that outlet conduit 407 is connected to secondary oxidation reactor 404 above the attachment elevation of inlet conduit 405. More preferably, outlet conduit 407 attaches to the top of secondary oxidation reactor 404. Outlet conduit 407 preferably attaches to primary oxidation reactor 402 above the attachment elevation of inlet conduit 405. More preferably, outlet conduit 407 attaches to the upper 30, 20, 10, or 5 percent of the total height and/or volume of primary reaction zone 416. Preferably, outlet conduit 407 is horizontal and/or sloping upward from reaction secondary oxidation reactor 404 toward primary oxidation reactor 402. Although not shown in FIG. 15, outlet conduit 407 may also attach directly to the gas outlet conduit that withdraws gaseous effluent from the top of primary oxidation reactor 402. The upper extent of secondary reaction zone 416 may be above or below the upper extent of primary reaction zone 418. More preferably, the upper extent of primary reaction zone 416 is within 10 meters above to 50 meters below, 2 meters below to 40 meters below, or 5 meters below to 30 meters below the upper extent of secondary reaction zone 418. Lower slurry outlet 422 may exit from any elevation of secondary oxidation reactor 404, but it is preferable that lower slurry outlet 422 is connected to secondary oxidation reactor 404 below the attachment elevation of inlet conduit 405. The attachment point of lower slurry outlet 422 is more preferably widely separated in elevation from the attachment point of inlet conduit 405, with the two attachments separated by at least about 50, 70, 90, or 95 percent of the height of secondary reaction zone 418. Most preferably, lower slurry outlet 422 attaches to the bottom of secondary oxidation reactor 404 as shown in FIG. 15. The lower extent of secondary reaction zone 418 may be elevated above or below the lower extent of primary reaction zone 416. More preferably, the lower extent of primary reaction zone 416 is elevated within about 40, 20, 5, or 2 meters above or below the lower extent of secondary reaction zone 418.

Parameters (e.g., height, width, area, volume, relative horizontal placement, and relative vertical placement) specified herein for primary oxidation reactor 402 and appurtenances are also construed as applying to primary reaction zone 416 defined by primary oxidation reactor 402, and vice versa. Any parameters specified herein for secondary oxidation reactor 404 and appurtenances are also construed as applying to secondary reaction zone 418 defined by secondary oxidation reactor 404, and vice versa.

As mentioned above, it is preferred for secondary oxidation reactor 404 to be located outside of primary oxidation reactor 402. Preferably, secondary oxidation reactor 404 is located alongside primary oxidation reactor 402 (i.e., at least a portion of primary and secondary oxidation reactors 402 and 404 share a common elevation). Primary reaction zone 416 of primary oxidation reactor 402 has a maximum diameter "$D_p$". The volumetric centroid of secondary reaction zone 418 is preferably horizontally spaced from the volumetric centroid of primary reaction zone 416 by at least about $0.5D_p$, $0.75D_p$, or $1.0D_p$ and by less than about $30D_p$, $10D_p$, or $3D_p$.

Figure 16:
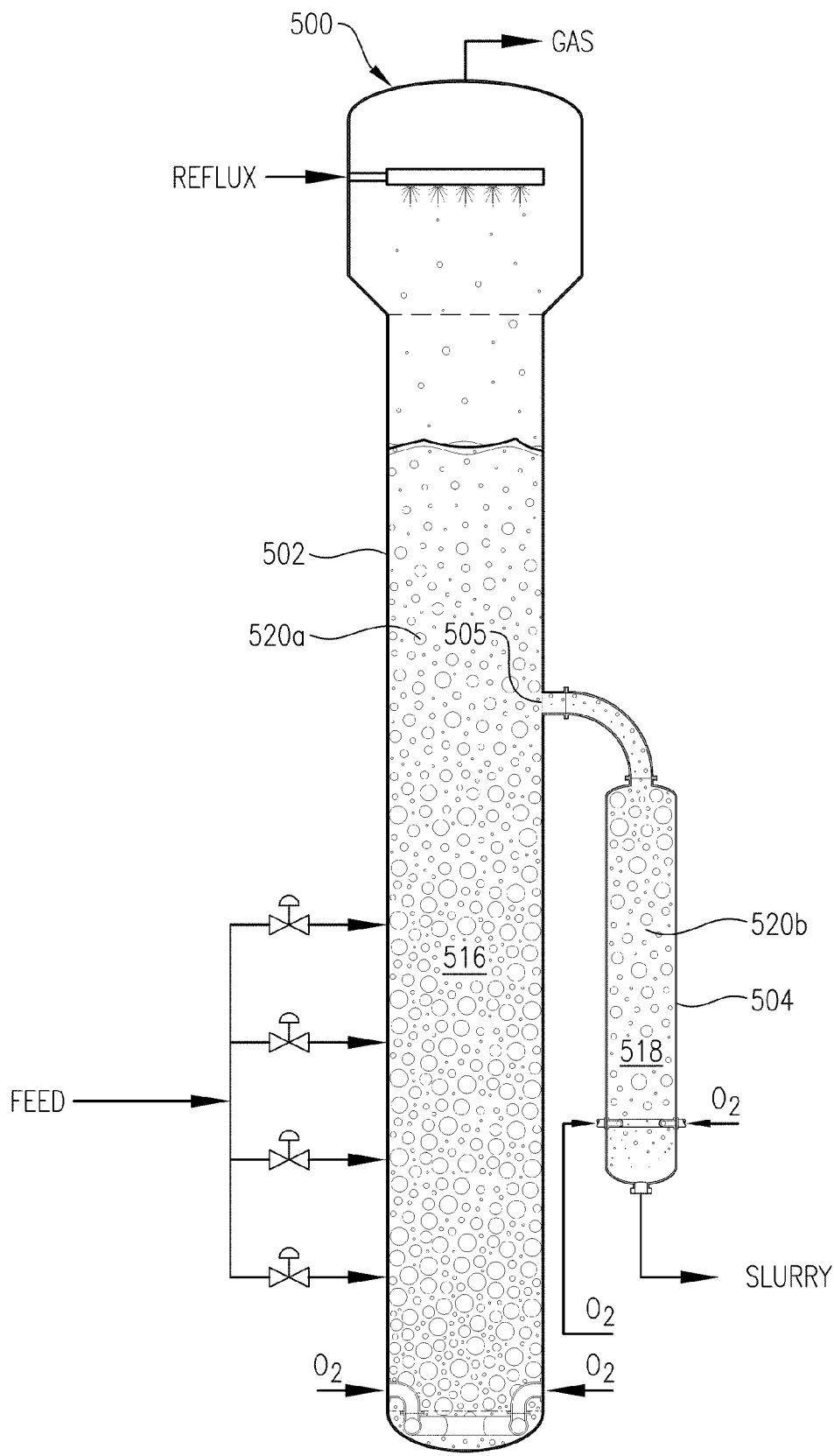
FIG. 16 is a side view of a bubble column reactor equipped with an open-ended external secondary oxidation reactor that receives slurry from an enlarged opening in the side of the primary oxidation reactor.

Referring now to FIG. 16, there is illustrated a reactor system 500 comprising a primary oxidation reactor 502 and a secondary oxidation reactor 504. Primary oxidation reactor defines therein a primary oxidation zone 516, while secondary oxidation reactor 504 defines therein a secondary oxidation zone 518. Each reaction zone 516 and 518 receives a portion of reaction medium 520.

The configuration and operation of reactor system 500 (FIG. 16) is preferably substantially the same as the configuration and of reactor system 400 (FIG. 15). However, in reactor system 500, the upright sidewall of primary oxidation reactor 502 defines at least one enlarged opening 505 that permits the transfer of reaction medium 520 from primary reaction zone 516 to secondary reaction zone 518, while simultaneously permitting the transfer of the disengaged gas phase from secondary reaction zone 518 to primary reaction zone 516. Preferably, the open area of enlarged opening 505 divided by the maximum horizontal cross sectional area of the upright portion of secondary reaction zone 218 is in the range of from about 0.01 to 2, 0.02 to 0.5, or 0.04 to 0.2. Primary reaction zone 516 of primary oxidation reactor 502 has a maximum height "$H_p$". It is preferred for the areal center of enlarged opening 505 to be vertically spaced at least about $0.1H_p$, $0.2H_p$, or $0.3H_p$ from the top and/or bottom of primary reaction zone 516.

Referring now to FIGS. 17-25, there is illustrated a number of bubble column reactors equipped with internal structures having a variety of configurations. It has been discovered that employing one or more internal structures surrounded by the reaction medium surprisingly modifies end-to-end mixing of the reaction medium. The internal structure defines a quiescent zone having reduced turbulence compared to the turbulence of the reaction medium surrounding the quiescent zone.

Figures 17A, 18A, 19A, 20A:
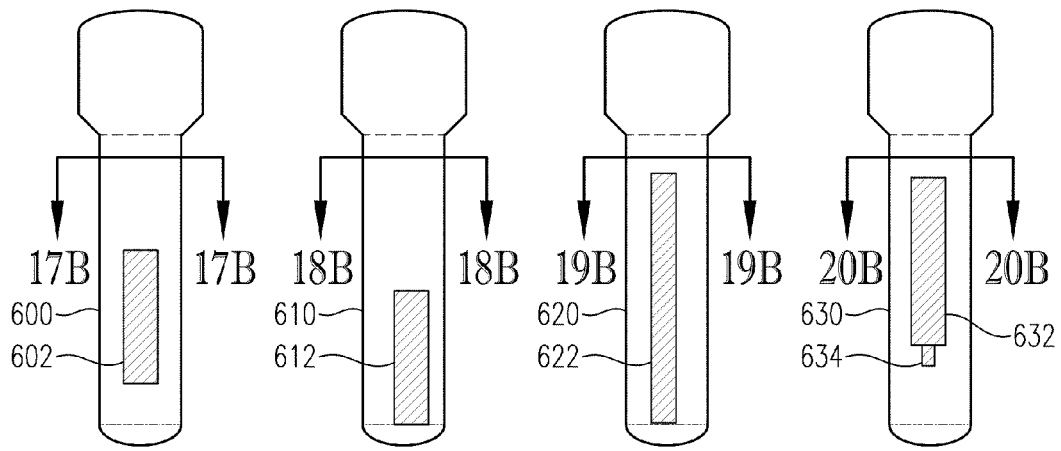
FIG. 17a is a schematic side view of a bubble column reactor equipped with an internal structure for enhancing the hydrodynamics of the reactor.
FIG. 18a is a schematic side view of a bubble column reactor equipped with a first alternative internal structure for enhancing the hydrodynamics of the reactor.
FIG. 19a is a schematic side view of a bubble column reactor equipped with a second alternative internal structure for enhancing the hydrodynamics of the reactor.
FIG. 20a is a schematic side view of a bubble column reactor equipped with a third alternative internal structure for enhancing the hydrodynamics of the reactor.
Figures 17B, 18B, 19B, 20B:

As illustrated in FIGS. 17-25, the internal structure can take a variety of forms. In particular, FIG. 17 illustrates a bubble column reactor 600 that employs a generally cylindrical internal structure 602 to define the quiescent zone. Internal structure 602 is substantially centered in the main reaction zone of bubble column reactor 600 and is vertically spaced from the top and bottom ends of the main reaction zone. FIG. 18 illustrates a bubble column reactor 610 that employs a generally cylindrical internal structure 612 that is similar to internal structure 602 of FIG. 17. However, internal structure 612 of FIG. 18 is not centered in the main reaction zone of bubble column reactor 610. Rather, the volumetric centroid of the quiescent zone defined by internal structure 612 is horizontally offset from the volumetric centroid of the main reaction zone.

Figures 21A, 22A, 23A, 24A:
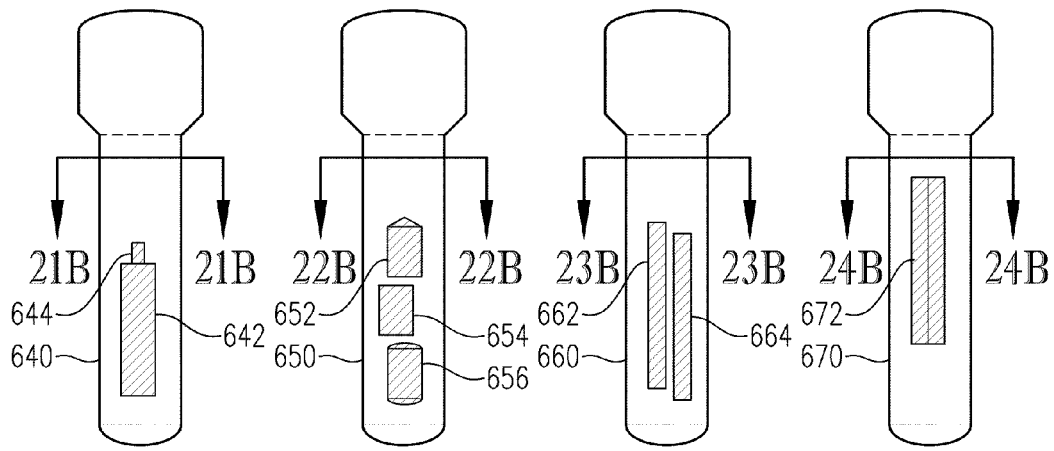
FIG. 21a is a schematic side view of a bubble column reactor equipped with a fourth alternative internal structure for enhancing the hydrodynamics of the reactor.
FIG. 22a is a schematic side view of a bubble column reactor equipped with a fifth alternative internal structure for enhancing the hydrodynamics of the reactor.
FIG. 23a is a schematic side view of a bubble column reactor equipped with a sixth alternative internal structure for enhancing the hydrodynamics of the reactor.
FIG. 24a is a schematic side view of a bubble column reactor equipped with a seventh alternative internal structure for enhancing the hydrodynamics of the reactor.
Figures 21B, 22B, 23B, 24B:

Further, the bottom of internal structure 612 is located near the lower tangent line of bubble column reactor 610. FIG. 19 illustrates a bubble column reactor 620 employing a generally cylindrical internal structure 622 that is taller than the internal structure 602 and 612 of FIGS. 17 and 18. Further, the volumetric centroid of the quiescent zone defined by internal structure 622 is offset from the volumetric centroid of the main reaction zone of bubble column reactor 620. FIG. 20 illustrates a bubble column reactor 630 employing an internal structure comprising a generally cylindrical upper portion 632 and a generally cylindrical lower portion 634. Lower portion 634 of the internal structure has a narrower diameter than upper portion 632. FIG. 21 illustrates a bubble column reactor 640 employing an internal structure comprising a generally cylindrical lower portion 642 and a generally cylindrical upper portion 644. Upper portion 644 of the internal structure has a narrower diameter than lower portion 642. FIG. 22 illustrates a bubble column reactor 650 employing first, second, and third separate internal structures 652, 654, and 656. Internal structures 652, 654, and 656 are vertically spaced from one another. The volumetric centroids of the quiescent zones defined by first and third internal structures 652 and 656 are horizontally aligned with the volumetric centroid of the main reaction zone of bubble column reactor 650. However, the volumetric centroid of the quiescent zone defined by second internal structure 654 is horizontally offset from the volumetric centroid of the main reaction zone of bubble column reactor 650. FIG. 23 illustrates a bubble column reactor 660 employing a pair of side-by-side first and second internal structures 662 and 664. The volumetric centroids of the quiescent zones defined by first and second internal structures 662 and 664 are horizontally spaced from one another and horizontally spaced from the volumetric centroid of the main reaction zone of bubble column reactor

Figure 25A:
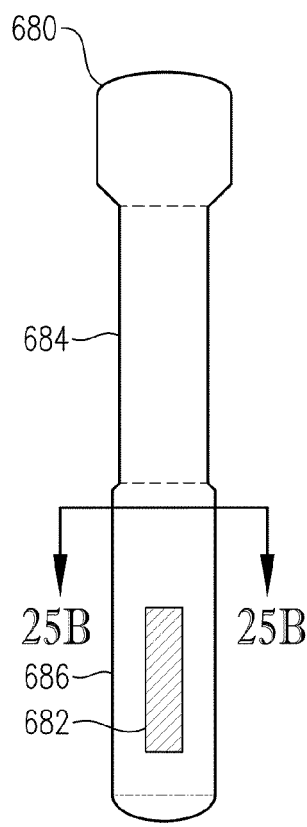
FIG. 25a is a schematic view of a stepped-diameter bubble column reactor equipped with a hydrodynamic-enhancing internal structure.
Figure 25B:
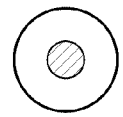

660. Further, first and second internal structures 662 and 664 have a side-by-side configuration so that at least a portion of first and second internal structures 662 and 664 share a common elevation. FIG. 24 illustrates a bubble column reactor 760 employing a generally prismatic internal structure 672. In particular, internal structure 672 has a generally triangular horizontal cross section. FIG. 25 illustrates a bubble column reactor 680 employing a generally cylindrical internal structure 682 that is similar to internal structure 602 of FIG. 17. However, the external reaction vessel of bubble column reactor 680 has a stepped diameter created by a narrow lower section 682 and a broad upper section 684.

As illustrated in FIGS. 17-25, the internal structure employed in accordance with one embodiment of the present invention can have a variety of shapes and can be disposed in a variety of positions within the main reaction zone of the bubble column reactor. Further, the internal structure and the quiescent zone defined therein can be formed of a variety of different materials. In one embodiment of the present invention, the internal structure is completely closed, so that none of the surrounding reaction medium enters the internal structure. Such a closed internal structure can be hollow or solid. In another embodiment of the present invention, the internal structure includes one or more openings that allow the reaction medium to enter the quiescent zone defined by the internal structure. However, because one purpose of the quiescent zone is to create a zone of reduced turbulence relative to the turbulence of the reaction medium surrounding it, it is preferred that the internal structure does not allow a significant amount of the reaction medium to rapidly flow through the internal structure.

The specific configuration and operating parameters of a bubble column reactor equipped with one or more internal structures will now be described in greater detail. Preferably, the internal structure is disposed entirely inside of the external reaction vessel of the bubble column reactor; however, it is possible for at least a portion of the internal structure to protrude outside of the external reaction vessel of the bubble column reactor. As mentioned above, during operation of the bubble column reactor, the internal structure defines at least one quiescent zone within the bubble column reactor. The main reaction zone of the bubble column reactor and the quiescent zone are distinct volumes (i.e., do not overlap one another). The main reaction zone of the bubble column reactor is defined inside the external reaction vessel of the bubble column reactor, but outside of the internal structure.

As mentioned above, the quiescent zone defined by the internal structure is a volume that has reduced turbulence relative to the turbulence of the adjacent reaction medium in the main reaction zone. It is preferred for at least about 90, 95, 98, or 99.9 percent of the volume of the quiescent zone to be filled with a material other than the reaction medium and/or to be filled with a portion of the reaction medium having substantially reduced turbulence compared to the reaction medium located adjacent the internal structure. If the quiescent zone includes any portion of the reaction medium, it is preferred for the portion of the reaction medium contained in the quiescent zone to have a mass-averaged residence time in the quiescent zone of at least about 2, 8, 30, or 120 minutes. If the quiescent zone includes any portion of the reaction medium, it is preferred for the time-averaged gas hold-up of the reaction medium in the quiescent zone to be less than about 0.2, 0.1, 0.5, or 0.01, where the gas hold-up is measured at any elevation of the quiescent zone, ¼-height of the quiescent zone, ½-height of the quiescent zone, ¾-height of the quiescent zone, and/or is an average over the entire height of the quiescent zone. It is preferred for the time-averaged gas hold-up of the reaction medium in the reaction zone to be in the range of from about 0.2 to about 0.9, more preferably, about 0.5 to about 0.8, and most preferably, 0.55 to 0.7, where the gas hold-up is measured at any elevation of the reaction zone, ¼-height of the reaction zone, ½-height of the reaction zone, ¾-height of the reaction zone, and/or is an average over the entire height of the reaction zone. If the quiescent zone includes any portion of the reaction medium, it is preferred for the time-averaged superficial gas velocity of the reaction medium in the quiescent zone to be less than about 0.4, 0.2, 0.1, or 0.05 meters per second, where the superficial gas velocity is measured at any elevation of the quiescent zone, ¼-height of the quiescent zone, ½-height of the quiescent zone, ¾-height of the quiescent zone, and/or is an average over the entire height of the quiescent zone. It is preferred for the time-averaged superficial gas velocity of the reaction medium in the reaction zone to be at least about 0.2, 0.4, 0.8, or 1 meters per second, where the superficial gas velocity is measured at any elevation of the reaction zone, ¼-height of the reaction zone, ½-height of the reaction zone, ¾-height of the reaction zone, and/or is an average over the entire height of the reaction zone. If the quiescent zone includes any portion of the reaction medium, it is preferred for the time-averaged superficial velocity of the liquid phase of the reaction medium in the quiescent zone to be less than about 0.04, 0.01, or 0.004 meters per second, where the superficial velocity of the liquid phase is measured at any elevation of the quiescent zone, ¼-height of the quiescent zone, ½-height of the quiescent zone, ¾-height of the quiescent zone, and/or is an average over the entire height of the quiescent zone. It is preferred for the time-averaged superficial velocity of the liquid phase of the reaction medium in the reaction zone to be less than about 0.1, 0.04, or 0.01 meters per second, where the superficial velocity of the liquid phase is measured at any elevation of the reaction zone, ¼-height of the reaction zone, ½-height of the reaction zone, ¾-height of the reaction zone, and/or is an average over the entire height of the reaction zone. Any parameters (e.g., height, width, area, volume, relative horizontal placement, and relative vertical placement) specified herein for the internal structure are also construed as applying to the quiescent zone defined by the internal structure, and vice versa.

It is preferred for the size of the quiescent zone defined by the internal structure to be such that the quiescent zone includes therein at least one location that is spaced from the reaction zone by at least about 0.05 times the maximum horizontal diameter of the reaction zone or about 0.2 meters, whichever is larger. Preferably, the quiescent zone includes therein at least one location that is spaced from the reaction zone by at least about 0.4, 0.7, or 1.0 meters. Preferably, the quiescent zone includes therein at least one location that is spaced from the reaction zone by at least about 0.1, 0.2, or 0.3 times the maximum horizontal diameter of the reaction zone. The quiescent zone preferably includes therein at least two locations that are spaced from one another by a vertical distance that is at least about 0.5, 1, 2, or 4 times the maximum horizontal diameter of the reaction zone. Preferably, these two vertically-spaced locations in the quiescent zone are also each separated from the reaction zone by at least about 0.05, 0.1, 0.2, or 0.3 times the maximum horizontal diameter of the reaction zone. Preferably, these two vertically-spaced locations in the quiescent zone are vertically-spaced from one another by at least about 1, 3, 10, or 20 meters and are each also separated from the reaction zone by at least about 0.1, 0.4, 0.7, or 1 meters. Preferably, the volume of the quiescent zone is in the range of from about 1 to about 50 percent of the volume of the main reaction zone, more preferably in the range of from about 2 to about 25 percent of the volume of the main reaction zone, and most preferably in the range of from 4 to 15 percent of the volume of the main reaction zone.

The external reaction vessel of the bubble column reactor preferably comprises a generally cylindrical upright external sidewall. Preferably, the internal structure comprises a generally cylindrical upright internal sidewall that is spaced inwardly from the external sidewall. Preferably, the internal structure is not part of a heat exchanger. Thus, it is preferred for the time-averaged heat flux through the upright internal sidewalls of the internal structure to be less than about 100, 15, 3, or 0.3 kilowatts per square meter. An annulus filled with the reaction medium is preferably defined between the internal and external sidewalls. The internal structure is supported vertically from the external vessel, preferably by upright supports between the lower portions of internal structure and the lower portion of external reaction vessel. In addition, the internal structure is preferably supported by the external reaction vessel via a plurality of non-fouling lateral support members extending inwardly from the external sidewall to the internal sidewall. Preferably, the horizontal cross sectional area of the quiescent zone at ¼-height, ½-height, and/or ¾-height of the quiescent zone is at least about 2, 5 to 75, or 10 to 30 percent of the horizontal cross sectional area of the annulus at the respective elevations. Preferably, the maximum height of the internal upright sidewall is in the range of from about 10 to about 90 percent of the maximum height of the external upright sidewall, more preferably in the range of from about 20 to about 80 percent of the maximum height of the external upright sidewall, and most preferably in the range of 30 to 70 percent of the maximum height of the external upright sidewall. Although it is preferred for the internal sidewall to have a generally cylindrical configuration, it is possible that a portion of the internal sidewall may be concave with respect to an adjacent portion of the quiescent zone. When the internal sidewall includes a concave portion, it is preferred for this concave portion to form less than about 25, 10, 5, or 0.1 percent of the total outwardly facing surface area presented by the internal sidewall. Preferably, the ratio of the total surface area of the internal structure that is in direct contact with the reaction medium to the total volume of the reaction zone is less than about 1, 0.5, 0.3, or 0.15 meters square per cubic meter. It is preferred for the volumetric centroid of the quiescent zone to be horizontally displaced from the volumetric centroid of the main reaction zone by less than about 0.4, 0.2, 0.1, or 0.01 times the maximum horizontal diameter of the main reaction zone.

When the bubble column reactor includes more than one internal structure defining more than one quiescent zone, it is preferred for the quiescent zones to be vertically aligned such that the volumetric centroid of all the quiescent zones considered together is horizontally displaced from the volumetric centroid of the reaction zone by less than about 0.4, 0.2, 0.1, or 0.01 times the maximum horizontal diameter of the main reaction zone. Further, when a plurality of quiescent zones are formed within the main reaction zone, it is preferred for the number of individual quiescent zones having a volume greater than 0.2 percent of the volume of the main reaction zone to be less than about 100, 10, 5, or 2.

The external reaction vessel of the bubble column reactor preferably has a ratio of maximum vertical height to maximum horizontal diameter in the range of from about 3:1 to about 30:1, more preferably in the range of from about 6:1 to about 20:1, and most preferably in the range of from 9:1 to 15:1. The internal structure preferably has a ratio of maximum vertical height to maximum horizontal diameter in the range of from about 0.3:1 to about 100:1, more preferably in the range of from about 1:1 to about 50:1, and most preferably in the range of from 3:1 to 30:1. It is preferred for the maximum horizontal diameter of the internal structure to be in the range of from about 0.1 to about 5 meters, more preferably in the range of from about 0.3 to about 4 meters, and most preferably in the range of from 1 to 3 meters. Preferably, the maximum vertical height of the internal structure is in the range of from about 1 to about 100 meters, more preferably in the range of from about 3 to about 50 meters, and most preferably in the range of from 10 to 50 meters. Preferably, the maximum horizontal diameter of the internal structure is in the range of from about 5 to about 80, more preferably about 10 to about 60, and most preferably 20 to 50 percent of the maximum horizontal diameter of the external reaction vessel. Preferably, the maximum vertical height of internal structure 602 is in the range of from about 3 to about 100 percent of the maximum vertical height of the external reaction vessel, more preferably in the range of from about 10 to about 90 percent of the maximum vertical height of the external reaction vessel, and most preferably in the range of from 30 to 80 percent of the maximum vertical height of the external reaction vessel. Any parameters (e.g., height, width, area, volume, relative horizontal placement, and relative vertical placement) specified herein for the external reaction vessel and appurtenances are also construed as applying to the reaction zone defined by the external reaction vessel, and vice versa.

In one embodiment of the present invention, the internal structure completely isolates the quiescent zone from the reaction zone. In an alternative embodiment, the internal structure defines one or more direct openings that permit direct fluid communication between the quiescent zone and the reaction zone. When the internal structure defines such direct openings, it is preferred for the maximum diameter of the smallest of the direct openings to be less than about 0.3, 0.2, 0.1, or 0.05 times the maximum horizontal diameter of the main reaction zone. When the internal structure defines such direct openings, it is preferred for the maximum diameter of the largest of the direct openings to be less than about 0.4, 0.3, 0.2, or 0.1 times the maximum horizontal diameter of the main reaction zone. When the internal structure defines such direct openings, it is preferred for the cumulative open area defined by all of the direct openings to be less than about 0.4, 0.3, or 0.2 times the maximum horizontal cross sectional area of the main reaction zone. The internal structure has a maximum height ($H_i$). When the internal structure defines one or more direct openings, it is preferred that less than about 50, 25, or 10 percent of the cumulative open area defined by all of the direct openings is spaced more than about $0.5H_i$, $0.25H_i$, or $0.1H_i$ from the top of the internal structure. When the bubble column reactor employs a plurality of internal structures to form a plurality of distinct quiescent zones, it is possible for two or more of the quiescent zones to include interconnecting openings and/or conduits that permit fluid communication between quiescent zones. Preferably, the maximum diameter of the smallest of each of these interconnected openings and/or conduits is less than about 0.3, 0.2, 0.1, or 0.05 times the maximum horizontal diameter of the main reaction zone.

As mentioned above, certain physical and operational features of the bubble column reactors, described above with reference to FIGS. 1-25, provide for vertical gradients in the pressure, temperature, and reactant (i.e., oxygen and oxidizable compound) concentrations of the processed reaction medium. As discussed above, these vertical gradients can provide for a more effective and economical oxidation process as compared to conventional oxidations processes, which favor a well-mixed reaction medium of relatively uniform pressure, temperature, and reactant concentration throughout. The vertical gradients for oxygen, oxidizable compound (e.g., para-xylene), and temperature made possible by employing an oxidation system in accordance with an embodiment of the present invention will now be discussed in greater detail.

Figure 26:
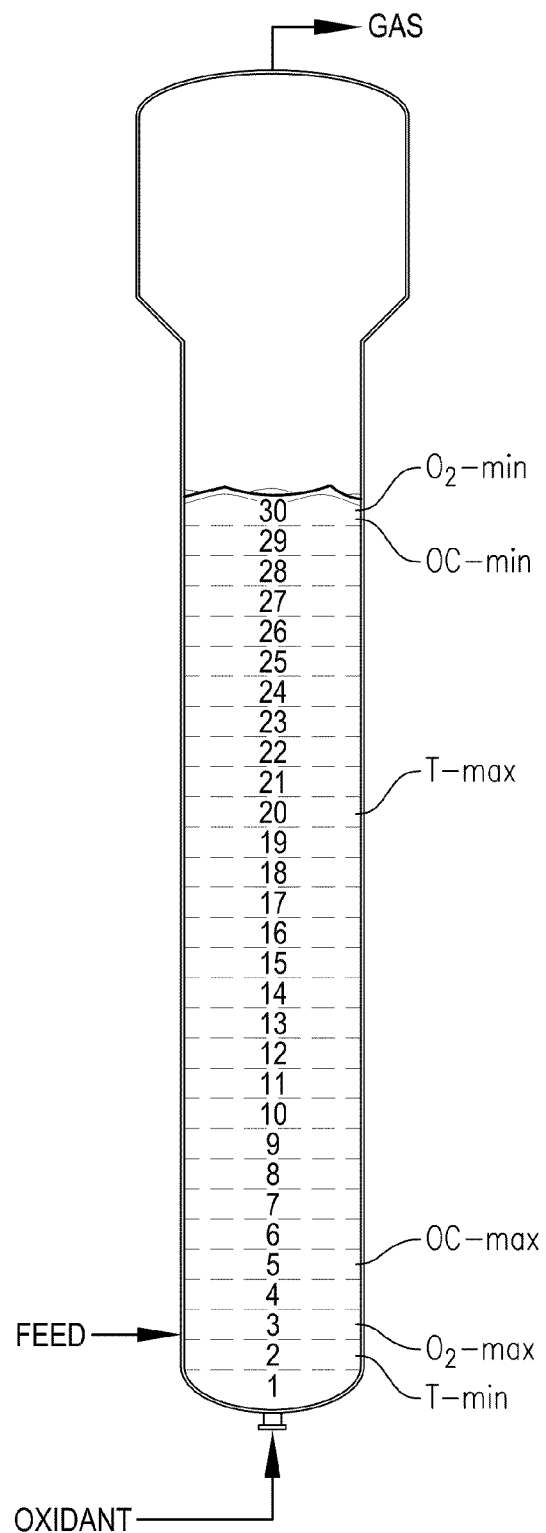
FIG. 26 is a side view of a bubble column reactor containing a multi-phase reaction medium, particularly illustrating the reaction medium being theoretically partitioned into 30 horizontal slices of equal volume in order to quantify certain gradients in the reaction medium.

Referring now to FIG. 26, in order to quantify the reactant concentration gradients existing in the reaction medium during oxidation in the bubble column reactor, the entire volume of the reaction medium can be theoretically partitioned into 30 discrete horizontal slices of equal volume. FIG. 26 illustrates the concept of dividing the reaction medium into 30 discrete horizontal slices of equal volume. With the exception of the highest and lowest horizontal slices, each horizontal slice is a discrete volume bounded on its top and bottom by imaginary horizontal planes and bounded on its sides by the wall of the reactor. The highest horizontal slice is bounded on its bottom by an imaginary horizontal plane and on its top by the upper surface of the reaction medium. The lowest horizontal slice is bounded on its top by an imaginary horizontal plane and on its bottom by the bottom of the vessel shell. Once the reaction medium has been theoretically partitioned into 30 discrete horizontal slices of equal volume, the time-averaged and volume-averaged concentration of each horizontal slice can then be determined. The individual horizontal slice having the maximum concentration of all 30 horizontal slices can be identified as the "C-max horizontal slice." The individual horizontal slice located above the C-max horizontal slice and having the minimum concentration of all horizontal slices located above the C-max horizontal slice can be identified as the "C-min horizontal slice." The vertical concentration gradient can then be calculated as the ratio of the concentration in the C-max horizontal slice to the concentration in the C-min horizontal slice.

With respect to quantifying the oxygen concentration gradient, when the reaction medium is theoretically partitioned into 30 discrete horizontal slices of equal volume, an $O_2$-max horizontal slice is identified as having the maximum oxygen concentration of all the 30 horizontal slices and an $O_2$-min horizontal slice is identified as having the minimum oxygen concentration of the horizontal slices located above the $O_2$-max horizontal slice. The oxygen concentrations of the horizontal slices are measured in the gas phase of the reaction medium on a time-averaged and volume-averaged molar wet basis. It is preferred for the ratio of the oxygen concentration of the $O_2$-max horizontal slice to the oxygen concentration of the $O_2$-min horizontal slice to be in the range of from about 2:1 to about 25:1, more preferably in the range of from about 3:1 to about 15:1, and most preferably in the range of from 4:1 to 10:1.

Typically, the $O_2$-max horizontal slice will be located near the bottom of the reaction medium, while the $O_2$-min horizontal slice will be located near the top of the reaction medium. Preferably, the $O_2$-min horizontal slice is one of the 5 upper-most horizontal slices of the 30 discrete horizontal slices. Most preferably, the $O_2$-min horizontal slice is the upper-most one of the 30 discrete horizontal slices, as illustrated in FIG. 26. Preferably, the $O_2$-max horizontal slice is one of the 10 lower-most horizontal slices of the 30 discrete horizontal slices. Most preferably, the $O_2$-max horizontal slice is one of the 5 lower-most horizontal slices of the 30 discrete horizontal slices. For example, FIG. 26 illustrates the $O_2$-max horizontal slice as the third horizontal slice from the bottom of the reactor. It is preferred for the vertical spacing between the $O_2$-min and $O_2$-max horizontal slices to be at least about 2W, more preferably at least about 4W, and most preferably at least 6W. It is preferred for the vertical spacing between the $O_2$-min and $O_2$-max horizontal slices to be at least about 0.2H, more preferably at least about 0.4H, and most preferably at least 0.6H The time-averaged and volume-averaged oxygen concentration, on a wet basis, of the $O_2$-min horizontal slice is preferably in the range of from about 0.1 to about 3 mole percent, more preferably in the range of from about 0.3 to about 2 mole percent, and most preferably in the range of from 0.5 to 1.5 mole percent. The time-averaged and volume-averaged oxygen concentration of the $O_2$-max horizontal slice is preferably in the range of from about 4 to about 20 mole percent, more preferably in the range of from about 5 to about 15 mole percent, and most preferably in the range of from 6 to 12 mole percent. The time-averaged concentration of oxygen, on a dry basis, in the gaseous effluent discharged from the reactor via the gas outlet is preferably in the range of from about 0.5 to about 9 mole percent, more preferably in the range of from about 1 to about 7 mole percent, and most preferably in the range of from 1.5 to 5 mole percent.

Because the oxygen concentration decays so markedly toward the top of the reaction medium, it is desirable that the demand for oxygen be reduced in the top of the reaction medium. This reduced demand for oxygen near the top of the reaction medium can be accomplished by creating a vertical gradient in the concentration of the oxidizable compound (e.g., para-xylene), where the minimum concentration of oxidizable compound is located near the top of the reaction medium.

With respect to quantifying the oxidizable compound (e.g., para-xylene) concentration gradient, when the reaction medium is theoretically partitioned into 30 discrete horizontal slices of equal volume, an OC-max horizontal slice is identified as having the maximum oxidizable compound concentration of all the 30 horizontal slices and an OC-min horizontal slice is identified as having the minimum oxidizable compound concentration of the horizontal slices located above the OC-max horizontal slice. The oxidizable compound concentrations of the horizontal slices are measured in the liquid phase on a time-averaged and volume-averaged mass fraction basis. It is preferred for the ratio of the oxidizable compound concentration of the OC-max horizontal slice to the oxidizable compound concentration of the OC-min horizontal slice to be greater than about 5:1, more preferably greater than about 10:1, still more preferably greater than about 20:1, and most preferably in the range of from 40:1 to 1000:1.

Typically, the OC-max horizontal slice will be located near the bottom of the reaction medium, while the OC-min horizontal slice will be located near the top of the reaction medium. Preferably, the OC-min horizontal slice is one of the 5 upper-most horizontal slices of the 30 discrete horizontal slices. Most preferably, the OC-min horizontal slice is the upper-most one of the 30 discrete horizontal slices, as illustrated in FIG. 26. Preferably, the OC-max horizontal slice is one of the 10 lower-most horizontal slices of the 30 discrete horizontal slices. Most preferably, the OC-max horizontal slice is one of the 5 lower-most horizontal slices of the 30 discrete horizontal slices. For example, FIG. 26 illustrates the OC-max horizontal slice as the fifth horizontal slice from the bottom of the reactor. It is preferred for the vertical spacing between the OC-min and OC-max horizontal slices to be at least about 2W, where "W" is the maximum width of the reaction medium. More preferably, the vertical spacing between the OC-min and OC-max horizontal slices is at least about 4W, and most preferably at least 6W. Given a height "H" of the reaction medium, it is preferred for the vertical spacing between the OC-min and OC-max horizontal slices to be at least about 0.2H, more preferably at least about 0.4H, and most preferably at least 0.6H.

The time-averaged and volume-averaged oxidizable compound (e.g., para-xylene) concentration in the liquid phase of the OC-min horizontal slice is preferably less than about 5,000 ppmw, more preferably less than about 2,000 ppmw, still more preferably less than about 400 ppmw, and most preferably in the range of from 1 ppmw to 100 ppmw. The time-averaged and volume-averaged oxidizable compound concentration in the liquid phase of the OC-max horizontal slice is preferably in the range of from about 100 ppmw to about 10,000 ppmw, more preferably in the range of from about 200 ppmw to about 5,000 ppmw, and most preferably in the range of from 500 ppmw to 3,000 ppmw.

Although it is preferred for the bubble column reactor to provide vertical gradients in the concentration of the oxidizable compound, it is also preferred that the volume percent of the reaction medium having an oxidizable compound concentration in the liquid phase above 1,000 ppmw be minimized. Preferably, the time-averaged volume percent of the reaction medium having an oxidizable compound concentration in the liquid phase above 1,000 ppmw is less than about 9 percent, more preferably less than about 6 percent, and most preferably less than 3 percent. Preferably, the time-averaged volume percent of the reaction medium having an oxidizable compound concentration in the liquid phase above 2,500 ppmw is less than about 1.5 percent, more preferably less than about 1 percent, and most preferably less than 0.5 percent. Preferably, the time-averaged volume percent of the reaction medium having an oxidizable compound concentration in the liquid phase above 10,000 ppmw is less than about 0.3 percent, more preferably less than about 0.1 percent, and most preferably less than 0.03 percent. Preferably, the time-averaged volume percent of the reaction medium having an oxidizable compound concentration in the liquid phase above 25,000 ppmw is less than about 0.03 percent, more preferably less than about 0.015 percent, and most preferably less than 0.007 percent. The inventors note that the volume of the reaction medium having the elevated levels of oxidizable compound need not lie in a single contiguous volume. At many times, the chaotic flow patterns in a bubble column reaction vessel produce simultaneously two or more continuous but segregated portions of the reaction medium having the elevated levels of oxidizable compound. At each time used in the time averaging, all such continuous but segregated volumes larger than 0.0001 volume percent of the total reaction medium are added together to determine the total volume having the elevated levels of oxidizable compound concentration in the liquid phase.

In addition to the concentration gradients of oxygen and oxidizable compound, discussed above, it is preferred for a temperature gradient to exist in the reaction medium. Referring again to FIG. 26, this temperature gradient can be quantified in a manner similar to the concentration gradients by theoretically partitioning the reaction medium into 30 discrete horizontal slices of equal volume and measuring the time-averaged and volume-averaged temperature of each slice. The horizontal slice with the lowest temperature out of the lowest 15 horizontal slices can then be identified as the T-min horizontal slice, and the horizontal slice located above the T-min horizontal slice and having the maximum temperature of all the slices above the T-min horizontal slice can then be identified as the "T-max horizontal slice." It is preferred for the temperature of the T-max horizontal slice to be at least about 1° C. higher than the temperature of the T-min horizontal slice. More preferably the temperature of the T-max horizontal slice is in the range of from about 1.25 to about 12° C. higher than the temperature of the T-min horizontal slice. Most preferably the temperature of the T-max horizontal slice is in the range of from 2 to 8° C. higher than the temperature of the T-min horizontal slice. The temperature of the T-max horizontal slice is preferably in the range of from about 125 to about 200° C., more preferably in the range of from about 140 to about 180° C., and most preferably in the range of from 150 to 170° C.

Typically, the T-max horizontal slice will be located near the center of the reaction medium, while the T-min horizontal slice will be located near the bottom of the reaction medium. Preferably, the T-min horizontal slice is one of the 10 lowermost horizontal slices of the 15 lowest horizontal slices. Most preferably, the T-min horizontal slice is one of the 5 lowermost horizontal slices of the 15 lowest horizontal slices. For example, FIG. 26 illustrates the T-min horizontal slice as the second horizontal slice from the bottom of the reactor. Preferably, the T-max horizontal slice is one of the 20 middle horizontal slices of the 30 discrete horizontal slices. Most preferably, the T-min horizontal slice is one of the 14 middle horizontal slices of the 30 discrete horizontal slices. For example, FIG. 26 illustrates the T-max horizontal slice as the twentieth horizontal slice from the bottom of the reactor (i.e., one of the middle 10 horizontal slices). It is preferred for the vertical spacing between the T-min and T-max horizontal slices to be at least about 2W, more preferably at least about 4W, and most preferably at least 6W. It is preferred for the vertical spacing between the T-min and T-max horizontal slices to be at least about 0.2H, more preferably at least about 0.4H, and most preferably at least 0.6H.

As discussed above, when a vertical temperature gradient exists in the reaction medium, it can be advantageous to withdraw the reaction medium at an elevated location where the temperature of reaction medium is highest, especially when the withdrawn product is subjected to further downstream processing at higher temperatures. Thus, when reaction medium 36 is withdrawn from the reaction zone via one or more elevated outlets, as illustrated in FIGS. 15 and 16, it is preferred for the elevated outlet(s) to be located near the T-max horizontal slice. Preferably, the elevated outlet is located within 10 horizontal slices of the T-max horizontal slice, more preferably within 5 horizontal slices of the T-max horizontal slice, and most preferably within 2 horizontal slices of the T-max horizontal slice.

It is now noted that many of the inventive features described herein can be employed in multiple oxidation reactor systems—not just systems employing a single oxidation reactor. In addition, certain inventive features described herein can be employed in mechanically-agitated and/or flow-agitated oxidation reactors—not just bubble-agitated reactors (i.e., bubble column reactors). For example, the inventors have discovered certain advantages associated with staging/varying oxygen concentration and/or oxygen consumption rate throughout the reaction medium. The advantages realized by the staging of oxygen concentration/consumption in the reaction medium can be realized whether the total volume of the reaction medium is contained in a single vessel or in multiple vessels. Further, the advantages realized by the staging of oxygen concentration/consumption in the reaction medium can be realized whether the reaction vessel(s) is mechanically-agitated, flow-agitated, and/or bubble-agitated.

Figure 27:
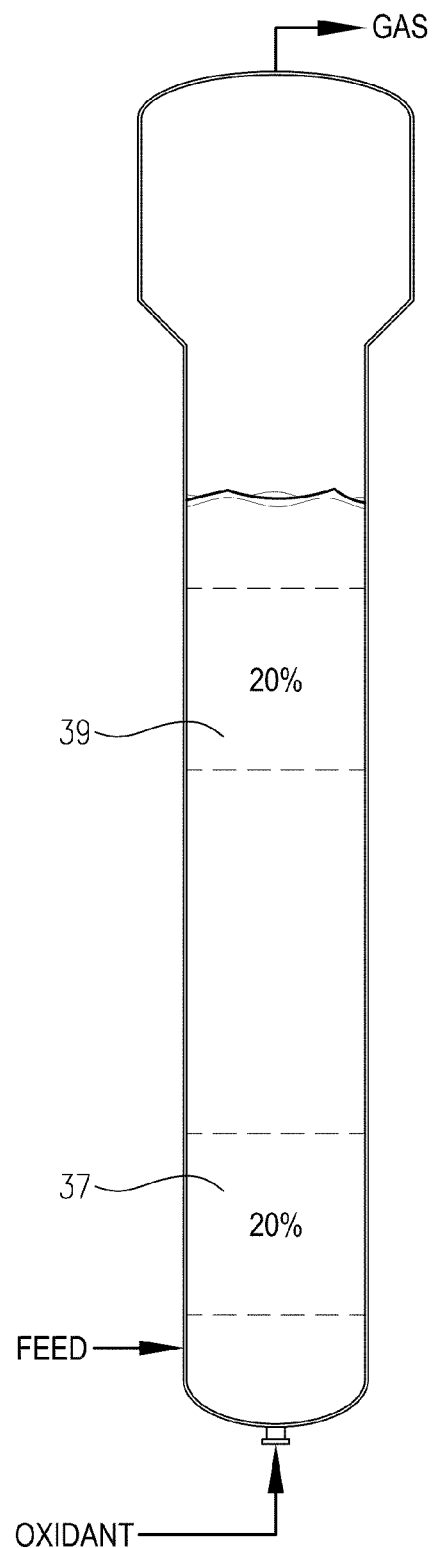
FIG. 27 is a side view of a bubble column reactor containing a multi-phase reaction medium, particularly illustrating first and second discrete 20-percent continuous volumes of the reaction medium that have substantially different oxygen concentrations and/or oxygen consumption rates.

One way of quantifying the degree of staging of oxygen concentration and/or consumption rate in a reaction medium is to compare two or more distinct 20-percent continuous volumes of the reaction medium. These 20-percent continuous volumes need not be defined by any particular shape. However, each 20-percent continuous volume must be formed of a contiguous volume of the reaction medium (i.e., each volume is "continuous"), and the 20-percent continuous volumes must not overlap one another (i.e., the volumes are "distinct"). These distinct 20-percent continuous volumes can be located in the same reactor (FIG. 29) or in multiple reactors. Referring now to FIG. 27, the bubble column reactor is illustrated as containing a reaction medium that includes a first distinct 20-percent continuous volume 37 and a second distinct 20-percent continuous volume 39.

The staging of oxygen availability in the reaction medium can be quantified by referring to the 20-percent continuous volume of reaction medium having the most abundant mole fraction of oxygen in the gas phase and by referring to the 20-percent continuous volume of reaction medium having the most depleted mole fraction of oxygen in the gas phase. In the gas phase of the distinct 20-percent continuous volume of the reaction medium containing the highest concentration of oxygen in the gas phase, the time-averaged and volume-averaged oxygen concentration, on a wet basis, is preferably in the range of from about 3 to about 18 mole percent, more preferably in the range of from about 3.5 to about 14 mole percent, and most preferably in the range of from 4 to 10 mole percent. In the gas phase of the distinct 20-percent continuous volume of the reaction medium containing the lowest concentration of oxygen in the gas phase, the time-averaged and volume-averaged oxygen concentration, on a wet basis, is preferably in the range of from about 0.3 to about 5 mole percent, more preferably in the range of from about 0.6 to about 4 mole percent, and most preferably in the range of from 0.9 to 3 mole percent. Furthermore, the ratio of the time-averaged and volume-averaged oxygen concentration, on a wet basis, in the most abundant 20-percent continuous volume of reaction medium compared to the most depleted 20-percent continuous volume of reaction medium is preferably in the range of from about 1.5:1 to about 20:1, more preferably in the range of from about 2:1 to about 12:1, and most preferably in the range of from 3:1 to 9:1.

The staging of oxygen consumption rate in the reaction medium can be quantified in terms of an oxygen-STR, initially described above. Oxygen-STR was previously describe in a global sense (i.e., from the perspective of the average oxygen-STR of the entire reaction medium); however, oxygen-STR may also be considered in a local sense (i.e., a portion of the reaction medium) in order to quantify staging of the oxygen consumption rate throughout the reaction medium.

The inventors have discovered that it is very useful to cause the oxygen-STR to vary throughout the reaction medium in general harmony with the desirable gradients disclosed herein relating to pressure in the reaction medium and to the mole fraction of molecular oxygen in the gas phase of the reaction medium. Thus, it is preferable that the ratio of the oxygen-STR of a first distinct 20-percent continuous volume of the reaction medium compared to the oxygen-STR of a second distinct 20-percent continuous volume of the reaction medium be in the range of from about 1.5:1 to about 20:1, more preferably in the range of from about 2:1 to about 12:1, and most preferably in the range of from 3:1 to 9:1. In one embodiment the "first distinct 20-percent continuous volume" is located closer than the "second distinct 20-percent continuous volume" to the location where molecular oxygen is initially introduced into the reaction medium. These large gradients in oxygen-STR are desirable whether the partial oxidation reaction medium is contained in a bubble column oxidation reactor or in any other type of reaction vessel in which gradients are created in pressure and/or mole fraction of molecular oxygen in the gas phase of the reaction medium (e.g., in a mechanically agitated vessel having multiple, vertically disposed stirring zones achieved by using multiple impellers having strong radial flow, possibly augmented by generally horizontal baffle assemblies, with oxidant flow rising generally upwards from a feed near the lower portion of the reaction vessel, notwithstanding that considerable back-mixing of oxidant flow may occur within each vertically disposed stirring zone and that some back-mixing of oxidant flow may occur between adjacent vertically disposed stirring zones). That is, when a gradient exists in the pressure and/or mole fraction of molecular oxygen in the gas phase of the reaction medium, the inventors have discovered that it is desirable to create a similar gradient in the chemical demand for dissolved oxygen by the means disclosed herein.

A preferred means of causing the local oxygen-STR to vary is by controlling the locations of feeding the oxidizable compound and by controlling the mixing of the liquid phase of the reaction medium to control gradients in concentration of oxidizable compound according to other disclosures of the present invention. Other useful means of causing the local oxygen-STR to vary include causing variation in reaction activity by causing local temperature variation and by changing the local mixture of catalyst and solvent components (e.g., by introducing an additional gas to cause evaporative cooling in a particular portion of the reaction medium and by adding a solvent stream containing a higher amount of water to decrease activity in a particular portion of the reaction medium).

When the oxidation reactor has a reactor-in-reactor configuration, as described above with respect to FIGS. 12-14, it is preferred for the concentration gradients, temperature gradients, and oxygen-STR gradients described herein with reference to FIGS. 26 and 27 to apply to the portion of the reaction medium located inside the external reactor and outside the internal reactor (e.g., reaction medium 220a in FIG. 12).

Referring again to FIGS. 1-27, oxidation is preferably carried out in the bubble column reactor under conditions that are markedly different, according to preferred embodiments disclosed herein, than conventional oxidation reactors. When the bubble column reactor is used to carry out the liquid-phase partial oxidation of para-xylene to crude terephthalic acid (CTA) according to preferred embodiments disclosed herein, the spatial profiles of local reaction intensity, of local evaporation intensity, and of local temperature combined with the liquid flow patterns within the reaction medium and the preferred, relatively low oxidation temperatures contribute to the formation of CTA particles having unique and advantageous properties.

FIGS. 28A and 28B illustrate base CTA particles produced in accordance with one embodiment of the present invention. FIG. 28A shows the base CTA particles at 500 times magnification, while FIG. 28B zooms in on one of the base CTA particles and shows that particle at 2,000 times magnification. As perhaps best illustrated in FIG. 28B, each base CTA particle is typically formed of a large number of small, agglomerated CTA subparticles, thereby giving the base CTA particle a relatively high surface area, high porosity, low density, and good dissolvability. Unless otherwise specified, the various properties of the inventive CTA, described below, are measured using a representative sample of the CTA, where the representative sample weighs at least 1 gram and/or is formed of at least 10,000 individual CTA particles. The base CTA particles typically have a mean particle size in the range of from about 20 to about 150 microns, more preferably in the range of from about 30 to about 120 microns, and most preferably in the range of from 40 to 90 microns. The CTA subparticles typically have a mean particle size in the range of from about 0.5 to about 30 microns, more preferably from about 1 to about 15 microns, and most preferably in the range of from 2 to 5 microns. The relatively high surface area of the base CTA particles illustrated in FIGS. 28A and 28B, can be quantified using a Braunauer-Emmett-Teller (BET) surface area measurement method. Preferably, the base CTA particles have an average BET surface of at least about 0.6 meters squared per gram ($m^2/g$). More preferably, the base CTA particles have an average BET surface area in the range of from about 0.8 to about 4 $m^2/g$. Most preferably, the base CTA particles have an average BET surface area in the range of from 0.9 to 2 $m^2/g$. The physical properties (e.g., particle size, BET surface area, porosity, and dissolvability) of the base CTA particles formed by optimized oxidation process of a preferred embodiment of the present invention permit purification of the CTA particles by more effective and/or economical methods, as described in further detail below with respect to FIG. 31.

The mean particle size values provided above were determined using polarized light microscopy and image analysis. The equipment employed in the particle size analysis included a Nikon E800 optical microscope with a 4× Plan Flour N.A. 0.13 objective, a Spot RT™ digital camera, and a personal computer running Image Pro Plus™ V4.5.0.19 image analysis software. The particle size analysis method included the following main steps: (1) dispersing the CTA powders in mineral oil; (2) preparing a microscope slide/cover slip of the dispersion; (3) examining the slide using polarized light microscopy (crossed polars condition—particles appear as bright objects on black background); (4) capturing different images for each sample preparation (field size=3×2.25 mm; pixel size=1.84 microns/pixel); (5) performing image analysis with Image Pro Plus™ software; (6) exporting the particle measures to a spreadsheet; and (7) performing statistical characterization in the spreadsheet. Step (5) of "performing image analysis with Image Pro Plus™ software" included the substeps of: (a) setting the image threshold to detect white particles on dark background; (b) creating a binary image; (c) running a single-pass open filter to filter out pixel noise; (d) measuring all particles in the image; and (e) reporting the mean diameter measured for each particle. The Image Pro Plus™ software defines mean diameter of individual particles as the number average length of diameters of a particle measured at 2 degree intervals and passing through the particle's centroid. Step 7 of "performing statistical characterization in the spreadsheet" comprises calculating the volume-weighted mean particle size as follows. The volume of each of the n particles in a sample is calculated as if it were spherical using $pi/6*d_i\hat{\ }3$; multiplying the volume of each particle times its diameter to find $pi/6* d_i\hat{\ }4$; summing for all particles in the sample of the values of $pi/6* d_i\hat{\ }4$; summing the volumes of all particles in the sample; and calculating the volume-weighted particle diameter as sum for all n particles in the sample of $(pi/6*d_i\hat{\ }4)$ divided by sum for all n particles in the sample of $(pi/6*d_i\hat{\ }3)$. As used herein, "mean particle size" refers to the volume-weighted meanparticle size determined according to the above-described test method; and it is also referred to as D(4,3).

$$D(4,3) = \frac{\sum_{i=1}^{n} \frac{\pi}{6} d_i^4}{\sum_{i=1}^{n} \frac{\pi}{6} d_i^3}$$

In addition, step 7 comprises finding the particle sizes for which various fractions of the total sample volume are smaller. For example, D(v,0.1) is the particle size for which 10 percent of the total sample volume is smaller and 90 percent is larger; D(v,0.5) is the particle size for which one-half of the sample volume is larger and one-half is smaller; D(v,0.9) is the particle size for which 90 percent of the total sample volume is smaller; and so on. In addition, step 7 comprises calculating the value of D(v,0.9) minus D(v,0.1), which is herein defined as the "particle size spread"; and step 7 comprises calculating the value of the particle size spread divided by D(4,3), which is herein defined as the "particle size relative spread."

Furthermore, it is preferable that the D(v,0.1) of the CTA particles as measured above be in the range from about 5 to about 65 microns, more preferably in the range from about 15 to about 55 microns and most preferably in the range from 25 to 45 microns. It is preferable that the D(v,0.5) of the CTA particles as measured above be in the range from about 10 to about 90 microns, more preferably in the range from about 20 to about 80 microns, and most preferably in the range from 30 to 70 microns. It is preferable that the D(v,0.9) of the CTA particles as measured above be in the range from about 30 to about 150 microns, more preferably in the range from about 40 to about 130 microns, and most preferably in the range from 50 to 110 microns. It is preferable that the particle size relative spread be in the range from about 0.5 to about 2.0, more preferably in the range from about 0.6 to about 1.5, and most preferably in the range from 0.7 to 1.3.

The BET surface area values provided above were measured on a Micromeritics ASAP2000 (available from Micromeritics Instrument Corporation of Norcross, Ga.). In the first step of the measurement process, a 2 to 4 gram of sample of the particles was weighed and dried under vacuum at 50° C. The sample was then placed on the analysis gas manifold and cooled to 77° K. A nitrogen adsorption isotherm was measured at a minimum of 5 equilibrium pressures by exposing the sample to known volumes of nitrogen gas and measuring the pressure decline. The equilibrium pressures were appropriately in the range of $P/P_0$=0.01-0.20, where P is equilibrium pressure and $P_0$ is vapor pressure of liquid nitrogen at 77° K. The resulting isotherm was then plotted according to the following BET equation:

$$\frac{P}{V_a(P_o - P)} = \frac{1}{V_m C} + \frac{C-1}{V_m C}\left(\frac{P}{P_o}\right)$$

where $V_a$ is volume of gas adsorbed by sample at P, $V_m$ is volume of gas required to cover the entire surface of the sample with a monolayer of gas, and C is a constant. From this plot, $V_m$ and C were determined. $V_m$ was then converted to a surface area using the cross sectional area of nitrogen at 77° K. by:

$$A = \sigma \frac{V_m}{RT}$$

where σ is cross sectional area of nitrogen at 77° K., T is 77° K., and R is the gas constant.

As alluded to above, CTA formed in accordance with one embodiment of the present invention exhibits superior dissolution properties verses conventional CTA made by other processes. This enhanced dissolution rate allows the inventive CTA to be purified by more efficient and/or more effective purification processes. The following description addresses the manner in which the rate of dissolution of CTA can be quantified.

The rate of dissolution of a known amount of solids into a known amount of solvent in an agitated mixture can be measured by various protocols. As used herein, a measurement method called the "timed dissolution test" is defined as follows. An ambient pressure of about 0.1 megapascal is used throughout the timed dissolution test. The ambient temperature used throughout the timed dissolution test is about 22° C. Furthermore, the solids, solvent and all dissolution apparatus are fully equilibrated thermally at this temperature before beginning testing, and there is no appreciable heating or cooling of the beaker or its contents during the dissolution time period. A solvent portion of fresh, HPLC analytical grade of tetrahydrofuran (>99.9 percent purity), hereafter THF, measuring 250 grams is placed into a cleaned KIMAX tall form 400 milliliter glass beaker (Kimble® part number 14020, Kimble/Kontes, Vineland, N.J.), which is uninsulated, smooth-sided, and generally cylindrical in form. A Teflon-coated magnetic stirring bar (VWR part number 58948-230, about 1-inch long with ⅜-inch diameter, octagonal cross section, VWR International, West Chester, Pa. 19380) is placed in the beaker, where it naturally settles to the bottom. The sample is stirred using a Variomag® multipoint 15 magnetic stirrer (H&P Labortechnik AG, Oberschleissheim, Germany) magnetic stirrer at a setting of 800 revolutions per minute. This stirring begins no more than 5 minutes before the addition of solids and continues steadily for at least 30 minutes after adding the solids. A solid sample of crude or purified TPA particulates amounting to 250 milligrams is weighed into a non-sticking sample weighing pan. At a starting time designated as t=0, the weighed solids are poured all at once into the stirred THF, and a timer is started simultaneously. Properly done, the THF very rapidly wets the solids and forms a dilute, well-agitated slurry within 5 seconds. Subsequently, samples of this mixture are obtained at the following times, measured in minutes from t=0: 0.08, 0.25, 0.50, 0.75, 1.00, 1.50, 2.00, 2.50, 3.00, 4.00, 5.00, 6.00, 8.00, 10.00, 15.00, and 30.00. Each small sample is withdrawn from the dilute, well-agitated mixture using a new, disposable syringe (Becton, Dickinson and Co, 5 milliliter, REF 30163, Franklin Lakes, N.J. 07417) Immediately upon withdrawal from the beaker, approximately 2 milliliters of clear liquid sample is rapidly discharged through a new, unused syringe filter (25 mm diameter, 0.45 micron, Gelman GHP Acrodisc GF®, Pall Corporation, East Hills, N.Y. 11548) into a new, labeled glass sample vial. The duration of each syringe filling, filter placement, and discharging into a sample vial is correctly less than about 5 seconds, and this interval is appropriately started and ended within about 3 seconds either side of each target sampling time. Within about five minutes of each filling, the sample vials are capped shut and maintained at approximately constant temperature until performing the following chemical analysis. After the final sample is taken at a time of 30 minutes past t=0, all sixteen samples are analyzed for the amount of dissolved TPA using a HPLC-DAD method generally as described elsewhere within this disclosure. However, in the present test, the calibration standards and the results reported are both based upon milligrams of dissolved TPA per gram of THF solvent (hereafter "ppm in THF"). For example, if all of the 250 milligrams of solids were very pure TPA and if this entire amount fully dissolved in the 250 grams of THF solvent before a particular sample were taken, the correctly measured concentration would be about 1,000 ppm in THF.

When CTA according to the present invention is subjected to the timed dissolution test described above, it is preferred that a sample taken at one minute past t=0 dissolves to a concentration of at least about 500 ppm in THF, more preferably to at least 600 ppm in THF. For a sample taken at two minutes past t=0, it is preferred that CTA according to the current invention will dissolve to a concentration of at least about 700 ppm in THF, more preferably to at least 750 ppm in THF. For a sample taken at four minutes past t=0, it is preferred that CTA according to the current invention will dissolve to a concentration of at least about 840 ppm in THF, more preferably to at least 880 ppm in THF.

The inventors have found that a relatively simple negative exponential growth model is useful to describe the time dependence of the entire data set from a complete timed dissolution test, notwithstanding the complexity of the particulate samples and of the dissolution process. The form of the equation, hereinafter the "timed dissolution model," is as follows:

$S=A+B*(1-\exp(-C*t))$, where t=time in units of minutes;
S=solubility, in units of ppm in THF, at time t;
exp=exponential function in the base of the natural logarithm of 2;
A, B=regressed constants in units of ppm in THF, where A relates mostly to the rapid dissolution of the smaller particles at very short times, and where the sum of A+B relates mostly to the total amount of dissolution near the end of the specified testing period; and
C=a regressed time constant in units of reciprocal minutes.

The regressed constants are adjusted to minimize the sum of the squares of the errors between the actual data points and the corresponding model values, which method is commonly called a "least squares" fit. A preferred software package for executing this data regression is JMP Release 5.1.2 (SAS Institute Inc., JMP Software, SAS Campus Drive, Cary, N.C. 27513).

When CTA according to the present invention is tested with the timed dissolution test and fitted to the timed dissolution model described above, it is preferred for the CTA to have a time constant "C" greater than about 0.5 reciprocal minutes, more preferably greater than about 0.6 reciprocal minutes, and most preferably greater than 0.7 reciprocal minutes.

FIGS. 29A and 29B illustrate a conventional CTA particle made by a conventional high-temperature oxidation process in a continuous stirred tank reactor (CSTR). FIG. 29A shows the conventional CTA particle at 500 times magnification, while FIG. 29B zooms in and shows the CTA particle at 2,000 times magnification. A visual comparison of the inventive CTA particles illustrated in FIGS. 28A and 28B and the conventional CTA particle illustrated in FIGS. 29A and 29B shows that the conventional CTA particle has a higher density, lower surface area, lower porosity, and larger particle size than the inventive CTA particles. In fact, the conventional CTA represented in FIGS. 29A and 29B has a mean particle size of about 205 microns and a BET surface area of about 0.57 m²/g.

FIG. 30 illustrates a conventional process for making purified terephthalic acid (PTA). In the conventional PTA process, para-xylene is partially oxidized in a mechanically agitated high temperature oxidation reactor 700. A slurry comprising CTA is withdrawn from reactor 700 and then purified in a purification system 702. The PTA product of purification system 702 is introduced into a separation system 706 for separation and drying of the PTA particles. Purification system 702 represents a large portion of the costs associated with producing PTA particles by conventional methods. Purification system 702 generally includes a water addition/exchange system 708, a dissolution system 710, a hydrogenation system 712, and three separate crystallization vessels 704a,b,c. In water addition/exchange system 708, a substantial portion of the mother liquor is displaced with water. After water addition, the water/CTA slurry is introduced into the dissolution system 710 where the water/CTA mixture is heated until the CTA particles fully dissolve in the water. After CTA dissolution, the CTA-in-water solution is subjected to hydrogenation in hydrogenation system 712. The hydrogenated effluent from hydrogenation system 712 is then subjected to three crystallization steps in crystallization vessels 704a,b,c, followed by PTA separation in separation system 706.

FIG. 31 illustrates an improved process for producing PTA employing a oxidation reactor system comprising a primary oxidation reactor 800a and a secondary oxidation reactor 800b. In the configuration illustrated in FIG. 31, an initial slurry is produced from primary oxidation reactor 800a and is thereafter subjected to purification in a purification system 802, of which secondary oxidation reactor 800b is a part. The initial slurry withdrawn from primary oxidation reactor 800a preferably comprises solid CTA particles and a liquid mother liquor. Typically, the initial slurry contains in the range of from about 10 to about 50 weight percent solid CTA particles, with the balance being liquid mother liquor. The solid CTA particles present in the initial slurry withdrawn from primary oxidation reactor 800a typically contain at least about 400 ppmw of 4-carboxybenzaldehyde (4-CBA), more typically at least about 800 ppmw of 4-CBA, and most typically in the range of from 1,000 to 15,000 ppmw of 4-CBA.

Purification system 802 receives the initial slurry withdrawn from primary oxidation reactor 800a and reduces the concentration of 4-CBA and other impurities present in the CTA. A purer/purified slurry is produced from purification system 802 and is subjected to separation and drying in a separation system 804 to thereby produce purer solid terephthalic acid particles comprising less than about 400 ppmw of 4-CBA, more preferably less than about 250 ppmw of 4-CBA, and most preferably in the range of from 10 to 200 ppmw of 4-CBA.

Purification system 802 includes secondary oxidation reactor 800b, a liquor exchange system 806, a digester 808, and a single crystallizer 810. In secondary oxidation reactor 800b, the initial slurry is subjected to oxidation at a temperature and pressure that are approximately equal to the temperature and pressure in primary oxidation reactor 800a. In liquor exchange system 806, at least about 50 weight percent of the mother liquor present in the slurry withdrawn from secondary oxidation reactor 800b is replaced with a fresh replacement solvent to thereby provide a solvent-exchanged slurry comprising CTA particles and the replacement solvent. The solvent-exchanged slurry exiting liquor exchange system 806 is introduced into digester 808. In digester 808, a further oxidation reaction is preformed at slightly higher temperatures than were used in primary oxidation reactor 800a.

As discussed above, the high surface area, small particle size, and low density of the CTA particles produced in primary oxidation reactor 800a cause certain impurities trapped in the CTA particles to become available for oxidation in digester 808 without requiring complete dissolution of the CTA particles in digester 808. Thus, the temperature in digester 808 can be lower than many similar prior art processes. The further oxidation carried out in digester 808 preferably reduces the concentration of 4-CBA in the CTA by at least 200 ppmw, more preferably at least about 400 ppmw, and most preferably in the range of from 600 to 6,000 ppmw. Preferably, the digestion temperature in digester 808 is at least about 10° C. higher than the primary oxidation temperature in reactor 800a, more preferably about 20 to about 80° C. higher than the primary oxidation temperature in reactor 800a, and most preferably 30 to 50° C. higher than the primary oxidation temperature in reactor 800a. The digestion temperature is preferably in the range of from about 160 to about 240° C., more preferably in the range of from about 180 to about 220° C. and most preferably in the range of from 190 to 210° C. The purified product from digester 808 requires only a single crystallization step in crystallizer 810 prior to separation in separation system 804. Suitable secondary oxidation/digestion techniques are discussed in further detail in U.S. Pat. App. Pub. No. 2005/0065373, the entire disclosure of which is expressly incorporated herein by reference.

Terephthalic acid (e.g., PTA) produced by the system illustrated in FIG. 31 is preferably formed of PTA particles having a mean particle size of at least about 40 microns, more preferably in the range of from about 50 to about 2,000 microns, and most preferably in the range of from 60 to 200 microns. The PTA particles preferably have an average BET surface area less than about 0.25 m²/g, more preferably in the range of from about 0.005 to about 0.2 m²/g, and most preferably in the range of from 0.01 to 0.18 m²/g. PTA produced by the system illustrated in FIG. 31 is suitable for use as a feedstock in the making of PET. Typically, PET is made via esterification of terephthalic acid with ethylene glycol, followed by polycondensation. Preferably, terephthalic acid produced by an embodiment of the present invention is employed as a feed to the pipe reactor PET process described in U.S. patent application Ser. No. 10/013,318, filed Dec. 7, 2001, the entire disclosure of which is incorporated herein by reference.

CTA particles with the preferred morphology disclosed herein are particularly useful in the above-described oxidative digestion process for reduction of 4-CBA content. In addition, these preferred CTA particles provide advantages in a wide range of other post-processes involving dissolution and/or chemical reaction of the particles. These additional post-processes include, but are not limited too, reaction with at least one hydroxyl-containing compound to form ester compounds, especially the reaction of CTA with methanol to form dimethyl terephthalate and impurity esters; reaction with at least one diol to form ester monomer and/or polymer compounds, especially the reaction of CTA with ethylene glycol to form polyethylene terephthalate (PET); and full or partial dissolution in solvents, including, but not limited too, water, acetic acid, and N-methyl-2-pyrrolidone, which may include further processing, including, but not limited too, reprecipitation of a more pure terephthalic acid and/or selective chemical reduction of carbonyl groups other than carboxylic acid groups. Notably included is the substantial dissolution of CTA in a solvent comprising water coupled with partial hydrogenation that reduces the amount of aldehydes, especially 4-CBA, fluorenones, phenones, and/or anthraquinones.

In accordance with one embodiment of the present invention, there is provided a process for partially oxidizing an oxidizable aromatic compound to one or more types of aromatic carboxylic acid wherein the purity of the solvent portion of the feed (i.e., the "solvent feed") and the purity of the oxidizable compound portion of the feed (i.e., the "oxidizable compound feed") are controlled within certain ranges specified below. Along with other embodiments of the present invention, this enables the purity of the liquid phase and, if present, the solid phase and the combined slurry (i.e., solid plus liquid) phase of the reaction medium to be controlled in certain preferred ranges, outlined below.

With respect to the solvent feed, it is known to oxidize an oxidizable aromatic compound(s) to produce an aromatic carboxylic acid wherein the solvent feed introduced into the reaction medium is a mixture of analytical-purity acetic acid and water, as is often employed at laboratory scale and pilot scale. Likewise, it is known to conduct the oxidation of oxidizable aromatic compound to aromatic carboxylic acid wherein the solvent leaving the reaction medium is separated from the produced aromatic carboxylic acid and then recycled back to the reaction medium as feed solvent, primarily for reasons of manufacturing cost. This solvent recycling causes certain feed impurities and process by-products to accumulate over time in the recycled solvent. Various means are known in the art to help purify recycled solvent before re-introduction into the reaction medium. Generally, a higher degree of purification of the recycled solvent leads to significantly higher manufacturing cost than does a lower degree of purification by similar means. One embodiment of the present invention relates to understanding and defining the preferred ranges of a large number of impurities within the solvent feed, many of which were heretofore thought largely benign, in order to find an optimal balance between overall manufacturing cost and overall product purity.

"Recycled solvent feed" is defined herein as solvent feed that was previously part of a reaction medium subjected to oxidation in an oxidation zone/reactor and exited the oxidation zone/reactor as part of the crude liquid and/or slurry product. For example, recycled solvent feed to a partial oxidation reaction medium for oxidizing para-xylene to form TPA is solvent that originally formed part of the partial oxidation reaction medium, was removed from the reaction medium as a liquid phase of a TPA slurry, was separated away from most solid TPA mass, and was then returned to the partial oxidation reaction medium. As described above, such recycled solvent feed is prone to accumulate all manner of undesirable impurities unless specific auxiliary process steps are provided for solvent purification, at considerable capital and operating cost. For economic reasons, it is preferable that at least about 20 weight percent of the solvent feed to the reaction medium of the present invention is recycled solvent, more preferably at least about 40 weight percent, still more preferably at least about 80 weight percent, and most preferably at least 90 weight percent. For reasons of solvent inventory and of on-stream time in a manufacturing unit, it is preferable that portions of recycled solvent pass through reaction medium at least once per day of operation, more preferably at least once per day for at least seven consecutive days of operation, and most preferably at least once per day for at least 30 consecutive days of operation.

The inventors have discovered that, for reasons of reaction activity and for consideration of metallic impurities left in the oxidation product, the concentrations of selected multivalent metals within the recycled solvent feed are preferably in ranges specified immediately below. The concentration of iron in recycled solvent is preferably below about 150 ppmw, more preferably below about 40 ppmw, and most preferably between 0 and 8 ppmw. The concentration of nickel in recycled solvent is preferably below about 150 ppmw, more preferably below about 40 ppmw, and most preferably between 0 and 8 ppmw. The concentration of chromium in recycled solvent is preferably below about 150 ppmw, more preferably below about 40 ppmw, and most preferably between 0 and 8 ppmw. The concentration of molybdenum in recycled solvent is preferably below about 75 ppmw, more preferably below about 20 ppmw, and most preferably between 0 and 4 ppmw. The concentration of titanium in recycled solvent is preferably below about 75 ppmw, more preferably below about 20 ppmw, and most preferably between 0 and 4 ppmw. The concentration of copper in recycled solvent is preferably below about 20 ppmw, more preferably below about 4 ppmw, and most preferably between 0 and 1 ppmw. Other metallic impurities are also typically present in recycled solvent, generally varying at lower levels in proportion to one or more of the above listed metals. Controlling the above listed metals in the preferred ranges will keep other metallic impurities at suitable levels.

These metals can arise as impurities in any of the incoming process feeds (e.g., in incoming oxidizable compound, solvent, oxidant, and catalyst compounds). Alternatively, the metals can arise as corrosion products from any of the process units contacting reaction medium and/or contacting recycled solvent. The means for controlling the metals in the disclosed concentration ranges include the appropriate specification and monitoring of the purity of various feeds and the appropriate usage of materials of construction, including, but not limited to, many commercial grades of titanium and of stainless steels including those grades known as duplex stainless steels and high molybdenum stainless steels.

The inventors have also discovered preferred ranges for selected aromatic compounds in the recycled solvent. These include both precipitated and dissolved aromatic compounds within the recycled solvent.

Surprisingly, even precipitated product (e.g., TPA) from a partial oxidation of para-xylene, is a contaminant to be managed in recycled solvent. Because there are surprisingly preferred ranges for the levels of solids within the reaction medium, any precipitated product in the solvent feed directly subtracts from the amount of oxidizable compound that can be fed in concert.

Furthermore, feeding precipitated TPA solids in the recycled solvent at elevated levels has been discovered to affect adversely the character of the particles formed within a precipitating oxidation medium, leading to undesirable character in downstream operations (e.g., product filtration, solvent washing, oxidative digestion of crude product, dissolution of crude product for further processing, and so on). Another undesirable characteristic of precipitated solids in the recycle solvent feed is that these often contain very high levels of precipitated impurities, as compared to impurity concentrations in the bulk of the solids within the TPA slurries from which much of the recycled solvent is obtained. Possibly, the elevated levels of impurities observed in solids suspended in recycled solvent may relate to nucleation times for precipitation of certain impurities from the recycled solvent and/or to cooling of the recycled solvent, whether intentional or due to ambient losses. For example, concentrations of highly-colored and undesirable 2,6-dicarboxyfluorenone have been observed at far higher levels in solids present in recycled solvent at 80° C. than are observed in TPA solids separated from recycled solvent at 160° C. Similarly, concentrations of isophthalic acid have been observed at much higher levels in solids present in recycled solvent compared to levels observed in TPA solids from the reaction medium. Exactly how specific precipitated impurities entrained within recycled solvent behave when re-introduced to the reaction medium appears to vary. This depends perhaps upon the relative solubility of the impurity within the liquid phase of the reaction medium, perhaps upon how the precipitated impurity is layered within the precipitated solids, and perhaps upon the local rate of TPA precipitation where the solid first re-enters the reaction medium. Thus, the inventors have found it useful to control the level of certain impurities in the recycled solvent, as disclosed below, without respect to whether these impurities are present in the recycled solvent in dissolved form or are entrained particulates therein.

The amount of precipitated solids present in recycled solvent is determined by a gravimetric method as follows. A representative sample is withdrawn from the solvent supply to the reaction medium while the solvent is flowing in a conduit toward the reaction medium. A useful sample size is about 100 grams captured in a glass container having about 250 milliliters of internal volume. Before being released to atmospheric pressure, but while continuously flowing toward the sample container, the recycled solvent is cooled to less than 100° C.; this cooling is in order to limit solvent evaporation during the short interval before being sealed closed in the glass container. After the sample is captured at atmospheric pressure, the glass container is sealed closed immediately. Then the sample is allowed to cool to about 20° C. while surrounded by air at about 20° C. and without forced convection. After reaching about 20° C., the sample is held at this condition for at least about 2 hours. Then, the sealed container is shaken vigorously until a visibly uniform distribution of solids is obtained Immediately thereafter, a magnetic stirrer bar is added to the sample container and rotated at sufficient speed to maintain effectively uniform distribution of solids. A 10 milliliter aliquot of the mixed liquid with suspended solids is withdrawn by pipette and weighed. Then the bulk of the liquid phase from this aliquot is separated by vacuum filtration, still at about 20° C. and effectively without loss of solids. The moist solids filtered from this aliquot are then dried, effectively without sublimation of solids, and these dried solids are weighed. The ratio of the weight of the dried solids to the weight of the original aliquot of slurry is the fraction of solids, typically expressed as a percentage and referred to herein as the amount of "precipitated solids at 20° C." in the solvent feed.

The inventors have discovered that aromatic compounds dissolved in the liquid phase of the reaction medium and comprising aromatic carboxylic acids lacking non-aromatic hydrocarbyl groups (e.g., isophthalic acid, benzoic acid, phthalic acid, 2,5,4'-tricarboxybiphenyl) are surprisingly pernicious components. Although these compounds are much reduced in chemical activity in the subject reaction medium compared to oxidizable compounds having non-aromatic hydrocarbyl groups, the inventors have discovered that these compounds nonetheless undergo numerous detrimental reactions. Thus, it is advantageous to control the content of these compounds in preferred ranges in the liquid phase of the reaction medium. This leads to preferred ranges of select compounds in recycled solvent feed and also to preferred ranges of select precursors in the oxidizable aromatic compound feed.

For example, in the liquid-phase partial oxidation of para-xylene to terephthalic acid (TPA), the inventors have discovered that the highly-colored and undesirable impurity 2,7-dicarboxyfluorenone (2,7-DCF) is virtually undetectable in the reaction medium and product off-take when meta-substituted aromatic compounds are at very low levels in the reaction medium. The inventors have discovered that when isophthalic acid impurity is present at increasing levels in the solvent feed, the formation of 2,7-DCF rises in almost direct proportion. The inventors have also discovered that when meta-xylene impurity is present in the feed of para-xylene, the formation of 2,7-DCF again rises almost in direct proportion. Furthermore, even if the solvent feed and oxidizable compound feed are devoid of meta-substituted aromatic compounds, the inventors have discovered that some isophthalic acid is formed during a typical partial oxidation of very pure para-xylene, particularly when benzoic acid is present in the liquid phase of the reaction medium. This self-generated isophthalic acid may, owing to its greater solubility than TPA in solvent comprising acetic acid and water, build up over time in commercial units employing recycled solvent. Thus, the amount of isophthalic acid within solvent feed, the amount of meta-xylene within oxidizable aromatic compound feed, and the rate of self-creation of isophthalic acid within the reaction medium are all appropriately considered in balance with each other and in balance with any reactions that consume isophthalic acid. Isophthalic acid has been discovered to undergo additional consumptive reactions besides the formation of 2,7-DCF, as are disclosed below. In addition, the inventors have discovered that there are other issues to consider when setting appropriate ranges for the meta-substituted aromatic species in the partial oxidation of para-xylene to TPA. Other highly-colored and undesirable impurities, such as 2,6-dicarboxyfluorenone (2,6-DCF), appear to relate greatly to dissolved, para-substituted aromatic species, which are always present with para-xylene feed to a liquid-phase oxidation. Thus, the suppression of 2,7-DCF is best considered in perspective with the level of other colored impurities being produced.

For example, in the liquid-phase partial oxidation of para-xylene to TPA, the inventors have discovered that the formation of trimellitic acid rises as the levels isophthalic acid and phthalic acid rise within the reaction medium. Trimellitic acid is a tri-functional carboxylic acid leading to branching of polymer chains during production of PET from TPA. In many PET applications, branching levels must be controlled to low levels and hence trimellitic acid must be controlled to low levels in purified TPA. Besides leading to trimellitic acid, the presence of meta-substituted and ortho-substituted species in the reaction medium also give rise to other tricarboxylic acids (e.g., 1,3,5-tricarboxybenzene). Furthermore, the increased presence of tricarboxylic acids in the reaction medium increases the amount of tetracarboxylic acid formation (e.g., 1,2,4,5-tetracarboxybenzene). Controlling the summed production of all aromatic carboxylic acids having more than two carboxylic acid groups is one factor in setting the preferred levels of meta-substituted and ortho-substituted species in the recycled solvent feed, in the oxidizable compound feed, and in the reaction medium according to the present invention.

For example, in the liquid-phase partial oxidation of para-xylene to TPA, the inventors have discovered that increased levels in the liquid phase of the reaction medium of several dissolved aromatic carboxylic acids lacking non-aromatic hydrocarbyl groups leads directly to the increased production of carbon monoxide and carbon dioxide. This increased production of carbon oxides represents a yield loss on both oxidant and on oxidizable compound, the later since many of the co-produced aromatic carboxylic acids, which on the one hand may be viewed as impurities, on the other hand also have commercial value. Thus, appropriate removal of relatively soluble carboxylic acids lacking non-aromatic hydrocarbyl groups from recycle solvent has an economic value in preventing yield loss of oxidizable aromatic compound and of oxidant, in addition to suppressing the generation of highly undesirable impurities such as various fluorenones and trimellitic acid.

For example, in the liquid-phase partial oxidation of para-xylene to TPA, the inventors have discovered that formation of 2,5,4'-tricarboxybiphenyl is seemingly unavoidable. The 2,5,4'-tricarboxybiphenyl is an aromatic tricarboxylic acid formed by the coupling of two aromatic rings, perhaps by the coupling of a dissolved para-substituted aromatic species with an aryl radical, perhaps an aryl radical formed by decarboxylation or decarbonylation of a para-substituted aromatic species. Fortunately, the 2,5,4'-tricarboxybiphenyl is typically produced at lower levels than trimellitic acid and does not usually lead to significantly increased difficulties with branching of polymer molecules during production of PET. However, the inventors have discovered that elevated levels of 2,5,4'-tricarboxybiphenyl in a reaction medium comprising oxidation of alkyl aromatics according to preferred embodiments of the present invention lead to increased levels of highly-colored and undesirable 2,6-DCF. The increased 2,6-DCF is possibly created from the 2,5,4'-tricarboxybiphenyl by ring closure with loss of a water molecule, though the exact reaction mechanism is not known with certainty. If 2,5,4'-tricarboxybiphenyl, which is more soluble in solvent comprising acetic acid and water than is TPA, is allowed to build up too high within recycled solvent, conversion rates to 2,6-DCF can become unacceptably large.

For example, in the liquid-phase partial oxidation of para-xylene to TPA, the inventors have discovered that aromatic carboxylic acids lacking non-aromatic hydrocarbyl groups (e.g., isophthalic acid) generally lead to mild suppression of the chemical activity of the reaction medium when present in the liquid phase at sufficient concentration.

For example, in the liquid-phase partial oxidation of para-xylene to TPA, the inventors have discovered that precipitation is very often non-ideal (i.e. non-equilibrium) with respect to the relative concentrations of different chemical species in the solid phase and in the liquid phase. Perhaps, this is because the precipitation rate is very fast at the space-time reaction rates preferred herein, leading to non-ideal co-precipitation of impurities, or even occlusion. Thus, when it is desired to limit the concentration of certain impurities (e.g., trimellitic acid and 2,6-DCF) within crude TPA, owing to the configuration of downstream unit operations, it is preferable to control their concentration in solvent feed as well as their generation rate within the reaction medium.

For example, the inventors have discovered that benzophenone compounds (e.g., 4,4'-dicarboxybenzophenone and 2,5, 4'-tricarboxybenzophenone) made during partial oxidation of para-xylene, have undesirable effects in a PET reaction medium even though benzophenone compounds are not as highly colored in TPA per se as are fluorenones and anthraquinones. Accordingly, it is desirable to limit the presence of benzophenones and select precursors in recycled solvent and in oxidizable compound feed. Furthermore, the inventors have discovered that the presence of elevated levels of benzoic acid, whether admitted in recycled solvent or formed within the reaction medium, leads to elevated rates of production of 4,4'-dicarboxybenzophenone.

In review, the inventors have discovered and sufficiently quantified a surprising array of reactions for aromatic compounds lacking non-aromatic hydrocarbyl groups that are present in the liquid-phase partial oxidation of para-xylene to TPA. Recapping just the single case of benzoic acid, the inventors have discovered that increased levels of benzoic acid in the reaction medium of certain embodiments of the present invention lead to greatly increased production of the highly colored and undesirable 9-fluorenone-2-carboxylic acid, to greatly increased levels of 4,4'-dicarboxybiphenyl, to increased levels of 4,4'-dicarboxybenzophenone, to a mild suppression of chemical activity of the intended oxidation of para-xylene, and to increased levels of carbon oxides and attendant yield losses. The inventors have discovered that increased levels of benzoic acid in the reaction medium also lead to increased production of isophthalic acid and phthalic acid, the levels of which are desirably controlled in low ranges according to similar aspects of the current invention. The number and importance of reactions involving benzoic acid are perhaps even more surprising since some recent inventors contemplate using benzoic acid in place of acetic acid as a primary component of solvent (See, e.g., U.S. Pat. No. 6,562,997). Additionally, the present inventors have observed that benzoic acid is self-generated during oxidation of para-xylene at rates that are quite important relative to its formation from impurities, such as toluene and ethylbenzene, commonly found in oxidizable compound feed comprising commercial-purity para-xylene.

On the other hand, the inventors have discovered little value from additional regulation of recycled solvent composition in regard to the presence of oxidizable aromatic compound and in regard to aromatic reaction intermediates that both retain non-aromatic hydrocarbyl groups and are also relatively soluble in the recycled solvent. In general, these compounds are either fed to or created within the reaction medium at rates substantially greater than their presence in recycled solvent; and the consumption rate of these compounds within the reaction medium is great enough, retaining one or more non-aromatic hydrocarbyl groups, to limit appropriately their build-up within recycled solvent. For example, during partial oxidation of para-xylene in a multi-phase reaction medium, para-xylene evaporates to a limited extent along with large quantities of solvent. When this evaporated solvent exits the reactor as part of the off-gas and is condensed for recovery as recycled solvent, a substantial portion of the evaporated para-xylene condenses therein as well. It is not necessary to limit the concentration of this para-xylene in recycled solvent. For example, if solvent is separated from solids upon slurry exiting a para-xylene oxidation reaction medium, this recovered solvent will contain a similar concentration of dissolved para-toluic acid to that present at the point of removal from the reaction medium. Although it may be important to limit the standing concentration of para-toluic acid within the liquid phase of the reaction medium, see below, it is not necessary to regulate separately the para-toluic acid in this portion of recycled solvent owing to its relatively good solubility and to its low mass flow rate relative to the creation of para-toluic acid within the reaction medium. Similarly, the inventors have discovered little reason to limit the concentrations in recycled solvent of aromatic compounds with methyl substituents (e.g. toluic acids), aromatic aldehydes (e.g., terephthaldehyde), of aromatic compounds with hydroxy-methyl substituents (e.g., 4-hydroxymethylbenzoic acid), and of brominated aromatic compounds retaining at least one non-aromatic hydrocarbyl group (e.g., alpha-bromo-para-toluic acid) below those inherently found in the liquid phase exiting from the reaction medium occurring in the partial oxidation of xylene according to preferred embodiments of the present invention. Surprisingly, the inventors have also discovered that it is also not necessary to regulate in recycled solvent the concentration of selected phenols intrinsically produced during partial oxidation of xylene, for these compounds are created and destroyed within the reaction medium at rates much greater than their presence in recycled solvent. For example, the inventors have discovered that 4-hydroxybenzoic acid has relatively small effects on chemical activity in the preferred embodiments of the present invention when co-fed at rates of over 2 grams of 4-hydroxybenzoic acid per 1 kilogram of para-xylene, far higher than the natural presence in recycled solvent, despite being reported by others as a significant poison in similar reaction medium (See, e.g., W. Partenheimer, Catalysis Today 23 (1995) p. 81).

Thus, there are numerous reactions and numerous considerations in setting the preferred ranges of various aromatic impurities in the solvent feed as now disclosed. These discoveries are stated in terms of the aggregated weight average composition of all solvent streams being fed to the reaction medium during the course of a set time period, preferably one day, more preferably one hour, and most preferably one minute. For example, if one solvent feed flows substantially continuously with a composition of 40 ppmw of isophthalic acid at a flow rate of 7 kilograms per minute, a second solvent feed flows substantially continuously with a composition of 2,000 ppmw of isophthalic acid at a flow rate of 10 kilograms per minute, and there are no other solvent feed streams entering the reaction medium, then the aggregated weight average composition of the solvent feed is calculated as (40*7+2,000*10)/(7+10)=1,193 ppmw of isophthalic acid. It is notable that the weight of any oxidizable compound feed or of any oxidant feed that are perhaps commingled with the solvent feed before entering the reaction medium are not considered in calculating the aggregated weight average composition of the solvent feed.

Table 1, below, lists preferred values for certain components in the solvent feed introduced into the reaction medium. The solvent feed components listed in Table 1 are as follows: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), total fluorenones including other fluorenones not individually listed (total fluorenones), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP), terephthalic acid (TPA), precipitated solids at 20° C., and total aromatic carboxylic acids lacking non-aromatic hydrocarbyl groups. Table 1, below provides the preferred amounts of these impurities in CTA produced according to an embodiment of the present invention.

TABLE 1

Components of Solvent Feed Introduced into Reaction Medium

| Component Identification | Preferred Amt. (ppmw) | More Preferred Amt. (ppmw) | Most Preferred Amt. (ppmw) |
|---|---|---|---|
| 4-CBA | <1,200 | 30-600 | 60-300 |
| 4,4'-DCS | <3 | <2 | <1 |
| 2,6-DCA | <6 | 0.1-3 | 0.2-1 |
| 2,6-DCF | <20 | 0.1-10 | 0.5-5 |
| 2,7-DCF | <10 | 0.1-5 | 0.5-2 |
| 3,5-DCF | <10 | <5 | <2 |

TABLE 1-continued

Components of Solvent Feed Introduced into Reaction Medium

| Component Identification | Preferred Amt. (ppmw) | More Preferred Amt. (ppmw) | Most Preferred Amt. (ppmw) |
|---|---|---|---|
| 9F-2CA | <10 | 0.1-5 | 0.5-2 |
| 9F-4CA | <5 | <3 | <1 |
| Total fluorenones | <40 | <20 | 1-8 |
| 4,4'-DCB | <45 | <15 | 0.5-5 |
| 2,5,4'-TCB | <45 | 0.1-15 | 0.5-5 |
| PA | <1,000 | 15-400 | 40-150 |
| IPA | 2,500 | 40-1,200 | 120-400 |
| BA | <4,500 | 50-1,500 | 150-500 |
| TMA | <1,000 | 15-400 | 40-150 |
| 2,6-DCBC | <40 | <20 | <5 |
| 4,4'-DCBZ | <40 | <20 | <5 |
| 4,4'-DCBP | <40 | <20 | <5 |
| 2,5,4'-TCBP | <40 | <20 | 0.5-5 |
| TPA | <9,000 | 200-6,000 | 400-2,000 |
| Precipitated Solids at 20° C. | <9,000 | 200-6,000 | 600-2,000 |
| Total Aromatic Carboxylic Acids Lacking Non-Aromatic Hydrocarbyl Groups | <18,000 | 300-9,000 | 450-3,000 |

Many other aromatic impurities are also typically present in recycled solvent, generally varying at even lower levels and/or in proportion to one or more of the disclosed aromatic compounds. Methods for controlling the disclosed aromatic compounds in the preferred ranges will typically keep other aromatic impurities at suitable levels.

When bromine is used within the reaction medium, a large number of ionic and organic forms of bromine are known to exist in a dynamic equilibrium. These various forms of bromine have different stability characteristics once leaving the reaction medium and passing through various unit operations pertaining to recycled solvent. For example, alpha-bromo-para-toluic acid may persist as such at some conditions or may rapidly hydrolyze at other conditions to form 4-hydroxymethylbenzoic acid and hydrogen bromide. In the present invention, it is preferable that at least about 40 weight percent, more preferable that at least about 60 weight percent, and most preferable that at least about 80 weight percent of the total mass of bromine present in the aggregated solvent feed to the reaction medium is in one or more of the following chemical forms: ionic bromine, alpha-bromo-para-toluic acid, and bromoacetic acid.

Although the importance and value of controlling the aggregated weight average purity of solvent feed within the disclosed, desired ranges of the present invention has not heretofore been discovered and/or disclosed, suitable means for controlling the solvent feed purity may be assembled from various methods already known in the art. First, any solvent evaporated from the reaction medium is typically of suitable purity providing that liquid or solids from the reaction medium are not entrained with the evaporated solvent. The feeding of reflux solvent droplets into the off-gas disengaging space above the reaction medium, as disclosed herein, appropriately limits such entrainment; and recycled solvent of suitable purity with respect to aromatic compound can be condensed from such off-gas. Second, the more difficult and costly purification of recycled solvent feed typically relates to solvent taken from the reaction medium in liquid form and to solvent that subsequently contacts the liquid and/or solid phases of the reaction medium withdrawn from the reaction vessel (e.g., recycled solvent obtained from a filter in which solids are concentrated and/or washed, recycled solvent obtained from a centrifuge in which solids are concentrated and/or washed, recycled solvent taken from a crystallization operation, and so on). However, means are also known in the art for effecting the necessary purification of these recycled solvent streams using one or more prior disclosures. With respect to controlling precipitated solids in recycled solvent to be within the ranges specified, suitable control means include, but are not limited to, gravimetric sedimentation, mechanical filtration using filter cloth on rotary belt filters and rotary drum filters, mechanical filtration using stationary filter medium within pressure vessels, hydro-cyclones, and centrifuges. With respect to controlling dissolved aromatic species in recycled solvent to be within the ranges specified, the control means include, but are not limited to, those disclosed in U.S. Pat. No. 4,939,297 and U.S. Pat. App. Pub. No. 2005-0038288, incorporated herein by reference. However, none of these prior inventions discovered and disclosed the preferred levels of purity in the aggregated solvent feed as disclosed herein. Rather, these prior inventions merely provided means to purify selected and partial streams of recycled solvent without deducing the present inventive, optimal values of the composition of the aggregated weight average solvent feed to the reaction medium.

Turning now to the purity of the feed of oxidizable compound, it is known that certain levels of isophthalic acid, phthalic acid, and benzoic acid are present and tolerable at low levels in purified TPA used for polymer production. Moreover, it is known these species are relatively more soluble in many solvents and may be advantageously removed from purified TPA by crystallization processes. However, from an embodiment of the invention disclosed herein, it is now known that controlling the level of several relatively soluble aromatic species, notably including isophthalic acid, phthalic acid, and benzoic acid, in the liquid phase of the reaction medium is surprisingly important for controlling the level of polycyclic and colored aromatic compounds created in the reaction medium, for controlling compounds with more than 2 carboxylic acid functions per molecule, for controlling reaction activity within the partial oxidation reaction medium, and for controlling yield losses of oxidant and of aromatic compound.

It is known within the art that isophthalic acid, phthalic acid, and benzoic acid are formed in the reaction medium as follows. Meta-Xylene feed impurity oxidizes in good conversion and yield to IPA. Ortho-Xylene feed impurity oxidizes in good conversion and yield to phthalic acid. Ethylbenzene and toluene feed impurities oxidize in good conversion and yield to benzoic acid. However, the inventors have observed that significant amounts of isophthalic acid, phthalic acid, and benzoic acid are also formed within a reaction medium comprising para-xylene by means other than oxidation of meta-xylene, ortho-xylene, ethylbenzene, and toluene. These other intrinsic chemical routes possibly include decarbonylation, decarboxylation, the re-organization of transition states, and addition of methyl and carbonyl radicals to aromatic rings.

In determining preferred ranges of impurities in the feed of oxidizable compound, many factors are relevant. Any impurity in the feed is likely to be a direct yield loss and a product purification cost if the purity requirements of the oxidized product are sufficiently strict (e.g., in a reaction medium for partial oxidation of para-xylene, toluene and ethylbenzene typically found in commercial-purity para-xylene lead to benzoic acid, and this benzoic acid is largely removed from most commercial TPA). When the partial oxidation product of a feed impurity participates in additional reactions, factors other than simple yield loss and removal become appropriate when considering how much feed purification cost to incur (e.g., in a reaction medium for partial oxidation of para-xylene, ethylbenzene leads to benzoic acid, and benzoic acid subsequently leads to highly colored 9-fluorenone-2-carboxylic acid, to isophthalic acid, to phthalic acid, and to increased carbon oxides, among others). When the reaction medium self-generates additional amounts of an impurity by chemical mechanisms not directly related to feed impurities, the analysis becomes still more complex (e.g., in a reaction medium for partial oxidation of para-xylene, benzoic acid is also self-generated from para-xylene itself). In addition, the downstream processing of the crude oxidation product may affect the considerations for preferred feed purity. For example, the cost of removing to suitable levels a direct impurity (benzoic acid) and subsequent impurities (isophthalic acid, phthalic acid, 9-fluorenone-2-carboxylic acid, et al.) may be one and the same, may be different from each other, and may be different from the requirements of removing a largely unrelated impurity (e.g., incomplete oxidation product 4-CBA in the oxidation of para-xylene to TPA).

The following disclosed feed purity ranges for para-xylene are preferred where para-xylene is fed with solvent and oxidant to a reaction medium for partial oxidation to produce TPA. These ranges are more preferred in TPA production process having post-oxidation steps to remove from reaction medium impurities other than oxidant and solvent (e.g., catalyst metals). These ranges are still more preferred in TPA production processes that remove additional 4-CBA from CTA (e.g., by conversion of CTA to dimethyl terephthalate plus impurity esters and subsequent separation of the methyl ester of 4-CBA by distillation, by oxidative digestion methods for converting 4-CBA to TPA, by hydrogenation methods for converting 4-CBA to para-toluic acid, which is then separated by partial-crystallization methods). These ranges are most preferred in TPA production processes that remove additional 4-CBA from CTA by oxidative digestion methods for converting 4-CBA to TPA.

Using new knowledge of preferred ranges of recycling aromatic compounds and of the relative amounts of the aromatic compounds formed directly from oxidation of feed impurities as compared to other intrinsic chemical routes, improved ranges for impurities have been discovered for impure para-xylene being fed to a partial oxidation process for TPA production. Table 2 below provides preferred values for the amount of meta-xylene, ortho-xylene, and ethylbenzene+toluene in the para-xylene feed expressed in parts per million by weight of para-xylene.

TABLE 2

| Components of Impure para-xylene Feed | | | |
|---|---|---|---|
| Component Identification | Preferred Amt. (ppmw) | More Preferred Amt. (ppmw) | Most Preferred Amt. (ppmw) |
| meta-xylene | 20-800 | 50-600 | 100-400 |
| ortho-xylene | 10-300 | 20-200 | 30-100 |
| ethylbenzene + toluene* | 20-700 | 50-500 | 100-300 |
| total | 50-900 | 100-800 | 200-700 |

*Specification for ethylbenzene + toluene is each separately and in sum

Those skilled in the art will now recognize the above impurities within impure para-xylene may have their greatest effect on the reaction medium after their partial oxidation products have accumulated in recycled solvent. For example, feeding the upper amount of the most preferred range of meta-xylene, 400 ppmw, will immediately produce about 200 ppmw of isophthalic acid within the liquid phase of the reaction medium when operating with about 33 weight percent solids in the reaction medium. This compares with an input from the upper amount of the most preferred range for isophthalic acid in recycled solvent of 400 ppmw that, after allowing for a typical solvent evaporation to cool the reaction medium, amounts to about 1,200 ppmw of isophthalic acid within the liquid phase of the reaction medium. Thus, it is the accumulation of partial oxidation products over time within recycled solvent that represents the greatest probable impact of the meta-xylene, ortho-xylene, ethylbenzene, and toluene impurities in the feed of impure para-xylene. Accordingly, the above ranges for impurities in impure para-xylene feed are preferred to be maintained for at least one-half of each day of operation of any partial oxidation reaction medium in a particular manufacturing unit, more preferably for at least three-quarters of each day for at least seven consecutive days of operation, and most preferably when the mass-weighted averages of the impure para-xylene feed composition are within the preferred ranges for at least 30 consecutive days of operation.

Means for obtaining impure para-xylene of preferred purity are already known in the art and include, but are not limited to, distillation, partial crystallization methods at sub-ambient temperatures, and molecular sieve methods using selective pore-size adsorption. However, the preferred ranges of purity specified herein are, at their high end, more demanding and expensive than characteristically practiced by commercial suppliers of para-xylene; and yet at the low end, the preferred ranges avoid overly costly purification of para-xylene for feeding to a partial oxidation reaction medium by discovering and disclosing where the combined effects of impurity self-generation from para-xylene itself and of impurity consumptive reactions within the reaction medium become more important than the feed rates of impurities within impure para-xylene.

When the xylene-containing feed stream contains selected impurities, such as ethyl-benzene and/or toluene, oxidation of these impurities can generate benzoic acid. As used herein, the term "impurity-generated benzoic acid" shall denote benzoic acid derived from any source other than xylene during xylene oxidation.

As disclosed herein, a portion of the benzoic acid produced during xylene oxidation is derived from the xylene itself. This production of benzoic acid from xylene is distinctly in addition to any portion of benzoic acid production that may be impurity-generated benzoic acid. Without being bound by theory, it is believed that benzoic acid is derived from xylene within the reaction medium when various intermediate oxidation products of xylene spontaneously decarbonylate (carbon monoxide loss) or decarboxylate (carbon dioxide loss) to thereby produce aryl radicals. These aryl radicals can then abstract a hydrogen atom from one of many available sources in the reaction medium and produce self-generated benzoic acid. Whatever the chemical mechanism, the term "self-generated benzoic acid," as used herein, shall denote benzoic acid derived from xylene during xylene oxidation.

As also disclosed herein, when para-xylene is oxidized to produce terephthalic acid (TPA), the production of self-generated benzoic acid causes para-xylene yield loss and oxidant yield loss. In addition, the presence of self-generated benzoic acid in the liquid phase of the reaction medium correlates with increases for many undesirable side reactions, notably including generation of highly colored compounds called mono-carboxy-fluorenones. Self-generated benzoic acid also contributes to the undesirable accumulation of benzoic acid in recycled solvent, which further elevates the concentration of benzoic acid in the liquid phase of the reaction medium. Thus, formation of self-generated benzoic acid is desirably minimized, but this is also appropriately considered simultaneously with impurity-generated benzoic acid, with factors affecting consumption of benzoic acid, with factors pertaining to other issues of reaction selectivity, and with overall economics.

The inventors have discovered that the self-generation of benzoic acid can be controlled to low levels by appropriate selection of, for example, temperature, xylene distribution, and oxygen availability within the reaction medium during oxidation. Not wishing to be bound by theory, lower temperatures and improved oxygen availability appear to suppress the decarbonylation and/or decarboxylation rates, thus avoiding the yield loss aspect of self-generated benzoic acid. Sufficient oxygen availability appears to direct aryl radicals toward other more benign products, in particular hydroxybenzoic acids. Distribution of xylene in the reaction medium may also affect the balance between aryl radical conversion to benzoic acid or to hydroxybenzoic acids. Whatever the chemical mechanisms, the inventors have discovered reaction conditions that, although mild enough to reduce benzoic acid production, are severe enough to oxidize a high fraction of the hydroxybenzoic acid production to carbon monoxide and/or carbon dioxide, which are easily removed from the oxidation product.

In a preferred embodiment of the present invention, the oxidation reactor is configured and operated in a manner such that the formation of self-generated benzoic acid is minimized and the oxidation of hydroxybenzoic acids to carbon monoxide and/or carbon dioxide is maximized When the oxidation reactor is employed to oxidize para-xylene to terephthalic acid, it is preferred that para-xylene makes up at least about 50 weight percent of the total xylene in the feed stream introduced into the reactor. More preferably, para-xylene makes up at least about 75 weight percent of the total xylene in the feed stream. Still more preferably, para-xylene makes up at least 95 weight percent of the total xylene in the feed stream. Most preferably, para-xylene makes up substantially all of the total xylene in the feed stream.

When the reactor is employed to oxidize para-xylene to terephthalic acid, it is preferred for the rate of production of terephthalic acid to be maximized, while the rate of production of self-generated benzoic acid is minimized. Preferably, the ratio of the rate of production (by weight) of terephthalic acid to the rate of production (by weight) of self-generated benzoic acid is at least about 500:1, more preferably at least about 1,000:1, and most preferably at least 1,500:1. As will be seen below, the rate of production of self-generated benzoic acid is preferably measured when the concentration of benzoic acid in the liquid phase of the reaction medium is below 2,000 ppmw, more preferably below 1,000 ppmw, and most preferably below 500 ppmw, because these low concentrations suppress to suitably low rates reactions that convert benzoic acid to other compounds.

Combining the self-generated benzoic acid and the impurity-generated benzoic acid, the ratio of the rate of production (by weight) of terephthalic acid to the rate of production (by weight) of total (self-generated and impurity-generated) benzoic acid is preferably at least about 400:1, more preferably at least about 700:1, and most preferably at least 1,100:1. As will be seen below, the summed rate of production of self-generated benzoic acid plus impurity-generated benzoic acid is preferably measured when the concentration of benzoic acid in the liquid phase of the reaction medium is below 500 ppmw, because these low concentrations suppress to suitably low rates reactions that convert benzoic acid to other compounds.

As disclosed herein, elevated concentrations of benzoic acid in the liquid phase of the reaction medium lead to increased formation of many other aromatic compounds, several of which are noxious impurities in TPA; and, as disclosed herein, elevated concentrations of benzoic acid in the liquid phase of the reaction medium lead to increased formation of carbon oxide gases, the formation of which represents yield loss on oxidant and on aromatic compounds and/or solvent. Furthermore, it is now disclosed that the inventors have discovered a considerable portion of this increased formation of other aromatic compounds and of carbon oxides derives from reactions that convert some of the benzoic acid molecules themselves, as contrasted to benzoic acid catalyzing other reactions without itself being consumed. Accordingly, the "net generation of benzoic acid" is defined herein as the time-averaged weight of all benzoic acid exiting the reaction medium minus the time-averaged weight of all benzoic acid entering the reaction medium during the same period of time. This net generation of benzoic acid is often positive, driven by the formation rates of impurity-generated benzoic acid and of self-generated benzoic acid. However, the inventors have discovered that the conversion rate of benzoic acid to carbon oxides, and to several other compounds, appears to increase approximately linearly as the concentration of benzoic acid is increased in the liquid phase of the reaction medium, measured when other reaction conditions comprising temperature, oxygen availability, STR, and reaction activity are maintained appropriately constant. Thus, when the concentration of benzoic acid in the liquid-phase of the reaction medium is great enough, perhaps due to an elevated concentration of benzoic acid in recycled solvent, then the conversion of benzoic acid molecules to other compounds, including carbon oxides, can become equal to or greater than the chemical generation of new benzoic acid molecules. In this case, the net generation of benzoic acid can become balanced near zero or even negative. The inventors have discovered that when the net generation of benzoic acid is positive, then the ratio of the rate of production (by weight) of terephthalic acid in the reaction medium compared to the rate of net generation of benzoic acid in the reaction medium is preferably above about 700:1, more preferably above about 1,100:1, and most preferably above 4,000:1. The inventors have discovered that when the net generation of benzoic acid is negative, the ratio of the rate of production (by weight) of terephthalic acid in the reaction medium compared to the rate of net generation of benzoic acid in the reaction medium is preferably above about 200:(−1), more preferably above about 1,000:(−1), and most preferably above 5,000:(−1).

The inventors have also discovered preferred ranges for the composition of the slurry (liquid+solid) withdrawn from the reaction medium and for the solid CTA portion of the slurry. The preferred slurry and the preferred CTA compositions are surprisingly superior and useful. For example, purified TPA produced from this preferred CTA by oxidative digestion has a sufficiently low level of total impurities and of colored impurities such that the purified TPA is suitable, without hydrogenation of additional 4-CBA and/or colored impurities, for a wide range of applications in PET fibers and PET packaging applications. For example, the preferred slurry composition provides a liquid phase of the reaction medium that is relatively low in concentration of important impurities and this importantly reduces the creation of other even more undesirable impurities as disclosed herein. In addition, the preferred slurry composition importantly aids the subsequent processing of liquid from the slurry to become suitably pure recycled solvent, according to other embodiments of the present invention.

CTA produced according to one embodiment of the present invention contains less impurities of selected types than CTA produce by conventional processes and apparatuses, notably those employing recycled solvent. Impurities that may be present in CTA include the following: 4-carboxybenzaldehyde (4-CBA), 4,4'-dicarboxystilbene (4,4'-DCS), 2,6-dicarboxyanthraquinone (2,6-DCA), 2,6-dicarboxyfluorenone (2,6-DCF), 2,7-dicarboxyfluorenone (2,7-DCF), 3,5-dicarboxyfluorenone (3,5-DCF), 9-fluorenone-2-carboxylic acid (9F-2CA), 9-fluorenone-4-carboxylic acid (9F-4CA), total fluorenones including other fluorenones not individually listed (total fluorenones), 4,4'-dicarboxybiphenyl (4,4'-DCB), 2,5,4'-tricarboxybiphenyl (2,5,4'-TCB), phthalic acid (PA), isophthalic acid (IPA), benzoic acid (BA), trimellitic acid (TMA), para-toluic acid (PTAC), 2,6-dicarboxybenzocoumarin (2,6-DCBC), 4,4'-dicarboxybenzil (4,4'-DCBZ), 4,4'-dicarboxybenzophenone (4,4'-DCBP), 2,5,4'-tricarboxybenzophenone (2,5,4'-TCBP). Table 3, below provides the preferred amounts of these impurities in CTA produced according to an embodiment of the present invention.

TABLE 3

CTA Impurities

| Impurity Identification | Preferred Amt. (ppmw) | More Preferred Amt. (ppmw) | Most Preferred Amt. (ppmw) |
| --- | --- | --- | --- |
| 4-CBA | <15,000 | 100-8,000 | 400-2,000 |
| 4,4'-DCS | <12 | <6 | <3 |
| 2,6-DCA | <9 | <6 | <2 |
| 2,6-DCF | <100 | 2-50 | 5-25 |
| 2,7-DCF | <30 | <15 | <5 |
| 3,5-DCF | <16 | <8 | <2 |
| 9F-2CA | <16 | <8 | <4 |
| 9F-4CA | <8 | <4 | <2 |
| Total fluorenones | <100 | 2-60 | 4-35 |
| 4,4'-DCB | <64 | 1-32 | 2-8 |
| 2,5,4'-TCB | <24 | <12 | <8 |
| PA | <200 | 3-100 | 5-50 |
| IPA | <800 | 10-400 | 20-200 |
| BA | <600 | 5-300 | 15-100 |
| TMA | <800 | 10-400 | 20-200 |
| PTAC | <2,000 | 10-1,000 | 50-500 |
| 2,6-DCBC | <64 | <32 | <8 |
| 4,4'-DCBZ | <12 | <8 | <4 |
| 4,4'-DCBP | <40 | <30 | <20 |
| 2,5,4'-TCBP | <32 | <16 | <4 |

In addition, it is preferred for CTA produced according to an embodiment of the present invention to have reduced color content relative to CTA produce by conventional processes and apparatuses, notably those employing recycled solvent. Thus, it is preferred for CTA produced in accordance to one embodiment of the present invention to have a percent transmittance percent at 340 nanometers (nm) of at least about 25 percent, more preferably of at least about 50 percent, and most preferably of at least 60 percent. It is further preferred for CTA produced in accordance to one embodiment of the present invention to have a percent transmittance percent at 400 nanometers (nm) of at least about 88 percent, more preferably of at least about 90 percent, and most preferably of at least 92 percent.

The test for percent transmittance provides a measure of the colored, light-absorbing impurities present within TPA or CTA. As used herein, the test refers to measurements done on a portion of a solution prepared by dissolving 2.00 grams of dry solid TPA or CTA in 20.0 milliliters of dimethyl sulfoxide (DMSO), analytical grade or better. A portion of this solution is then placed in a Hellma semi-micro flow cell, PN 176.700, which is made of quartz and has a light path of 1.0 cm and a volume of 0.39 milliliters. (Hellma USA, 80 Skyline Drive, Plainview, N.Y. 11803). An Agilent 8453 Diode Array Spectrophotometer is used to measure the transmittance of different wavelengths of light through this filled flow cell. (Agilent Technologies, 395 Page Mill Road, Palo Alto, Calif. 94303). After appropriate correction for absorbance from the background, including but not limited to the cell and the solvent used, the percent transmittance results, characterizing the fraction of incident light that is transmitted through the solution, are reported directly by the machine. Percent transmittance values at light wavelengths of 340 nanometers and 400 nanometers are particularly useful for discriminating pure TPA from many of the impurities typically found therein.

The preferred ranges of various aromatic impurities in the slurry (solid+liquid) phase of the reaction medium are provided below in Table 4.

TABLE 4

Slurry Impurities

| Impurity Identification | Preferred Amt. (ppmw) | More Preferred Amt. (ppmw) | Most Preferred Amt. (ppmw) |
|---|---|---|---|
| 4-CBA | <8,000 | <5,000 | <2,500 |
| 4,4'-DCS | <4 | <2 | <1 |
| 2,6-DCA | <6 | <3 | <1 |
| 2,6-DCF | <70 | 2-40 | 4-20 |
| 2,7-DCF | <12 | <8 | <4 |
| 3,5-DCF | <12 | <8 | <4 |
| 9F-2CA | <12 | <8 | <4 |
| 9F-4CA | <8 | <4 | <2 |
| Total fluorenones | <90 | 2-60 | 5-30 |
| 4,4'-DCB | <64 | 1-16 | 2-4 |
| 2,5,4'-TCB | <60 | 2-40 | 4-20 |
| PA | <3,000 | 25-1,500 | 75-500 |
| IPA | 9,000 | 75-4,500 | 225-1,500 |
| BA | <15,000 | 100-6,000 | 300-2,000 |
| TMA | <3,000 | 25-1,500 | 75-500 |
| PTAC | <8,000 | 100-4,000 | 200-2,000 |
| 4,4'-DCBZ | <5 | <4 | <3 |
| 4,4'-DCBP | <240 | <160 | <80 |
| 2,5,4'-TCBP | <120 | <80 | <40 |

These preferred compositions for the slurry embody the preferred composition of the liquid phase of the reaction medium while usefully avoiding experimental difficulties pertaining to precipitation of additional liquid phase components from the reaction medium into solid phase components during sampling from the reaction medium, separation of liquids and solids, and shifting to analytical conditions.

Many other aromatic impurities are also typically present in the slurry phase of the reaction medium and in CTA of the reaction medium, generally varying at even lower levels and/or in proportion to one or more of the disclosed aromatic compounds. Controlling the disclosed aromatic compounds in the preferred ranges will keep other aromatic impurities at suitable levels. These advantaged compositions for the slurry phase in the reaction medium and for the solid CTA taken directly from the slurry are enabled by operating with embodiments of the invention disclosed herein for partial oxidation of para-xylene to TPA.

Measurement of the concentration of low level components in the solvent, recycled solvent, CTA, slurry from the reaction medium, and PTA are performed using liquid chromatography methods. Two interchangeable embodiments are now described.

The method referred to herein as HPLC-DAD comprises high pressure liquid chromatography (HPLC) coupled with a diode array detector (DAD) to provide separation and quantitation of various molecular species within a given sample. The instrument used in this measurement is a model 1100 HPLC equipped with a DAD, provided by Agilent Technologies (Palo Alto, Calif.), though other suitable instruments are also commercially available and from other suppliers As is known in the art, both the elution time and the detector response are calibrated using known compounds present in known amounts, compounds and amounts that are appropriate to those occurring in actual unknown samples.

The method referred to herein as HPLC-MS comprises high pressure liquid chromatography (HPLC) coupled with mass spectrometry (MS) to provide separation, identification, and quantitation of various molecular species within a given sample. The instruments used in this measurement is an Alliance HPLC and ZQ MS provided by Waters Corp. (Milford, Mass.), though other suitable instruments are also commercially available and from other suppliers. As is known in the art, both the elution time and the mass spectrometric response are calibrated using known compounds present in known amounts, compounds and amounts that are appropriate to those occurring in actual unknown samples.

Another embodiment of the current invention relates to partial oxidation of aromatic oxidizable compound with appropriate balancing of the suppression of noxious aromatic impurities on the one hand against the production of carbon dioxide and carbon monoxide, collectively carbon oxides (COx), on the other. These carbon oxides typically exit the reaction vessel in the off-gas, and they correspond to a destructive loss of solvent and of oxidizable compound, including the ultimately preferred oxidized derivatives (e.g., acetic acid, para-xylene, and TPA). The inventors have discovered lower bounds for the production of carbon oxides below which it seems the high creation of noxious aromatic impurities, as described below, and the low overall conversion level are inevitably too poor to be of economic utility. The inventors have also discovered upper bounds of carbon oxides above which the generation of carbon oxides continues to increase with little further value provided by reduction in generation of noxious aromatic impurities.

The inventors have discovered that reducing the liquid-phase concentrations of aromatic oxidizable compound feed and of aromatic intermediate species within a reaction medium leads to lower generation rates for noxious impurities during the partial oxidation of aromatic oxidizable compound. These noxious impurities include coupled aromatic rings and/or aromatic molecules containing more than the desired number of carboxylic acid groups (e.g., in the oxidation of para-xylene the noxious impurities include 2,6-dicarboxyanthraquinone, 2,6-dicarboxyfluorenone, trimellitic acid, 2,5,4'-tricarboxybiphenyl, and 2,5,4'-benzophenone). The aromatic intermediate species include aromatic compounds descended from the feed of oxidizable aromatic compound and still retaining non-aromatic hydrocarbyl groups (e.g., in the oxidation of para-xylene the aromatic intermediate species comprise para-tolualdehyde, terephthaldehyde, para-toluic acid, 4-CBA, 4-hydroxymethylbenzoic acid, and alpha-bromo-para-toluic acid). The aromatic oxidizable compound feed and the aromatic intermediate species retaining non-aromatic hydrocarbyl groups, when present in the liquid phase of the reaction medium, appear to lead to noxious impurities in a manner similar to that already disclosed herein for dissolved aromatic species lacking non-aromatic hydrocarbyl groups (e.g., isophthalic acid).

Set against this need for higher reaction activity to suppress formation of noxious aromatic impurities during partial oxidation of oxidizable aromatic compound, the inventors have discovered that the undesirable attendant result is increased production of carbon oxides. It is important to appreciate that these carbon oxides represent a yield loss of oxidizable compound and oxidant, not just solvent. Explicitly, a substantial and sometimes principal fraction of the carbon oxides comes from the oxidizable compound, and its derivatives, rather than from solvent; and often the oxidizable compound costs more per carbon unit than does solvent. Furthermore, it is important to appreciate that the desired product carboxylic acid (e.g., TPA) is also subject to over-oxidation to carbon oxides when present in the liquid phase of the reaction medium.

It is also important to appreciate that the present invention relates to reactions in the liquid phase of the reaction medium and to reactant concentrations therein. This is in contrast to some prior inventions that relate directly to the creation in precipitated solid form of aromatic compound retaining non-aromatic hydrocarbyl groups. Specifically, for the partial oxidation of para-xylene to TPA, certain prior inventions pertain to the amount of 4-CBA precipitated in the solid phase of CTA. However, the present inventors have discovered a variance of greater than two to one for the ratio of 4-CBA in the solid phase to 4-CBA in the liquid phase, using the same specifications of temperature, pressure, catalysis, solvent composition and space-time reaction rate of para-xylene, depending upon whether the partial oxidation is conducted in a well-mixed autoclave or in a reaction medium with oxygen and para-xylene staging according to the present invention. Further, the inventors have observed that the ratio of 4-CBA in the solid phase to 4-CBA in the liquid phase can also vary by over two to one in either well-mixed or staged reaction medium depending upon the space-time reaction rate of para-xylene at otherwise similar specifications of temperature, pressure, catalysis, and solvent composition. Additionally, 4-CBA in the solid phase CTA does not appear to contribute to the formation of noxious impurities, and 4-CBA in the solid phase can be recovered and oxidized on to TPA simply and at high yield (e.g., by oxidative digestion of the CTA slurry as is described herein); whereas the removal of noxious impurities is far more difficult and costly than removal of solid phase 4-CBA, and the production of carbon oxides represents a permanent yield loss. Thus, it is important to distinguish that this aspect of the present invention relates to liquid-phase compositions in the reaction medium.

Whether sourced from solvent or oxidizable compound, the inventors have discovered that at conversions of commercial utility the production of carbon oxides relates strongly to the level of overall reaction activity despite wide variation in the specific combination of temperature, metals, halogens, temperature, acidity of the reaction medium as measured by pH, water concentration employed to obtain the level of overall reaction activity. The inventors have found it useful for the partial oxidation of xylene to evaluate the level of overall reaction activity using the liquid-phase concentration of toluic acids at the mid-height of the reaction medium, the bottom of the reaction medium, and the top of the reaction medium.

Thus, there arises an important simultaneous balancing to minimize the creation of noxious impurities by increasing reaction activity and yet to minimize the creation of carbon oxides by lowering reaction activity. That is, if the overall production of carbon oxides is suppressed too low, then excessive levels of noxious impurities are formed, and vice versa.

Furthermore, the inventors have discovered that the solubility and the relative reactivity of the desired carboxylic acid (e.g., TPA) and the presence of other dissolved aromatic species lacking non-aromatic hydrocarbyl groups introduce a very important fulcrum in this balancing of carbon oxides versus noxious impurities. The desired product carboxylic acid is typically dissolved in the liquid phase of the reaction medium, even when also present in solid form. For example, at temperatures in the preferred ranges, TPA is soluble in a reaction medium comprising acetic acid and water at levels ranging from about one thousand ppmw to in excess of 1 weight percent, with solubility increasing as temperature increases. Notwithstanding that there are differences in the reaction rates toward forming various noxious impurities from oxidizable aromatic compound feed (e.g., para-xylene), from aromatic reaction intermediates (e.g., para-toluic acid), from the desired product aromatic carboxylic acid (e.g., TPA), and from aromatic species lacking non-aromatic hydrocarbyl groups (e.g., isophthalic acid), the presence and reactivity of the latter two groups establishes a region of diminishing returns with regards to further suppression of the former two groups, oxidizable aromatic compound feed and aromatic reaction intermediates. For example, in a partial oxidation of para-xylene to TPA, if dissolved TPA amounts to 7,000 ppmw in the liquid phase of the reaction medium at given conditions, dissolved benzoic acid amounts to 8,000 ppmw, dissolved isophthalic acid amounts to 6,000 ppmw, and dissolved phthalic acid amounts to 2,000 ppmw, then the value toward further lowering of total noxious compounds begins to diminish as reaction activity is increased to suppress the liquid-phase concentration para-toluic acid and 4-CBA below similar levels. That is, the presence and concentration in the liquid phase of the reaction medium of aromatic species lacking non-aromatic hydrocarbyl groups is very little altered by increasing reaction activity, and their presence serves to expand upwards the region of diminishing returns for reducing the concentration of reaction intermediates in order to suppress formation of noxious impurities.

Thus, one embodiment of the present invention provides preferred ranges of carbon oxides (carbon monoxide and carbon dioxide), bounded on the lower end by low reaction activity and excessive formation of noxious impurities and on the upper end by excessive carbon losses, but at levels lower than previously discovered and disclosed as commercially useful. Accordingly, the formation of carbon oxides is preferably controlled as follows. The ratio of moles of total carbon oxides produced to moles of oxidizable aromatic compound fed is preferably in the range of from about 0.02:1 to about 0.25:1, more preferably in the range of from about 0.04:1 to about 0.22:1, still more preferably in the range of from about 0.05:1 to about 0.19:1, and most preferably in the range of from 0.06:1 to 0.15:1. The ratio of moles of carbon dioxide produced to moles of oxidizable aromatic compound fed is preferably in the range of from about 0.01:1 to about 0.21:1, more preferably in the range of from about 0.03:1 to about 0.19:1, still more preferably in the range of from about 0.04:1 to about 0.16:1, and most preferably in the range of from 0.05:1 to 0.11:1. The ratio of moles of carbon monoxide produced to moles of oxidizable aromatic compound fed is preferably in the range of from about 0.005:1 to about 0.09:1, more preferably in the range of from about 0.01:1 to about 0.07:1, still more preferably in the range of from about 0.015:1 to about 0.05:1, and most preferably in the range of from 0.02:1 to 0.04.

The content of carbon dioxide in dry off-gas from the oxidation reactor is preferably in the range of from about 0.1 to about 1.5 mole percent, more preferably in the range of from about 0.20 to about 1.2 mole percent, still more preferably in the range of from about 0.25 to about 0.9 mole percent, and most preferably in the range of from 0.30 to 0.8 mole percent. The content of carbon monoxide in dry off-gas from the oxidation reactor is preferably in the range of from about 0.05 to about 0.6 mole percent, more preferably in the range of from about 0.10 to about 0.5 mole percent, still more preferably in the range of from 0.15 to about 0.35 mole percent, and most preferably in the range of from 0.18 to 0.28 mole percent.

The inventors have discovered that an important factor for reducing the production of carbon oxides to these preferred ranges is improving the purity of the recycled solvent and of the feed of oxidizable compound to reduce the concentration of aromatic compounds lacking non-aromatic hydrocarbyl groups according to disclosures of the present invention—this simultaneously reduces the formation of carbon oxides and of noxious impurities. Another factor is improving distribution of para-xylene and oxidant within the reaction vessel according to disclosures of the present invention. Other factors enabling the above preferred levels of carbon oxides are to operate with the gradients in the reaction medium as disclosed herein for pressure, for temperature, for concentration of oxidizable compound in the liquid phase, and for oxidant in the gas phase. Other factors enabling the above preferred levels of carbon oxides are to operate within the disclosures herein preferred for space-time reaction rate, pressure, temperature, solvent composition, catalyst composition, and mechanical geometry of the reaction vessel.

One possible benefit of operating within the preferred ranges of carbon oxide formation is that the usage of molecular oxygen can be reduced, though not to stoichiometric values. Notwithstanding the good staging of oxidant and oxidizable compound according to the present invention, an excess of oxygen must be retained above the stoichiometric value, as calculated for feed of oxidizable compound alone, to allow for some losses to carbon oxides and to provide excess molecular oxygen to control the formation of noxious impurities. Specifically for the case where xylene is the feed of oxidizable compound, the feed ratio of weight of molecular oxygen to weight of xylene is preferably in the range of from about 0.9:1 to about 1.5:1, more preferably in the range of from about 0.95:1 to about 1.3:1, and most preferably in the range of from 1:1 to 1.15:1. Specifically for xylene feed, the time-averaged content of molecular oxygen in the dry off-gas from the oxidation reactor is preferably in the range of from about 0.1 to about 6 mole percent, more preferably in the range of from about 1 to about 2 mole percent, and most preferably in the range of from 1.5 to 3 mole percent.

Another possible benefit of operating within the preferred ranges of carbon oxide formation is that less aromatic compound is converted to carbon oxides and other less valuable forms. This benefit is evaluated using the sum of the moles of all aromatic compounds exiting the reaction medium divided by the sum of the moles of all aromatic compounds entering the reaction medium over a continuous period of time, preferably one hour, more preferably one day, and most preferably 30 consecutive days. This ratio is hereinafter referred to as the "molar survival ratio" for aromatic compounds through the reaction medium and is expressed as a numerical percentage. If all entering aromatic compounds exit the reaction medium as aromatic compounds, albeit mostly in oxidized forms of the entering aromatic compounds, then the molar survival ratio has its maximum value of 100 percent. If exactly 1 of every 100 entering aromatic molecules is converted to carbon oxides and/or other non-aromatic molecules (e.g., acetic acid) while passing through reaction medium, then the molar survival ratio is 99 percent. Specifically for the case where xylene is the principal feed of oxidizable aromatic compound, the molar survival ratio for aromatic compounds through the reaction medium is preferably in the range of from about 98 to about 99.9 percent, more preferably in the range of from about 98.5 to about 99.8 percent, and most preferably in the range of from 99.0 to 99.7 percent.

Another aspect of the current invention involves the production of methyl acetate in a reaction medium comprising acetic acid and one or more oxidizable aromatic compounds. This methyl acetate is relatively volatile compared to water and acetic acid and thus tends to follow the off-gas unless additional cooling or other unit operations are employed to recover it and/or to destroy it prior to releasing the off-gas back to the environment. The formation of methyl acetate thus represents an operating cost and also a capital cost. Perhaps the methyl acetate is formed by first combining a methyl radical, perhaps from decomposition of acetic acid, with oxygen to produce methyl hydroperoxide, by subsequently decomposing to form methanol, and by finally reacting the produced methanol with remaining acetic acid to form methyl acetate. Whatever the chemical path, the inventors have discovered that whenever methyl acetate production is at too low a rate, then the production of carbon oxides are also too low and the production of noxious aromatic impurities are too high. If methyl acetate production is at too high a rate, then the production of carbon oxides are also unnecessarily high leading to yield losses of solvent, oxidizable compound and oxidant. When employing the preferred embodiments disclosed herein, the production ratio of moles of methyl acetate produced to moles of oxidizable aromatic compound fed is preferably in the range of from about 0.005:1 to about 0.09:1, more preferably in the range of from about 0.01:1 to about 0.07:1, and most preferably in the range of from 0.02:1 to about 0.04:1.

When the generation of carbon dioxide, carbon monoxide, their sum, and/or methyl acetate are below the preferred ranges disclosed herein or when the molar survival ratio for aromatic compounds is above the preferred ranges disclosed herein, the reaction activity should be increased or the STR should be reduced. One activity accelerator is increased temperature, within the preferred ranges disclosed herein. Another activity accelerator is increased catalytic activity as provided by the mixture of catalytic chemicals and solvent. Generally, increasing cobalt and/or bromine concentrations will accelerate reaction activity, if these are being used within the ranges preferred herein. Adjusting the concentration within the reaction medium of other catalyst components and of water can also be used to accelerate reaction activity. STR is decreased by decreasing the feed rate of oxidizable compound and/or by increasing the volume of reaction medium.

When the generation of carbon dioxide, carbon monoxide, their sum, and/or methyl acetate is greater than the preferred ranges disclosed herein and/or when the molar survival ratio for aromatic compounds is below the preferred ranges disclosed herein, preferable control actions include a reverse of the above actions, again within the preferred ranges disclosed herein. The inventors note that it is particularly helpful to raise the STR as far as possible into the ranges herein while maintaining a good quality of oxidation as measured by noxious impurities in the CTA and in the reaction medium. The inventors again note that it is difficult to maintain this quality of oxidation at such high STR and that very careful attention is required with respect toward the following: to feed dispersion upon entering the reaction medium, to aeration quality throughout the reaction medium, to de-aeration upon exit from the reaction medium, to oxygen-STR and dissolved oxygen throughout the reaction medium, to excess oxidant exiting the reaction medium, to the desirable spatial gradient of oxygen-STR, to the desirable spatial gradient of oxidizable compound concentration, to the desirable spatial gradient of oxidant concentration, to the overhead pressure, to the desirable spatial gradient of pressure, and to the preferred temperature at the mid-height of the reaction medium, and as are all disclosed herein. In further addition and in order to achieve lower carbon dioxide, carbon monoxide, and/or their sum and/or in order to increase the molar survival ratio for aromatic compounds, the inventors have discovered that it is useful to suppress within the reaction medium the concentration of soluble aromatic compounds lacking non-aromatic hydrocarbyl groups (e.g. isophthalic acid, phthalic acid and benzoic acid); this suppression may be effected by using purer feed of oxidizable compound and/or purer solvent, especially within the preferred ranges for each as disclosed herein.

In a reaction medium continuously oxidizing para-xylene to terephthalic acid at the preferred STR disclosed herein, it is preferred that the amount of para-toluic acid in the liquid phase of the reaction medium be maintained in the range from about 200 to about 10,000 ppmw, more preferably from about 800 to about 8,000 ppmw and most preferably from 1,600 to 6,000 ppmw. Furthermore, conversion of para-xylene to terephthalic acid within the reaction medium is preferably maintained above about 50 mole percent, more preferably above about 90 mole percent, still more preferably above about 95 mole percent, and most preferably above 97 mole percent.

In one embodiment of the present invention, it is preferred for one or more of the operating parameters disclosed herein (including numerically-quantified operating parameters) to be maintained for a commercially-significant period of time. Preferably, operation in accordance with one or more of above-described operating parameters is maintained for at least about 1 hour, more preferably, at least about 12 hours, still more preferably at least about 36 hours, and most preferably at least 96 hours. Thus, unless otherwise indicated herein, the operating parameters described herein are intended to apply to steady-state, optimal/commercial operation—not start-up, shut-down, or sub-optimal operation.

The inventors note that for all numerical ranges provided herein, the upper and lower ends of the ranges can be independent of one another. For example, a numerical range of 10 to 100 means greater than 10 and/or less than 100. Thus, a range of 10 to 100 provides support for a claim limitation of greater than 10 (without the upper bound), a claim limitation of less than 100 (without the lower bound), as well as the full 10 to 100 range (with both upper and lower bounds). Further, when the term "about" is used to modify a numerical value, it should be understood that in one embodiment, the numerical value is the exact numerical value.

The invention has been described in detail with particular reference to preferred embodiments thereof, but will be understood that variations and modification can be effected within the spirit and scope of the invention.

We claim:

1. A process for making a polycarboxylic acid composition, said process comprising:
   (a) subjecting a multi-phase reaction medium to oxidation in a primary oxidation reactor to thereby produce a first slurry;
   (b) subjecting at least a portion of said first slurry to further oxidation in a secondary oxidation reactor, wherein said secondary oxidation reactor is a bubble column reactor, wherein said primary oxidation reactor defines therein a primary reaction zone, wherein said secondary oxidation reactor defines therein a secondary reaction zone, wherein the ratio of the volume of said primary reaction zone to the volume of said secondary reaction zone is in the range of from about 4:1 to about 50:1;
   wherein at least 80 weight percent of said aromatic compound introduced into said primary oxidation reactor is oxidized in said primary oxidation reactor; and
   whereby overhead gasses are transferred from the top of the secondary oxidation reactor to the primary oxidation reactor.

2. The process of claim 1, wherein said aromatic compound is para-xylene.

3. The process of claim 1 wherein step (b) includes oxidizing para-toluic acid present in said first slurry.

4. The process of claim 3 further comprising withdrawing a second slurry from said secondary oxidation reactor, wherein the time-averaged concentration of para-toluic acid in the liquid phase of said second slurry is less than 50 percent of the time-averaged concentration of para-toluic acid in the liquid phase of said first slurry.

5. The process of claim 4 wherein the time-averaged concentration of para-toluic acid in the liquid phase of said first slurry is at least 500 ppmw, wherein the time-averaged concentration of para-toluic acid in the liquid phase of said second slurry is less than 250 ppmw.

6. The process of claim 1 wherein said primary oxidation reactor is a bubble column reactor.

7. The process of claim 1 wherein said secondary oxidation reactor is located outside of said primary oxidation reactor.

8. The process of claim 7 wherein at least a portion of said secondary oxidation reactor is located alongside said primary oxidation reactor.

9. The process of claim 1 wherein said secondary oxidation reactor is not a piston flow reactor.

10. The process of claim 1 further comprising removing said first slurry from said primary oxidation reactor via a slurry outlet located between the top and bottom ends of said primary oxidation reactor.

11. The process of claim 10 wherein said primary oxidation reactor defines therein a primary reaction zone having a maximum height ($H_p$), wherein said slurry outlet is spaced at least $0.1H_p$ from the bottom and top ends of said primary reaction zone.

12. The process of claim 11 wherein said slurry outlet is spaced at least $0.25H_p$ from the bottom and top ends of said primary reaction zone.

13. The process of claim 1 wherein said primary reaction zone has a ratio of maximum vertical height to maximum horizontal diameter in the range of from about 3:1 to about 30:1, wherein said secondary reaction zone has a ratio of maximum vertical height to maximum horizontal diameter in the range of from about 1:1 to about 50:1.

14. The process of claim 1 wherein the ratio of the maximum horizontal diameter of said secondary reaction zone to the maximum horizontal diameter of said primary reaction zone is in the range of from about 0.1:1 to about 0.6:1, wherein the ratio of the maximum vertical height of said secondary reaction zone to the maximum vertical height of said primary reaction zone is in the range of from about 0.1:1 to about 0.9:1.

15. The process of claim 1 wherein said primary reaction zone has a maximum diameter ($D_p$), wherein the volumetric centroid of said secondary reaction zone is horizontally spaced at least $0.5D_p$ from the volumetric centroid of said primary reaction zone.

16. The process of claim 15 wherein said primary reaction zone has a maximum height ($H_p$), wherein the volumetric centroid of said secondary reaction zone is vertically spaced less than $0.5H_p$ from the volumetric centroid of said primary reaction zone.

17. A process for making a polycarboxylic acid composition, said process comprising:
   (a) subjecting a multi-phase reaction medium to oxidation in a primary oxidation reactor to thereby produce a first slurry;
   (b) subjecting at least a portion of said first slurry to further oxidation in a secondary oxidation reactor to thereby produce a second slurry comprising crude polycarboxylic acid particles, wherein said secondary oxidation reactor is a bubble column reactor, wherein the time-averaged concentration of para-toluic acid in the liquid phase of said first slurry is at least 1,000 ppmw, wherein the time-averaged concentration of para-toluic acid in the liquid phase of said second slurry is less than 1,000 ppmw; and
   (c) subjecting at least a portion of said second slurry to at least one chemical reaction to thereby produce a third slurry comprising purified polycarboxylic acid particles, wherein said purified polycarboxylic acid particles comprise a concentration of 4-carboxybenzaldehyde ("4-CBA") that is at least 200 ppmw less than the 4-CBA concentration of said crude polycarboxylic acid particles; and
   whereby overhead gasses are transferred from the top of the secondary oxidation reactor to the primary oxidation reactor.

18. The process of claim 17, wherein said primary oxidation reactor and said secondary oxidation reactor are each operated at a time-averaged and volume-averaged temperature in the range of from about 140 to about 180° C., wherein the overhead pressure of said primary oxidation reactor and said secondary oxidation reactor are each maintained in the range of from about 1 to about 20 barg.

19. The process of claim 17, wherein the pressure and temperature in said secondary oxidation reactor are approximately equal to the pressure and temperature in said primary oxidation reactor.

20. The process of claim 17, wherein said primary oxidation reactor defines therein a primary reaction zone, wherein said secondary oxidation reactor defines therein a secondary reaction zone, wherein the ratio of the volume of said primary reaction zone to the volume of said secondary reaction zone is in the range of from about 4:1 to about 50:1.

21. The process of claim 20, wherein the ratio of the volume of said primary reaction zone to the volume of said secondary reaction zone is in the range of from 8:1 to 30:1.

22. The process of claim 17, wherein said secondary oxidation reactor defines therein a secondary reaction zone, wherein the liquid phase of said first slurry has a residence time in said secondary reaction zone in the range of from about 2 to about 60 minutes.

23. The process of claim 17, wherein said chemical reaction of step (c) is performed at a temperature in the range of from about 20 to about 80° C. higher than the time-averaged and volume-averaged temperature in said primary oxidation reactor and in said secondary oxidation reactor.

24. The process of claim 17, wherein said chemical reaction of step (c) includes oxidative digestion.

25. The process of claim 17, wherein the total concentration of solids in said first slurry is at least 15 weight percent.

26. The process of claim 17, wherein said primary oxidation reactor is a bubble column reactor.

27. The process of claim 17, wherein said aromatic compound is para-xylene.

28. The process of claim 1, wherein the liquid phase of said initial slurry has a residence time in said secondary reaction zone in the range of from about 2 to about 60 minutes.

29. The process of claim 1, wherein said primary oxidation reactor and said secondary oxidation reactor are each operated at a time-averaged and volume-averaged temperature in the range of from about 140 to about 180° C., wherein the overhead pressure of said primary oxidation reactor and said secondary oxidation reactor are each maintained in the range of from about 1 to about 20 barg.

30. The process of claim 1, wherein the pressure and temperature in said secondary oxidation reactor are approximately equal to the pressure and temperature in said primary oxidation reactor.

* * * * *